United States Patent [19]

Jikihara et al.

[11] Patent Number: 4,536,209
[45] Date of Patent: Aug. 20, 1985

[54] N-(3-SUBSTITUTED OXYPHENYL)TETRAHYDROPHTHALIMIDES AND HERBICIDAL COMPOSITION

[75] Inventors: Tetsuo Jikihara, Kawasaki; Masatsugu Oda, Yokohama; Bunji Natsume, Yokohama; Hisao Watanabe, Yokohama; Seiichi Suzuki, Yokohama, all of Japan

[73] Assignee: Mitsubishi Chemical Industries Ltd., Tokyo, Japan

[21] Appl. No.: 308,825

[22] Filed: Oct. 5, 1981

[30] Foreign Application Priority Data

Oct. 7, 1980 [JP] Japan ............................ 55-140076
Oct. 9, 1980 [JP] Japan ............................ 55-141778
Oct. 9, 1980 [JP] Japan ............................ 55-141776

[51] Int. Cl.³ .................... C07D 209/48; A01N 43/38
[52] U.S. Cl. ........................................ 71/96; 71/90; 71/92; 71/94; 548/181; 548/240; 548/465; 548/513; 544/63; 544/144; 544/331; 546/201; 546/273
[58] Field of Search .............. 548/181, 240, 465, 513; 544/144, 331, 63; 546/201, 273; 71/96, 94, 90, 92

[56] References Cited

U.S. PATENT DOCUMENTS

| | | | |
|---|---|---|---|
| 3,465,001 | 9/1969 | Bolhofer et al. ................... | 548/513 |
| 3,878,224 | 4/1975 | Matsui et al. ...................... | 71/94 |
| 3,984,435 | 10/1976 | Matsui et al. ...................... | 71/96 |
| 3,987,057 | 10/1976 | Goddard ............................ | 71/96 |
| 3,992,189 | 11/1976 | Goddard ............................ | 71/96 |
| 4,001,272 | 1/1977 | Goddard ............................ | 71/96 |
| 4,032,326 | 6/1977 | Goddard ............................ | 71/96 |
| 4,124,375 | 11/1978 | Bollinger et al. .................. | 71/96 |
| 4,157,256 | 6/1979 | Hiraga et al. ..................... | 71/95 |
| 4,175,948 | 11/1979 | Goddard et al. ................... | 71/96 |
| 4,292,070 | 9/1981 | Wakabayashi et al. ............ | 71/96 |
| 4,332,944 | 1/1982 | Anderson et al. ................. | 71/94 |

FOREIGN PATENT DOCUMENTS 2374847  7/1978  France .

OTHER PUBLICATIONS

H. Ohta et al., Pesticide Biochemistry and Physiology 14, 153–160, (1980).

*Primary Examiner*—Donald G. Daus
*Assistant Examiner*—William A. Teoli, Jr.
*Attorney, Agent, or Firm*—Oblon, Fisher, Spivak, McClelland & Maier

[57] ABSTRACT

$\Delta'$-Tetrahydrophthalimides having a substituted oxy group at 3-position and, if necessary, a halogen atom at 4-position and/or at 2-position of phenyl group as N-substituent have excellent herbicidal activity and are useful as selective herbicides.

12 Claims, No Drawings

N-(3-SUBSTITUTED OXYPHENYL)TETRAHYDROPHTHALIMIDES AND HERBICIDAL COMPOSITION

BACKGROUND OF THE INVENTION

The present invention relates to novel N-substituted tetrahydrophthalimides and herbicidal compositions thereof.

N-substituted aryl-Δ'-tetrahydrophthalimide derivatives having herbicidal activity have been reported.

For example, Japanese Examined Patent Publication No. 11940/1973 (U.S. Pat. No. 3,878,224 and U.S. Pat. No. 3,984,435 and West German Unexamined Patent Publication No. 2,165,651) discloses N-substituted-Δ'-tetrahydrophthalimide which is represented by the general formula

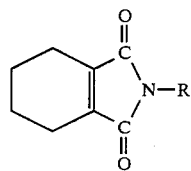

wherein R may be an aryl or aralkyl as phenyl optionally substituted with 1 to 5 halogen atoms; hydroxy, alkoxy, nitro, cyano, thiocyanno, carboxy, halogenated alkyl, alkyl, phenyl and OCH$_2$A (wherein A is phenyl or naphthyl) group and the like may also be substituted therein. N-(4-chloro-3-methoxyphenyl)-Δ'-tetrahydrophthalimide and N-(4-bromo-3-methoxyphenyl)-Δ'-tetrahydrophthalimide are described as the exemplified compounds having the formula wherein R is a halogen- and alkoxy-substituted phenyl group.

U.S. Pat. No. 4,001,272 and U.S. Pat. No. 4,032,326 disclose herbicidal 2-substituted aryl-4,5,6,7-tetrahydro-2H-isoindole-1,3-diones of the following formula:

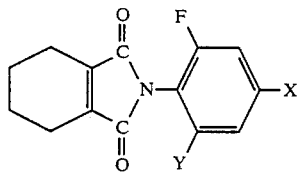

wherein X is Cl, Br or F and Y is H or F.

Degree of these compounds are highly affected by minor changes of a kind, a number or a position of substituents in the structure. Thus, it is difficult to predict herbicidal effects of novel compounds in view of similarity of chemical structures.

The inventors have studied novel tetrahydrophthalimides as an active ingredient of a herbicidal composition and have found that the specific novel N-aryl-3,4,5,6-tetrahydrophthalimides having H or a halogen atom at 2-position, a halogen atom at 4-position and a specific substituent at 5-position have excellent herbicidal effect.

SUMMARY OF THE INVENTION

The present invention is to provide novel N-substituted 3,4,5,6-tetrahydrophthalimides which are represented by the general formula

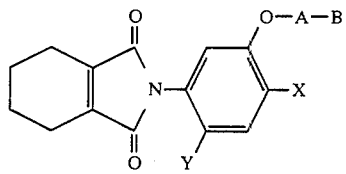

wherein X and Y respectively represent hydrogen or a halogen atom;

A represents $-(C)_n^{R^1}_{R^2}-$, $-\underset{CHCH_3}{\underset{\|}{C}}-$, or $-CH_2CH=CH-$;

B represents $-\underset{O}{\underset{\|}{C}}-OR^3$, $-\underset{O}{\underset{\|}{C}}-SR^4$, $-\underset{O}{\underset{\|}{C}}-O(CH)_m\underset{R^5}{\underset{|}{-}}\underset{O}{\underset{\|}{C}}-R^6$, $-\underset{O}{\underset{\|}{C}}-N\underset{R^8}{\overset{R^7}{\diagdown}}$ or —CN; R$^1$ represents hydrogen atom or an alkyl, phenyl or a substituted phenyl group; R$^2$ represents hydrogen atom or an alkyl group; R$^3$ represents hydrogen atom or an alkyl, alkenyl, alkynyl, haloalkyl, haloalkenyl, cyanoalkyl, hydroxyalkyl, alkoxyalkyl, alkoxyalkoxyalkyl, alkoxyalkoxyalkoxyalkyl, alkylthioalkyl, cycloalkyl, aralkyl, phenyl, γ-butyrolactone group which can be substituted by methyl group or salt moiety; R$^4$ represents an alkyl, alkoxycarbonylalkyl or benzyl group; R$^5$ represents hydrogen atom or methyl group; R$^6$ represents methyl or phenyl group; R$^7$ and R$^8$ can be the same or different and respectively represent hydrogen atom, an alkyl, alkenyl, alkynyl, haloalkyl, hydroxyalkyl, alkoxyalkyl, aralkyl, phenyl, substituted phenyl, heterocyclic ring, alkoxy, alkenyloxy, amino, mono-substituted amino, di-substituted amino, alkanesulfonyl, benzenesulfonyl, substituted benzenesulfonyl or cycloalkyl group or

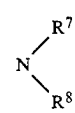

can form a heterocyclic ring which can have —O—; and m and n respectively represent an integer of 1 to 3.

DETAILED DESCRIPTION OF THE PREFERRED EMBODIMENTS

The compounds having the formula (I) of the present invention are novel compounds. The typical compounds as herbicides can be the compounds having the formula (I) wherein X represents Cl, Br, I or H; preferably Cl, Br or H; Y represents H, F or Cl, preferably H or Cl (especially X is Cl, Br or H when Y is H; and X is Cl when Y is Cl); A represents

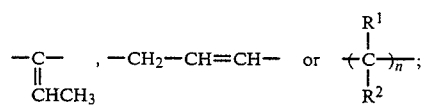

$R^1$ represents H or a $C_{1-10}$ alkyl group such as methyl, ethyl, n-propyl, isopropyl, n-butyl, isobutyl, sec-butyl, n-pentyl, n-hexyl, n-heptyl, n-octyl, n-nonyl and n-decyl, preferably a $C_{1-7}$ alkyl group such as methyl, ethyl n-propyl, isopropyl, n-butyl, isobutyl, n-pentyl, n-hexyl or n-heptyl group; $R^1$ represents phenyl or substituted phenyl group such as chlorophenyl, bromophenyl, dichlorophenyl, methylchlorophenyl, methylphenyl or nitrophenyl group, preferably substituted phenyl group such as chlorophenyl, bromophenyl, dichlorophenyl, and methylchlorophenyl group; $R^2$ represents hydrogen atom or a $C_{1-4}$ alkyl group such as methyl, ethyl propyl or butyl group preferably H or methyl group; n represents an integer of 1 to 3, preferably $R^1$ and $R^2$ are hydrogen atoms when n is an integer of 2 or 3.

When B is

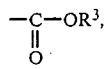

$R^3$ represents H or a $C_{1-12}$ straight or branched alkyl group preferably a $C_{1-6}$ alkyl group such as methyl, ethyl, n-propyl, isopropyl, n-butyl, isobutyl, sec-butyl, t-butyl, n-pentyl, 3-methylbutyl, 2,3-dimethylpropyl and n-hexyl group; a $C_{2-5}$ alkenyl group such as vinyl, allyl, methallyl, 2-butenyl and 3-methyl-2-butenyl group preferably $C_{3-4}$ alkenyl group; a $C_{2-5}$ alkynyl group such as propargyl, butynyl, and 1,1-dimethylpropargyl group preferably $C_{3-4}$ alkynyl group; a $C_{1-5}$ haloalkyl group having one to four of chloro, bromo, iodo or fluoro groups preferably a $C_{2-4}$ haloalkyl group having 1 to 4 halogen atoms such as fluoroethyl, chloroethyl, bromoethyl, dichloroethyl, dibromoethyl, trifluoroethyl, trichloroethyl, chloropropyl, bromopropyl, dichloropropyl, dibromopropyl, tetrafluoropropyl, chlorobutyl or bromobutyl; a $C_{3-4}$ haloalkenyl group having 1 to 3 halogen atoms (Br, I, F, or Cl), preferably a $C_3$ haloalkenyl group having 1 to 3 chlorine atoms such as chloroallyl, dichloroallyl or trichloroallyl group; a $C_{2-4}$ cyanoalkyl such as cyanomethyl, cyanoethyl, or cyanopropyl group; a $C_{2-4}$ hydroxyalkyl group such as hydroxyethyl, hydroxypropyl and hydroxybutyl group; alkoxyalkyl, alkoxyalkoxyalkyl or alkoxyalkoxyalkoxyalkyl group having 1 to 3 of $C_{1-7}$ alkoxy groups and a $C_{1-5}$ alkyl group preferably a $C_{3-6}$ alkoxyalkyl group such as methoxyethyl, ethoxyethyl, propoxyethyl, butoxyethyl, methoxypropyl, ethoxypropyl and propoxypropyl group; a $C_{5-8}$ alkoxyalkoxyalkyl group such as methoxyethoxyethyl, ethoxyethoxyethyl, propoxyethoxyethyl, butoxyethoxyethyl and methoxypropoxypropyl group; a $C_{7-10}$ alkoxyalkoxyalkoxyalkyl group such as methoxyethoxyethoxyethyl, ethoxyethoxyethoxyethyl, propoxyethoxyethoxyethyl, butoxyethoxyethoxyethyl and methoxypropoxypropoxypropyl group; a $C_{3-8}$ alkylthioalkyl group such as methylthioethyl, ethylthioethyl, propylthioethyl, butylthioethyl and pentylthioethyl group; a $C_{4-8}$ cycloalkyl group preferably a $C_{4-7}$ cycloalkyl group such as cyclobutyl, cyclopentyl, cyclohexyl and cycloheptyl group; a $C_{7-9}$ aralkyl group such as benzyl, chlorobenzyl, bromobenzyl, methylbenzyl, α-methylbenzyl, α,α-dimethylbenzyl, phenethyl, methylphenethyl and phenylpropyl group; phenyl group; γ-butyrolactone group which can be substituted by methyl group and $R^3$ can be salt moiety such as alkali metals and alkaline earth metals such as Na, K and Ca; and ammonium groups having 0 to 4 alkyl groups having a total carbon atom content of 1 to 9 such as ammonium, methylammonium, ethylammonium, propylammonium, butylammonium, pentylammonium, hexylammonium, dimethylammonium, diethylammonium, dipropylammonium, dibutylammonium, trimethylammonium, triethylammonium, tripropylammonium, tetramethylammonium and tetraethylammonium group.

When B is

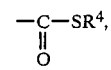

$R^4$ represents a $C_{1-12}$ alkyl group preferably a $C_{1-10}$ alkyl group such as methyl, ethyl, n-propyl, isopropyl, n-butyl, isobutyl, n-pentyl, sec-pentyl, n-hexyl, n-heptyl, n-octyl, n-nonyl and n-decyl group; a $C_{3-6}$ alkoxycarbonylalkyl group such as methoxycarbonylmethyl, ethoxycarbonylmethyl, propoxycarbonylmethyl and butoxycarbonylmethyl group and benzyl group.

When B is

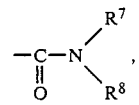

$R^7$ and $R^8$ can be the same or different and respectively represent H or a $C_{1-10}$ straight or branched alkyl group preferably a $C_{1-7}$ alkyl group such as methyl, ethyl, n-propyl, isopropyl, n-butyl, isobutyl, sec-butyl, t-butyl, n-pentyl, n-hexyl and n-heptyl group; a $C_{2-5}$ alkenyl group preferably a $C_{3-4}$ alkenyl group such as allyl, methallyl and 2-butenyl group; a $C_{2-5}$ alkynyl group such as propargyl, 2-butynyl and 1,1-dimethylpropargyl group, preferably $C_{3-4}$ alkynyl group; a $C_{2-6}$ haloalkyl group preferably a $C_{2-4}$ haloalkyl group such as chloroethyl, chloropropyl and chlorobutyl group; a $C_{2-6}$ hydroxyalkyl group preferably a $C_{2-4}$ hydroxyalkyl group such as hydroxyethyl, hydroxypropyl and hydroxybutyl group; phenyl group; substituted phenyl group such as chlorophenyl, bromophenyl, methylphenyl and methoxyphenyl group especially phenyl, chlorophenyl, methylphenyl or methoxyphenyl group; a 5- or 6-membered heterocyclic ring group having at least one nitrogen atom such as pyridyl, pyrimidyl, triazinyl, thiazolyl, oxazolyl, diazolyl and triazolyl group; a $C_{1-6}$ alkoxy group preferably a $C_{1-4}$ alkoxy group such as methoxy, ethoxy, propoxy and butoxy group; a $C_{2-4}$ alkenyloxy group such as vinyloxy, allyloxy, methallyloxy and 2-butenyloxy; amino group; mono-substituted amino group such as methylamino and phenylamino group; di-substituted amino group such as dimethylamino group; a $C_{1-4}$ alkanesulfonyl group such as methanesulfonyl, ethanesulfonyl, propanesulfonyl and butanesulfonyl group; benzenesulfonyl group; substituted benzenesulfonyl group such as toluenesulfonyl, chlorobenzenesulfonyl and methoxybenzenesulfonyl group; and

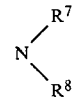

can form a heterocyclic ring group which can have —O— as a 5- to 7-membered heterocyclic group such as pyrolidino, piperidino, morpholino, and hexahydroazepino group especially the 6-membered heterocyclic group such as piperidino or morpholino group. B can be

The compounds having the formula (I) can be various isomers such as optical isomers, diastereoisomers, and Z-E isomers. These isomers and mixtures are included in the definition of the present invention. These isomers are usually obtained in the form of a mixture thereof. In the examples, mixtures of the isomers are formed otherwise specified.

These isomers can be separated by various processes such as asymmetric synthesis, optical resolution and various chromatography such as column chromatography, thin layer chromatography and high speed liquid chromatography.

For example, the following compounds (I) are obtained in the form of isomers.

Optical isomers;

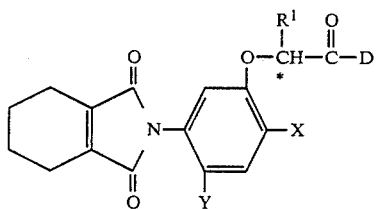

(*C: asymmetric carbon atom; D: $-OR^3$, $-SR^4$,

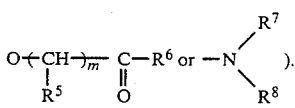

The compounds (a) can be optical isomers when $R^1$ is other than hydrogen atom or when D has asymmetric carbon atom in the case of $R^1$ is H.

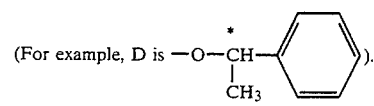

Z-E isomers:

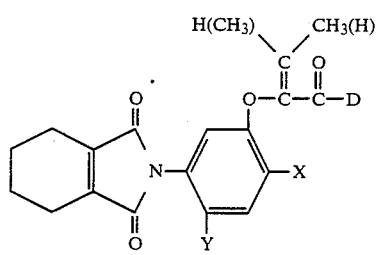

The compounds (b) can be Z-E isomers.

Diastereoisomers:

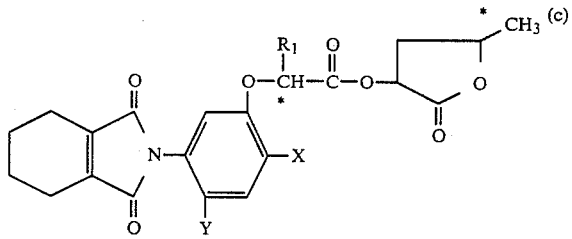

The compounds (c) have two asymmetric carbon atoms to give diastereoisomers.

The compounds having the formula (I) can be produced by the following processes:

Process (1)

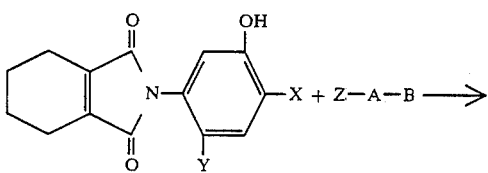

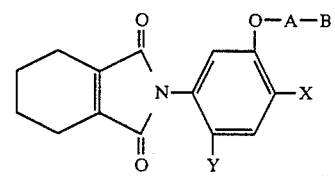

wherein X, Y, A and B are the same as defined in the formula (I) and Z represents a halogen atom.

The reaction is carried out in a solvent such as acetone, ethyl methyl ketone, benzene, toluene, acetonitrile, tetrahydrofuran, and N,N-dimethylformamide in the presence of a base such as sodium carbonate, potassium carbonate, sodium hydroxide and potassium hydroxide or a fluoride such as potassium fluoride, cesium fluoride and tetra n-butyl ammonium fluoride in the presence or absence of an iodide such as sodium iodide and potassium iodide at 0° to 150° C.

Process (2)

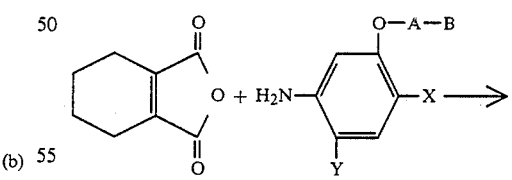

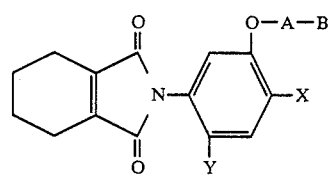

The reaction of the tetrahydrophthalic anhydride with the aniline is carried out in the absence or presence of a solvent such as acetic acid, toluene, dioxane, methanol and water at 60° to 200° C.

Process (3)

The compounds having the formula (I) wherein B is

can be produced by the following reaction.

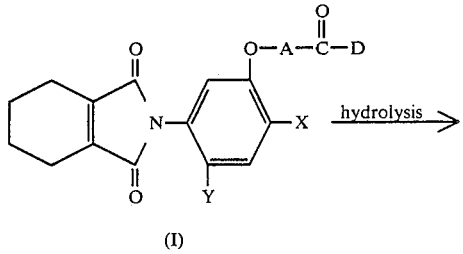

wherein D is $OR^3$ ($R^3$ is other than hydrogen atom), $-SR^4$,

preferably D is methoxy or ethoxy group. The compounds (I') can be produced by the process (1) or (2).

The hydrolysis can be carried out by the following conditions:

(i) in a solvent such as water, water-methanol, water-ethanol and dioxane in the presence of an acid such as hydrochloric acid and sulfuric acid at 0° to 120° C. or in a solvent such as formic acid and acetic acid in the presence of methanesulfonic acid and p-toluenesulfonic acid at 80° to 180° C.;

(ii) in a solvent such as N,N-dimethylformamide, N-methyl-2-pyrolidone, 2,4,6-collidine, 2,6-lutidine and pyridine, in the presence of lithium hydroxide, lithium bromide, lithium iodide and sodium iodide at 100° to 200° C.

(iii) in a solvent such as water, water-methanol, water-ethanol, water-dioxane and water-acetone in the presence of sodium hydroxide, potassium hydroxide and barium hydroxide at −20° C. to 150° C. After the reaction, the solvent is distilled off and the reaction is carried out in a solvent such as acetic acid, dilute hydrochloric acid and dilute hydrochloric acid-dioxane at 50° to 200° C.

Process (4)

When B has

group in the formula (I), the compounds can be effectively produced by the following process.

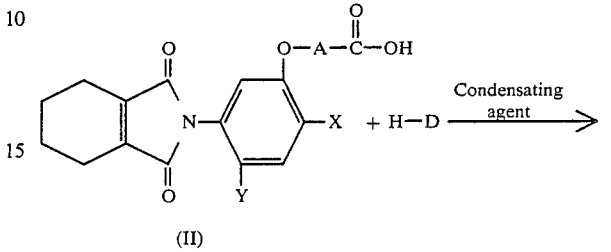

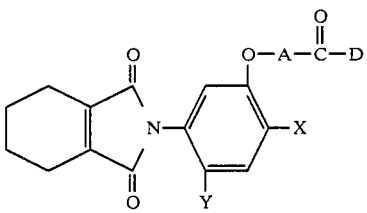

wherein D is $-OR^3$, $-SR^4$,

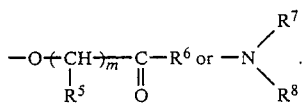

The reaction can be carried out in the absence of a solvent or in the presence of a solvent such as benzene, toluene, methyl chloride, chloroform, carbon tetrachloride, tetrahydrofuran, N,N-dimethylformamide, acetonitrile and pyridine in the presence of a reagent of thionyl chloride, phosphorous oxychloride, ethyl chlorocarbonate and N,N-dicyclohexylcarbodiimide in the presence or absence of a base such as triethylamine and N,N-diethylaniline at −20° C. to 150° C.

The carboxylic acid derivatives used as the starting material in the process are converted into intermediates such as acid chlorides, mixed acid anhydrides and acid anhydrides by the reaction of the reagent. The intermediates are converted into the object compounds by the reaction with a reagent such as alcohols, thiols and amines. The intermediates can be isolated in the process.

When A is

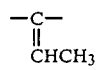

group and B has

group in the formula (I), the compounds can be effectively produced by the following process.

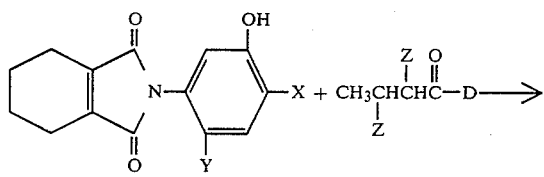

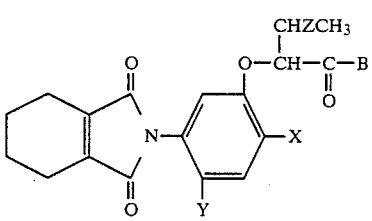

wherein Z represents a halogen atom such as Cl, Br or I.

The reaction is carried out in a solvent such as acetone, ethyl methyl ketone, benzene, toluene, acetonitrile, tetrahydrofuran and N,N-dimethylformamide in the presence of a base such as sodium carbonate, potassium carbonate, sodium hydroxide and potassium hydroxide in the presence or absence of sodium iodide or potassium iodide at 0° to 150° C. The reaction may be performed through the following intermediate.

Process (6)

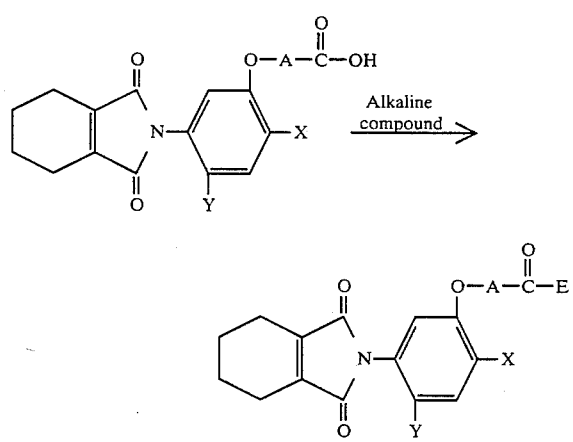

wherein E represents OR$^3$ and R$^3$ is a salt moiety.

The reaction for production of the salt is carried out in a solvent such as water, water-methanol, water-ethanol, benzene, toluene and tetrahydrofuran at −20° C. to 150° C. The alkaline compounds used in the reaction can be an alkali or alkaline earth metal hydroxide such as sodium hydroxide, potassium hydroxide and calcium hydroxide; an alkali hydride such as sodium hydride and potassium hydride; an alkali metal such as metallic sodium and potassium, ammonia and mono-, di- or tri-alkylamine.

The processes for producing the compounds (I) of the present invention will be illustrated by certain examples which are provided for purposes of illustration only and are not intended to be limiting the present invention.

EXAMPLE 1

Production of N-[4-bromo-3-(1-ethoxycarbonylbutyloxy)phenyl]-3,4,5,6-tetrahydrophthalimide A mixture of 15.0 g. of N-(4-bromo-3-hydroxyphenyl)-3,4,5,6-tetrahydrophthalimide, 12.0 g. of ethyl α-bromovalerate, 7.7 g. of potassium carbonate, 2.5 g. of potassium iodide and 50 ml. of acetone was refluxed with stirring for 3 hours and then, the reaction mixture was cooled to room temperature and the salt was separated by a filtration. The filtrate was concentrated under a reduced pressure and 2N-HCl was added to the residue to crystallize the product. The crystal was separated by a filtration and washed with water and dried. The residue was purified by a chromatography on a column of silica gel (developing solvent: ethyl acetate: n-hexane of 1:3) to obtain 17.6 g. of Compound No. 90 shown in table 1.

EXAMPLE 2

Production of N-[4-bromo-3-(1-ethoxycarbonylethyloxy)phenyl]-3,4,5,6-tetrahydrophthalimide A mixture of 2.88 g. of 1.52 g. of cyclohexane-1,2-dicarboxylic anhydride 2.88 g. of 4-bromo-3-(1-ethoxycarbonylethyloxy)aniline ($n_D^{25} = 1.5590$) and 10 ml. of acetic acid was refluxed with stirring for 2 hours and the reaction mixture was cooled to room temperature and water was added. The precipitate was separated by a filtration and was recrystallized from a mixture of benzene-cyclohexane to obtain 3.89 g. of Compound No. 18 shown in Table 1.

EXAMPLE 3

Production of N-[2,4-dichloro-5-(1-carboxyethyloxy)phenyl]-3,4,5,6-tetrahydrophthalimide A mixture of 14.4 g. of N-[2,4-dichloro-5-(1-ethoxycarbonylethyloxy)phenyl]-3,4,5,6-tetrahydrophthalimide, 3.40 g. of methanesulfonic acid and 35 ml. of 86% formic acid was refluxed with stirring for 15 hours and the reaction mixture was cooled to room temperature and water was added and the product was extracted with ethyl acetate. The extract was concentrated under a reduced pressure and the oily product was admixed with n-hexane and was triturated to obtain the crystals. The product was recrystallized from benzene-cyclohexane to obtain 8.7 g. of Compound No. 11 shown in Table 1.

EXAMPLE 4

Production of N-[4-bromo-3-(1-carboxyethyloxy)phenyl]-3,4,5,6-tetrahydrophthalimide A mixture of 1 g. of N-[4-bromo-3-(1-ethoxycarbonylethyloxy)phenyl]-3,4,5,6-tetrahydrophthalimide, 5 g. of lithium iodide and 120 ml. of anhydrous N,N-dimethylformamide was heated with stirring in nitrogen gas flow at 140° C. for 1.5 hours and the reaction mixture was cooled to room temperature and 2N-HCl was added and the product was extracted with ether. The extract was concentrated under a reduced pressure and the residue was recrystallized from a mixture of benzene-cyclohexane to obtain 0.72 g. of Compound No. 10 shown in Table 1.

EXAMPLE 5

Production of N-[4-bromo-3-(1-carboxyethyloxy)phenyl]-3,4,5,6-tetrahydrophthalimide A mixture of 4.7 g. of N-[4-bromo-3-(1-ethoxycarbonylethyloxy)phenyl]-3,4,5,6-tetrahydrophthalimide, 15 ml. of methanol and 4 ml. of 40% aqueous solution of sodium hydroxide was refluxed with stirring for 1 hour and the solvent was distilled off under a reduced pressure. The residue was mixed with 0.4 g. of cyclohexane-1,2-dicarboxylic anhydride and 20 ml. of glacial acetic acid and the mixture was refluxed with stirring for 3 hours and the reaction mixture was poured into 1 liter of water to precipitate the product. The precipitate was separated by a filtration and washed with water and dried. The residue was purified by a chromatography on a column of silica gel (developing solvent: ethyl acetate:n-hexane of 8:1) to obtain 3.8 g. of Compound No. 10 shown in Table 1.

EXAMPLE 6

Production of N-(4-bromo-3-methoxycarbonylmethyloxy)phenyl-3,4,5,6-tetrahydrophthalimide A mixture of 1.5 g. of N-(4-bromo-3-carboxymethyloxy)phenyl-3,4,5,6-tetrahydrophthalimide and 15 ml. of methanol was stirred at room temperature and HCl gas was bubbled for 0.5 hour and the solvent was distilled off and the residue was recrystallized from cyclohexane to obtain 1.5 g. of Compound No. 2 shown in Table 1.

EXAMPLE 7

Production of N-[4-bromo-3-(1-propylmercaptocarbonylpropyloxy)-phenyl]-3,4,5,6-tetrahydrophthalimide A mixture of 2.0 g. of N-[4-bromo-3-(1-carboxypropyloxy)phenyl]-3,4,5,6-tetrahydrophthalimide and 2.5 ml. of thionyl chloride was refluxed for 1.5 hours and excess thionyl chloride was distilled off and the residue was dissolved in 10 ml. of toluene. The solution was admixed with a solution of 0.45 g. of 1-propanethiol and 0.60 g. of triethylamine in 5 ml. of toluene and the mixture was stirred at room temperature for 2 hours and then refluxed with stirring for 0.5 hour. The reaction mixture was cooled to room temperature and the precipitate was separated by a filtration and the filtrate was concentrated under a reduced pressure. The resulting oily product was purified by a chromatography on a column of silica gel (developing solvent: ethyl acetate:n-hexane of 1:4) to obtain 2.26 g. of Compound No. 65 shown in Table 1.

EXAMPLE 8

Production of N-[4-bromo-3-(1-phenacyloxycarbonylbutyloxy)-phenyl]-3,4,5,6-tetrahydrophthalimide A mixture of 2.11 g. of N-[4-bromo-3-(1-carboxybutyloxy)phenyl]-3,4,5,6-tetrahydrophthalimide, 11.19 g. of phenacyl bromide, 0.64 g. of potassium fluoride and 10 ml. of acetonitrile was refluxed with stirring for 8.5 hours and the reaction mixture was cooled and the precipitate was separated by a filtration. The filtrate was concentrated under a reduced pressure and the residue was purified by a chromatography on a column of silica gel (developing solvent of benzene) to obtain 2.20 g. of Compound No. 141 shown in Table 1.

EXAMPLE 9

Production of N-[4-bromo-3-(1-methoxycarbonylethyloxy)phenyl]-3,4,5,6-tetrahydrophthalimide A solution of 2.5 g. of N-[4-bromo-3-(1-ethoxycarbonylethyloxy)phenyl]-3,4,5,6-tetrahydrophthalimide in 30 ml. of methanol was prepared and HCl gas was bubbled at room temperature for 0.5 hour and then, the reaction mixture was kept for one night. The precipitate was separated by a filtration and washed with methanol to obtain 2.21 g. of Compound No. 16 shown in Table 1.

EXAMPLE 10

Production of N-[4-chloro-3-(1-ethoxycarbonylpropen-1-yloxy)-phenyl]-3,4,5,6-tetrahydrophthalimide A mixture of 4.0 g. of N-(4-chloro-3-hydroxyphenyl)-3,4,5,6-tetrahydrophthalimide, 4.7 g. of ethyl 2,3-dibromobutyrate, 2.4 g. of potassium carbonate and 35 ml. of acetone was refluxed with stirring for 6 hours and the precipitated salt was separated by a filtration. The filtrate was concentrated under a reduced pressure and 2N-HCl was added to the residue to obtain a crude crystal. The product was washed with water and dried and purified by a chromatography on a column of silica gel (developing solvent: ethyl acetate:n-hexane of 3:7) to obtain 5.2 g. of Compound No. 158 shown in Table 1.

EXAMPLE 11

Production of sodium salt of N-[4-bromo-3-(1-carboxybutyloxy)phenyl]-3,4,5,6-tetrahydrophthalimide To a solution of 2.11 g. of N-[4-bromo-3-(1-carboxybutyloxy)phenyl]-3,4,5,6-tetrahyrophthalimide in 20 ml. of anhydrous benzene, 0.12 g. of sodium hydride was added. After generation of hydrogen was ceased, the solvent was distilled off to obtain 2.18 g. of Compound No. 84 shown in Table 1.

EXAMPLE 12

Production of diisopropylamine salt of N-[4-chloro-3-(1-carboxylpentyloxy)phenyl]-3,4,5,6-tetrahydrophthalimide A mixture of 1.18 g. of N-[4-chloro-3-(1-carboxypentyloxy)phenyl]-3,4,5,6-tetrahydrophthalimide, 0.33 g. of diisopropylamine and 8 ml. of benzene was heated at 80° C. for 5 minutes and kept at room temperature for one night. The precipitate was separated by a filtration to obtain 1.15 g. of Compound No. 171 shown in Table 1.

EXAMPLE 13

Production of N-[4-bromo-3-cyanomethoxyphenyl]-3,4,5,6-tetrahydrophthalimide

A mixture of 1.0 g. of chloroacetonitrile, 2.2 g. of potassium iodide and 25 ml. of acetone was stirred at room temperature for 1 hour and then, 3.5 g. of N-(4- bromo-3-hydroxyphenyl)-3,4,5,6-tetrahydrophthalimide and 1.8 g. of potassium carbonate were added and the mixture was refluxed with stirring for 5 hours. The solvent was distilled off under a reduced pressure and 2N-HCl was added to the residue to precipitate the product. The precipitate was separated by a filtration and washed with water and dried and recrystallized from ethanol to obtain 2.7 g. of Compound No. 229 shown in Table 1.

Compounds Nos. 227, 228 and 230 to 238 were respectively produced by the similar process.

EXAMPLE 14

Production of
N-[4-chloro-3-cyanomethoxyphenyl]-3,4,5,6-tetrahydrophthalimide

A mixture of 1.52 g. of cyclohexane-1,2-dicarboxylic anhydride, 1.83 g. of 4-chloro-3-cyanomethoxyaniline (melting point 89°–90° C.) and 8 ml. of acetic acid was refluxed with stirring for 2.5 hours. The solvent was distilled off under a reduced pressure and then, water was added to obtain a crude crystal. The product was recrystallized from methanol to obtain 2.83 g. of Compound No. 228 shown in Table 1.

EXAMPLE 15

Production of
N-[[4-chloro-3-[1-(propylcarbamoyl)propoxy]phenyl]]-3,4,5,6-tetrahydrophthalimide A mixture of 2.00 g. of N-[4-chloro-3-(1-carboxypropoxy)phenyl]-3,4,5,6-tetrahydrophthalimide and 5 ml. of thionyl chloride was refluxed with stirring for 1 hour and excess thionyl chloride was distilled off under a reduced pressure. The product was dissolved in 10 ml. of toluene and a mixture of 0.36 g. of n-propylamine, 0.6 g. of triethylamine and 5 ml. of toluene was added and the mixture was stirred at room temperature for 2 hours. Chloroform was added and the resulting organic phase was washed with water and dried and the product was purified by a chromatography on a column of silica gel (developing solvent:chloroform) and recrystallized from a mixture of ethyl acetate and n-hexane to obtain 1.62 g. of Compound No. 286 shown in Table 1.

Compounds Nos. 239, 244, 246, 248 to 256, 258, 262, 267, 271, 273, 275 to 277, 281, 283, 287 to 290. 292, 293, 295, 296, 298, 299, 301, 305 to 312, 317, 321, 324 to 326, 329 to 332 and 234 were respectively produced by the similar process.

EXAMPLE 16

Production of
N-[[4-chloro-3-[1-(dimethylcarbamoyl)propoxy]-phenyl]]-3,4,5,6-tetrahydrophthalimide A mixture of 2.0 g. of N-[4-chloro-3-(1-carboxypropoxy)phenyl]-3,4,5,6-tetrahydrophthalimide and 5 ml. of thionyl chloride was refluxed with stirring for 1 hour and excess thionyl chloride was distilled off under a reduced pressure. The residue was dissolved in 10 ml. of tetrahydrofuran and a mixture of 0.55 g. of 50% aqueous solution of dimethylamine, 0.6 g. of triethylamine and 5 ml. of tetrahydrofuran was added and the mixture was stirred at room temperature for 2 hours. Chloroform was added and the resulting organic phase was washed with water and dried and the residue was purified by a chromatography on a column of silica gel (developing solvent of chloroform) and recrystallized from a mixture of ethyl acetate and n-hexane to obtain 1.39 g. of Compound No. 297 shown in Table 1.

Compounds Nos. 263 to 265, 268, 270, 278, 300, 314, 327 and 328 were respectively produced by the similar process.

EXAMPLE 17

Production of
N-[[4-chloro-3-[1-(dimethylcarbamoyl)butoxy]-phenyl]]-3,4,5,6-tetrahydrophthalimide A mixture of 2.20 g. of N-[4-chloro-3-(1-carboxybutoxy)phenyl]-3,4,5,6-tetrahydrophthalimide and 5 ml. of thionyl chloride was refluxed with stirring for 1 hour and excess thionyl chloride was distilled off under a reduced pressure. The residue was dissolved in 10 ml. of tetrahydrofuran and a mixture of 1.3 g. of 50% aqueous solution of dimethylamine and 5 ml. of tetrahydrofuran was added and the resulting organic phase was washed with water and dried. The residue was purified by a chromatography on a column of silica gel (developing solvent of chloroform) and recrystallized from a mixture of ethyl acetate and n-hexane to obtain 1.33 g. of Compound No. 313 shown in Table 1.

Compounds Nos. 241, 243, 269, 284, 285, 302, 304, 315, 316, 322 and 323 were respectively produced by the similar process.

EXAMPLE 18

Production of
N-[[4-chloro-3-[1-(tosylcarbamoyl)pentyloxy]phenyl]]-3,4,5,6-tetrahydrophthalimide A mixture of 1.57 g. of N-[4-chloro-3-(1-carboxypentyloxy)phenyl]-3,4,5,6-tetrahydrophthalimide and 4 ml. of thionyl chloride was refluxed with stirring for 1 hour and excess thionyl chloride was distilled off under a reduced pressure. The residue was dissolved in 5 ml. of tetrahydrofuran and a mixture of 0.82 g. of p-toluenesulfonamide 0.23 g. of 50% sodium hydride and 10 ml. of tetrahydrofuran was added and the mixture was stirred at room temperature for 1 hour. Benzene was added and the resulting organic phase was washed with water and dried. The residue was purified by a chromatography on a column of silica gel (developing solvent of chloroform) and recrystallized from a mixture of ethyl acetate and n-hexane to obtain 1.28 g. of Compound No. 335 shown in Table 1.

Compounds Nos. 279, 280 and 333 were respectively produced by the similar process.

EXAMPLE 19

Production of
N-[[4-chloro-3-[1-(phenylcarbamoyl)propoxy]phenyl]]-3,4,5,6-tetrahydrophthalimide A mixture of 1.52 g. of cyclohexane-1,2-dicarboxylic anhydride, 3.05 g. of N-phenyl-α-(5-amino-2-chlorophenoxy)butyramide (melting point of 78° to 80° C.) and 10 ml. of acetic acid was refluxed with stirring for 2 hours and the reaction mixture was cooled to room temperature and water was added to obtain a crude crystal. The product was recrystallized from a mixture of ethyl acetate and n-hexane to obtain 3.86 g. of Compound No. 294 shown in Table 1.

EXAMPLE 20

Production of N-[[4-chloro-3-[1-(ethylcarbamoyl)ethoxy]phenyl]]-3,4,5,6-tetrahydrophthalimide (i) Production of ethyl α-(2-chloro-5-nitrophenoxy)propionate A mixture of 17.4 g. of 2-chloro-5-nitrophenol, 19.0 g. of ethyl α-bromopropionate, 15.2 g. of potassium carbonate and 85 ml. of acetone was refluxed with stirring for 3.5 hours and the solvent was distilled off. 2N-HCl was added to the residue to obtain a crude crystal. The product was separated by a filtration and washed with water and dried and recrystallized from n-hexane to obtain 27.4 g. of the object compound (melting point of 46° to 46.5° C.).

(ii) Production of N-ethyl α-(2-chloro-5-nitrophenoxy)propionamide

A mixture of 2.74 g. of ethyl α-(2-chloro-5-nitrophenoxy)propionate, 0.77 g. of 70% aqueous solution of ethylamine and 15 ml. of ethanol was kept at room temperature for one night. The precipitate was separated by a filtration and recrystallized from a mixture of benzene-cyclohexane to obtain 2.5 g. of the object compound (melting point of 148° to 149° C.).

(iii) Production of N-[[4-chloro-3-[1-(ethylcarbamoyl)ethoxy]phenyl]]-3,4,5,6-tetrahydrophthalimide In 15 ml. glacial acetic acid, 1.5 g. of N-ethyl-α-(2-chloro-5-nitrophenoxy)propionamide was reduced in the presence of a catalyst of 5% Pd/C. The catalyst was separated by a filtration. To the resulting N-ethyl-α-(5-amino-2-chlorophenoxy)propionamide, 0.83 g. of cyclohexane-1,2-dicarboxylic anhydride was added and the mixture was refluxed with stirring for 2 hours.

The reaction mixture was cooled to room temperature and water was added to obtain a crude crystal. The product was recrystallized from isopropanol to obtain 1.4 g. of Compound 242 shown in Table 1.

Compound No. 240 was produced by the similar process.

EXAMPLE 21

Production of N-[[4-bromo-3-[1-(diallylcarbamoyl)ethoxy]phenyl]]-3,4,5,6-tetrahydrophthalimide A mixture of 8.5 g. of α-bromopropionyl chloride, 4.0 g. of sodium bicarbonate and 40 ml. of ether was cooled with ice and a solution of 4.0 g. of diallylamine in 10 ml. of ether was added dropwise and the mixture was stirred at room temperature for 1 hour.

The reaction mixture was washed with water and dried and the solvent was distilled off to obtain 3.8 g. of N,N-diallyl α-bromopropionamide. The product was admixed with 3.5 g. of N-(4-bromo-3-hydroxyphenyl)-3,4,5,6-tetrahydrophthalimide, 2.2 g. of potassium carbonate, 1.8 g. of potassium iodide and 50 ml. of acetone.

The mixture was refluxed with stirring for 3 hours. The resulting salt was separated by a filtration. The filtrate was distilled off under a reduced pressure. The residue was purified by a chromatography on a column of silica gel (developing solvent: ethyl acetate:n-hexane of 1:1) to obtain 2.8 g. of Compound No. 274 shown in Table 1.

Compounds Nos. 247 and 266 were respectively produced by the similar process.

The structures of all of the compounds shown in Table 1 were confirmed by IR spectrum and/or ¹H-NMR spectrum.

TABLE 1

| | X | Y | —O—A—B | m.p. or $n_D$ |
|---|---|---|---|---|
| 1 | Br | H | —O—CH$_2$—COOH | mp 178–179° C. |
| 2 | Br | H | —O—CH$_2$—COOCH$_3$ | mp 140–143° C. |
| 3 | Cl | Cl | —O—CH$_2$—COOCH$_3$ | mp 141–142° C. |
| 4 | Cl | H | —O—CH$_2$—COOC$_2$H$_5$ | mp 105–107° C. |
| 5 | Br | H | —O—CH$_2$—COOC$_2$H$_5$ | mp 105–106° C. |
| 6 | Cl | Cl | —O—CH$_2$—COOC$_2$H$_5$ | mp 119.5–120° C. |
| 7 | Br | H | —O—CH$_2$—COOC$_3$H$_7$—n | mp 83–84° C. |
| 8 | Br | H | —O—CH$_2$—COOCH$_2$CH$_2$OH | mp 89–91° C. |
| 9 | Cl | H | —O—CH(CH$_3$)COOH | mp 171–173° C. |
| 10 | Br | H | —O—CH(CH$_3$)COOH | mp 189–191° C. |
| 11 | Cl | Cl | —O—CH(CH$_3$)COOH | mp 155–156° C. |

TABLE 1-continued

[Structure: tetrahydrophthalimide with N-aryl group bearing O-A-B, X, Y substituents]

| | X | Y | —O—A—B | m.p. or $n_D$ |
|---|---|---|---|---|
| 12 | Br | H | —O—CH(CH₃)—COONa | amorphous solid |
| 13 | Br | H | —O—CH(CH₃)—COOH·H₂NC₃H₇—i | amorphous solid |
| 14 | Br | H | —O—CH(CH₃)—COOH·H₂NC₄H₉—i | amorphous solid |
| 15 | Br | H | —O—CH(CH₃)—COOH·HN(CH₃)₂ | mp 157–162° C. |
| 16 | Br | H | —O—CH(CH₃)—COOCH₃ | mp 138–139° C. |
| 17 | Cl | H | —O—CH(CH₃)—COOC₂H₅ | mp 99–101° C. |
| 18 | Br | H | —O—CH(CH₃)—COOC₂H₅ | mp 109–110° C. |
| 19 | Cl | Cl | —O—CH(CH₃)—COOC₂H₅ | mp 121–122° C. |
| 20 | Cl | H | —O—CH(CH₃)—COSC₂H₅ | mp 64–66° C. |
| 21 | Br | H | —O—CH(CH₃)—COSC₂H₅ | mp 82–84° C. |
| 22 | Cl | H | —O—CH(CH₃)—COOC₃H₇—n | mp 83.5–84° C. |
| 23 | Br | H | —O—CH(CH₃)—COOC₃H₇—n | mp 91–92° C. |
| 24 | Cl | H | —O—CH(CH₃)—COOC₃H₇—i | mp 114–114.5° C. |
| 25 | Br | H | —O—CH(CH₃)—COOC₃H₇—i | mp 108–109° C. |
| 26 | Cl | H | —O—CH(CH₃)—COOC₄H₉—n | mp 49.5–50.5° C. |
| 27 | Br | H | —O—CH(CH₃)—COOC₄H₉—n | mp 67.5–68.5° C. |
| 28 | Br | H | —O—CH(CH₃)—COSC₄H₉—n | mp 64–65° C. |
| 29 | Cl | H | —O—CH(CH₃)—COOC₄H₉—i | $n_D^{15}$ 1.5478 |

TABLE 1-continued

[Structure: 4,5,6,7-tetrahydrophthalimide N-substituted with phenyl ring bearing O-A-B (top), X, and Y substituents]

| | X | Y | —O—A—B | m.p. or $n_D$ |
|---|---|---|---|---|
| 30 | Cl | H | —O—CH(CH$_3$)—COOC$_4$H$_9$-t | mp 103.5–104.5° C. |
| 31 | Br | H | —O—CH(CH$_3$)—COOC$_4$H$_9$-t | mp 108–109° C. |
| 32 | Cl | H | —O—CH(CH$_3$)—COOC$_5$H$_{11}$-n | mp 47.5–49.5° C. |
| 33 | Br | H | —O—CH(CH$_3$)—COOC$_5$H$_{11}$-n | mp 58–59° C. |
| 34 | Br | H | —O—CH(CH$_3$)—COOC$_5$H$_{11}$-t | mp 83–84.5° C. |
| 35 | Cl | H | —O—CH(CH$_3$)—COOC$_6$H$_{13}$-n | mp 57–58° C. |
| 36 | Cl | H | —O—CH(CH$_3$)—COOC$_{11}$H$_{23}$-n | mp 42–43° C. |
| 37 | Br | H | —O—CH(CH$_3$)—COOCH$_2$CN | mp 149–150° C. |
| 38 | Cl | H | —O—CH(CH$_3$)—COO(CH$_2$)$_2$OCH$_3$ | mp 72–72.5° C. |
| 39 | Br | H | —O—CH(CH$_3$)—COO(CH$_2$)$_2$OCH$_3$ | mp 51–53° C. |
| 40 | Cl | H | —O—CH(CH$_3$)—COO(CH$_2$)$_2$OC$_4$H$_9$-n | $n_D^{15}$ 1.5410 |
| 41 | Br | H | —O—CH(CH$_3$)—COO(CH$_2$)$_2$OC$_4$H$_9$-n | $n_D^{15}$ 1.5503 |
| 42 | Cl | H | —O—CH(CH$_3$)—COO(CH$_2$CH$_2$O)$_2$C$_2$H$_5$ | $n_D^{15}$ 1.5400 |
| 43 | Br | H | —O—CH(CH$_3$)—COO(CH$_2$CH$_2$O)$_2$C$_2$H$_5$ | $n_D^{14}$ 1.5492 |
| 44 | Br | H | —O—CH(CH$_3$)—COO(CH$_2$CH$_2$O)$_3$CH$_3$ | $n_D^{25}$ 1.5395 |
| 45 | Cl | H | —O—CH(CH$_3$)—COO—(cyclohexyl) | mp 93–93.5° C. |
| 46 | Cl | H | —O—CH(CH$_3$)—COOCH$_2$—(phenyl) | mp 92–93° C. |
| 47 | Br | H | —O—CH(CH$_3$)—COOCH$_2$—(phenyl) | mp 80–82° C. |

TABLE 1-continued

[Structure: tetrahydrophthalimide N-substituted with phenyl ring bearing O—A—B, X, Y substituents]

| | X | Y | —O—A—B | m.p. or $n_D$ |
|---|---|---|---|---|
| 48 | Br | H | —O—CH(CH$_3$)—COO—CH(CH$_3$)—C$_6$H$_5$ | $n_D^{14}$ 1.5738 |
| 49 | Cl | H | —O—CH(CH$_3$)—COOCH$_2$CH$_2$—C$_6$H$_4$—CH$_3$ | mp 85–85.5° C. |
| 50 | Br | H | —O—CH(CH$_3$)—COO—C$_6$H$_5$ | mp 117–119° C. |
| 51 | Br | H | —O—CH(CH$_3$)—COOCH$_2$CO—C$_6$H$_5$ | mp 159–159.5° C. |
| 52 | Br | H | —O—C(CH$_3$)$_2$—COOH | mp 159–160° C. |
| 53 | Br | H | —O—C(CH$_3$)$_2$—COOC$_2$H$_5$ | mp 94–95° C. |
| 54 | Cl | Cl | —O—C(CH$_3$)$_2$—COOC$_2$H$_5$ | mp 109–110° C. |
| 55 | Cl | H | —O—CH(C$_2$H$_5$)—COOH | mp 157–159° C. |
| 56 | Br | H | —O—CH(C$_2$H$_5$)—COOH | mp 173–174° C. |
| 57 | Br | H | —O—CH(C$_2$H$_5$)—COOCH$_3$ | mp 107–108° C. |
| 58 | Cl | H | —O—CH(C$_2$H$_5$)—COOC$_2$H$_5$ | mp 78–79° C. |
| 59 | Br | H | —O—CH(C$_2$H$_5$)—COOC$_2$H$_5$ | mp 58–60° C. |
| 60 | Cl | H | —O—CH(C$_2$H$_5$)—COSC$_2$H$_5$ | mp 70–73° C. |
| 61 | Br | H | —O—CH(C$_2$H$_5$)—COSC$_2$H$_5$ | mp 92–95° C. |
| 62 | Cl | H | —O—CH(C$_2$H$_5$)—COOC$_3$H$_7$-n | mp 55–56° C. |
| 63 | Br | H | —O—CH(C$_2$H$_5$)—COOC$_3$H$_7$-n | mp 63–64° C. |
| 64 | Cl | H | —O—CH(C$_2$H$_5$)—COSC$_3$H$_7$-n | $n_D^{27}$ 1.5703 |
| 65 | Br | H | —O—CH(C$_2$H$_5$)—COSC$_3$H$_7$-n | mp 65–66° C. |

TABLE 1-continued

[Structure: tetrahydrophthalimide N-substituted with phenyl ring bearing O-A-B, X, and Y substituents]

| | X | Y | —O—A—B | m.p. or $n_D$ |
|---|---|---|---|---|
| 66 | Cl | H | —O—CH(C$_2$H$_5$)—COOC$_4$H$_9$—n | mp 50–51° C. |
| 67 | Br | H | —O—CH(C$_2$H$_5$)—COOC$_4$H$_9$—n | mp 77.5–78.5° C. |
| 68 | Cl | H | —O—CH(C$_2$H$_5$)—COSC$_4$H$_9$—n | $n_D^{22}$ 1.5613 |
| 69 | Cl | H | —O—CH(C$_2$H$_5$)—COOC$_5$H$_{11}$—n | mp 49–50° C. |
| 70 | Br | H | —O—CH(C$_2$H$_5$)—COOC$_5$H$_{11}$—n | mp 52–53.5° C. |
| 71 | Br | H | —O—CH(C$_2$H$_5$)—COOCH$_2$CH$_2$F | mp 55–57° C. |
| 72 | Cl | H | —O—CH(C$_2$H$_5$)—COOCH$_2$CF$_3$ | $n_D^{24.5}$ 1.5225 |
| 73 | Br | H | —O—CH(C$_2$H$_5$)—COOCH$_2$CF$_2$CHF$_2$ | mp 60–61° C. |
| 74 | Cl | H | —O—CH(C$_2$H$_5$)—COO(CH$_2$)$_2$OCH$_3$ | $n_D^{25}$ 1.5410 |
| 75 | Br | H | —O—CH(C$_2$H$_5$)—COO(CH$_2$CH$_2$O)$_2$C$_3$H$_7$—n | $n_D^{25}$ 1.5330 |
| 76 | Cl | H | —O—CH(C$_2$H$_5$)—COO(CH$_2$)$_2$SC$_2$H$_5$ | mp 47.5–48.5° C. |
| 77 | Br | H | —O—CH(C$_2$H$_5$)—COO—cyclopentyl | mp 89–92° C. |
| 78 | Br | H | —O—CH(C$_2$H$_5$)—COOCH$_2$COCH$_3$ | amorphous solid |
| 79 | Cl | H | —O—CH(C$_2$H$_5$)—COOCH$_2$CH(CH$_3$)COCH$_3$ | mp 95.5–97° C. |
| 80 | Br | H | —O—CH(C$_2$H$_5$)—COOCH$_2$CH(CH$_3$)COCH$_3$ | mp 92–94° C. |
| 81 | Br | H | —O—CH(C$_2$H$_5$)—COOCH$_2$CO—C$_6$H$_5$ | mp 157.5–158° C. |
| 82 | Cl | H | —O—CH(C$_3$H$_7$—n)—COOH | mp 134.5–136° C. |
| 83 | Br | H | —O—CH(C$_3$H$_7$—n)—COOH | mp 136–137° C. |

TABLE 1-continued

[Structure: tetrahydrophthalimide with N-aryl group bearing O-A-B and X, Y substituents]

| | X | Y | —O—A—B | m.p. or $n_D$ |
|---|---|---|---|---|
| 84 | Br | H | —O—CH(C$_3$H$_7$-n)—COONa | amorphous solid |
| 85 | Br | H | —O—CH(C$_3$H$_7$-n)—COOH·H$_2$NC$_3$H$_7$-n | amorphous solid |
| 86 | Br | H | —O—CH(C$_3$H$_7$-n)—COOH·H$_2$NC$_4$H$_9$-s | amorphous solid |
| 87 | Cl | H | —O—CH(C$_3$H$_7$-n)—COOCH$_3$ | mp 72.5–74.5° C. |
| 88 | Br | H | —O—CH(C$_3$H$_7$-n)—COOCH$_3$ | mp 79–81° C. |
| 89 | Cl | H | —O—CH(C$_3$H$_7$-n)—COOC$_2$H$_5$ | mp 91.5–93.5° C. |
| 90 | Br | H | —O—CH(C$_3$H$_7$-n)—COOC$_2$H$_5$ | mp 104–105° C. |
| 91 | Cl | H | —O—CH(C$_3$H$_7$-n)—COSC$_2$H$_5$ | mp 67–70° C. |
| 92 | Br | H | —O—CH(C$_3$H$_7$-n)—COSC$_2$H$_5$ | mp 66–67° C. |
| 93 | Cl | H | —O—CH(C$_3$H$_7$-n)—COOC$_3$H$_7$-n | mp 66–68° C. |
| 94 | Br | H | —O—CH(C$_3$H$_7$-n)—COOC$_3$H$_7$-n | mp 81.5–83° C. |
| 95 | Cl | H | —O—CH(C$_3$H$_7$-n)—COSC$_3$H$_7$-n | mp 79–83° C. |
| 96 | Br | H | —O—CH(C$_3$H$_7$-n)—COSC$_3$H$_7$-n | mp 70–72° C. |
| 97 | Cl | H | —O—CH(C$_3$H$_7$-n)—COOC$_3$H$_7$-i | mp 78–79° C. |
| 98 | Br | H | —O—CH(C$_3$H$_7$-n)—COOC$_3$H$_7$-i | mp 79–80° C. |
| 99 | Cl | H | —O—CH(C$_3$H$_7$-n)—COOC$_4$H$_9$-n | mp 46.5–48° C. |
| 100 | Br | H | —O—CH(C$_3$H$_7$-n)—COOC$_4$H$_9$-n | mp 49.5–51.5° C. |

TABLE 1-continued

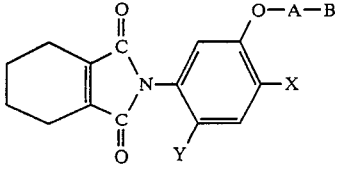

| | X | Y | —O—A—B | m.p. or $n_D$ |
|---|---|---|---|---|
| 101 | Cl | H | —O—CH(C$_3$H$_7$-n)—COOC$_5$H$_{11}$-n | $n_D^{26.5}$ 1.5225 |
| 102 | Br | H | —O—CH(C$_3$H$_7$-n)—COOC$_5$H$_{11}$-n | $n_D^{26.5}$ 1.5171 |
| 103 | Cl | H | —O—CH(C$_3$H$_7$-n)—COOC$_6$H$_{13}$-n | $n_D^{26.5}$ 1.5231 |
| 104 | Br | H | —O—CH(C$_3$H$_7$-n)—COOC$_6$H$_{13}$-n | $n_D^{26.5}$ 1.5250 |
| 105 | Cl | H | —O—CH(C$_3$H$_7$-n)—COSC$_{10}$H$_{21}$-n | $n_D^{22}$ 1.5402 |
| 106 | Cl | H | —O—CH(C$_3$H$_7$-n)—COOCH$_2$CH=CH$_2$ | mp 58–59.5° C. |
| 107 | Br | H | —O—CH(C$_3$H$_7$-n)—COOCH$_2$CH=CH$_2$ | mp 52.5–55.5° C. |
| 108 | Cl | H | —O—CH(C$_3$H$_7$-n)—COOCH$_2$C≡CH | $n_D^{28}$ 1.5485 |
| 109 | Br | H | —O—CH(C$_3$H$_7$-n)—COOCH$_2$C≡CH | $n_D^{28}$ 1.5471 |
| 110 | Br | H | —O—CH(C$_3$H$_7$-n)—COOCH$_2$CH$_2$F | mp 66–68° C. |
| 111 | Cl | H | —O—CH(C$_3$H$_7$-n)—COOCH$_2$CH$_2$Cl | $n_D^{21}$ 1.5502 |
| 112 | Br | H | —O—CH(C$_3$H$_7$-n)—COOCH$_2$CH$_2$Cl | $n_D^{21}$ 1.5582 |
| 113 | Cl | H | —O—CH(C$_3$H$_7$-n)—COOCH$_2$CH$_2$Br | mp 83–85° C. |
| 114 | Br | H | —O—CH(C$_3$H$_7$-n)—COOCH$_2$CH$_2$Br | mp 65–67° C. |
| 115 | Cl | H | —O—CH(C$_3$H$_7$-n)—COOCH$_2$CCl$_3$ | mp 66.5–69° C. |
| 116 | Br | H | —O—CH(C$_3$H$_7$-n)—COOCH$_2$CCl$_3$ | mp 61.5–63° C. |
| 117 | Cl | H | —O—CH(C$_3$H$_7$-n)—COO(CH$_2$)$_3$Cl | mp 61.5–63° C. |

TABLE 1-continued

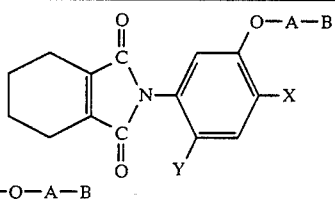

| | X | Y | —O—A—B | m.p. or $n_D$ |
|---|---|---|---|---|
| 118 | Br | H | —O—CH(C$_3$H$_7$-n)—COO(CH$_2$)$_3$Cl | mp 70.5–72° C. |
| 119 | Cl | H | —O—CH(C$_3$H$_7$-n)—COO(CH$_2$)$_3$Br | mp 75.5–76.5° C. |
| 120 | Br | H | —O—CH(C$_3$H$_7$-n)—COO(CH$_2$)$_3$Br | mp 76–78° C. |
| 121 | Cl | H | —O—CH(C$_3$H$_7$-n)—COOCH$_2$CHClCH$_2$Cl | mp 83.5–86° C. |
| 122 | Br | H | —O—CH(C$_3$H$_7$-n)—COOCH$_2$CHClCH$_2$Cl | mp 83–86° C. |
| 123 | Cl | H | —O—CH(C$_3$H$_7$-n)—COOCH$_2$CHBrCH$_2$Br | mp 69–72° C. |
| 124 | Br | H | —O—CH(C$_3$H$_7$-n)—COOCH$_2$CHBrCH$_2$Br | mp 71–73.5° C. |
| 125 | Br | H | —O—CH(C$_3$H$_7$-n)—COOCH$_2$CF$_2$CHF$_2$ | $n_D^{24.5}$ 1.5220 |
| 126 | Br | H | —O—CH(C$_3$H$_7$-n)—COOCH$_2$CCl=CCl$_2$ | $n_D^{25.5}$ 1.5560 |
| 127 | Br | H | —O—CH(C$_3$H$_7$-n)—COO(CH$_2$)$_2$OC$_4$H$_9$-n | $n_D^{25}$ 1.5435 |
| 128 | Br | H | —O—CH(C$_3$H$_7$-n)—COO(CH$_2$CH$_2$O)$_3$CH$_3$ | $n_D^{25}$ 1.5445 |
| 129 | Br | H | —O—CH(C$_3$H$_7$-n)—COO(CH$_2$)$_2$SC$_2$H$_5$ | mp 91–92° C. |
| 130 | Br | H | —O—CH(C$_3$H$_7$-n)—COO(CH$_2$)$_2$S—C$_4$H$_9$-n | mp 51–52° C. |
| 131 | Br | H | —O—CH(C$_3$H$_7$-n)—COO-cyclopentyl | mp 94.5–95.5° C. |
| 132 | Cl | H | —O—CH(C$_3$H$_7$-n)—COO-cyclohexyl | mp 104–107° C. |
| 133 | Br | H | —O—CH(C$_3$H$_7$-n)—COO-cyclohexyl | mp 112–114° C. |
| 134 | Cl | H | —O—CH(C$_3$H$_7$-n)—COOCH$_2$-phenyl | mp 84–87° C. |

TABLE 1-continued

| | X | Y | —O—A—B | m.p. or $n_D$ |
|---|---|---|---|---|
| 135 | Br | H | —O—CH(C$_3$H$_7$-n)—COOCH$_2$—C$_6$H$_5$ | mp 89–92° C. |
| 136 | Cl | H | —O—CH(C$_3$H$_7$-n)—COOCH$_2$—C$_6$H$_4$—Cl | mp 105–107° C. |
| 137 | Br | H | —O—CH(C$_3$H$_7$-n)—COOCH$_2$—C$_6$H$_4$—Cl | mp 97–99° C. |
| 138 | Br | H | —O—CH(C$_3$H$_7$-n)—COOCH(CH$_3$)COCH$_3$ | amorphous solid |
| 139 | Br | H | —O—CH(C$_3$H$_7$-n)—COOCH$_2$CH(CH$_3$)COCH$_3$ | mp 101–102.5° C. |
| 140 | Br | H | —O—CH(C$_3$H$_7$-n)—COO(CH$_2$)$_3$COCH$_3$ | $n_D^{24.5}$ 1.5551 |
| 141 | Br | H | —O—CH(C$_3$H$_7$-n)—COOCH$_2$CO—C$_6$H$_5$ | mp 130.5–131° C. |
| 142 | Br | H | —O—CH(C$_3$H$_7$-n)—COSCH$_2$COOC$_2$H$_5$ | $n_D^{22}$ 1.5464 |
| 143 | Cl | H | —O—CH(C$_3$H$_7$-i)—COOH | mp 173–174° C. |
| 144 | Br | H | —O—CH(C$_3$H$_7$-i)—COOH | mp 188–190° C. |
| 145 | Br | H | —O—CH(C$_3$H$_7$-i)—COOC$_2$H$_5$ | mp 100–101° C. |
| 146 | Cl | H | —O—CH(C$_3$H$_7$-i)—COOC$_3$H$_7$-n | mp 68–70° C. |
| 147 | Br | H | —O—CH(C$_3$H$_7$-i)—COOC$_3$H$_7$-n | mp 69–71.5° C. |
| 148 | Cl | H | —O—CH(C$_3$H$_7$-i)—COOC$_3$H$_7$-i | mp 67.5–69° C. |
| 149 | Br | H | —O—CH(C$_3$H$_7$-i)—COOC$_3$H$_7$-i | mp 58–60° C. |
| 150 | Cl | H | —O—CH(C$_3$H$_7$-i)—COOC$_4$H$_9$-n | $n_D^{27}$ 1.5359 |

TABLE 1-continued

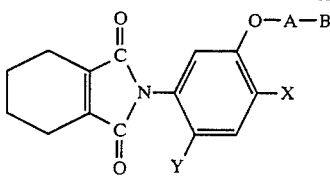

| | X | Y | —O—A—B | m.p. or $n_D$ |
|---|---|---|---|---|
| 151 | Br | H | —O—CH(C$_3$H$_7$—i)—COOC$_4$H$_9$—n | $n_D^{27.5}$ 1.5424 |
| 152 | Cl | H | —O—CH(C$_3$H$_7$—i)—COOC$_5$H$_{11}$—n | $n_D^{27}$ 1.5241 |
| 153 | Br | H | —O—CH(C$_3$H$_7$—i)—COOC$_5$H$_{11}$—n | $n_D^{27.5}$ 1.5423 |
| 154 | Cl | H | —O—CH(C$_3$H$_7$—i)—COOC$_6$H$_{13}$—n | $n_D^{28}$ 1.5248 |
| 155 | Br | H | —O—CH(C$_3$H$_7$—i)—COOC$_6$H$_{13}$—n | $n_D^{28}$ 1.5360 |
| 156 | Cl | H | —O—CH(C$_3$H$_7$—i)—COOCH$_2$CH=CH$_2$ | $n_D^{25}$ 1.5518 |
| 157 | Br | H | —O—CH(C$_3$H$_7$—i)—COOCH$_2$CH=CH$_2$ | $n_D^{25}$ 1.5583 |
| 158 | Cl | H | —O—C(=CHCH$_3$)—COOC$_2$H$_5$ | $n_D^{27}$ 1.5653 |
| 159 | Br | H | —O—C(=CHCH$_3$)—COOC$_2$H$_5$ | mp 68–76° C. |
| 160 | Cl | H | —O—CH$_2$CH$_2$—CH$_2$COOH | mp 154–157° C. |
| 161 | Br | H | —O—CH$_2$CH$_2$CH$_2$COOH | mp 156–158° C. |
| 162 | Cl | H | —O—CH$_2$CH$_2$CH$_2$—COOC$_2$H$_5$ | mp 74–76° C. |
| 163 | Br | H | —O—CH$_2$CH$_2$CH$_2$—COOC$_2$H$_5$ | mp 79–80° C. |
| 164 | Cl | Cl | —O—CH$_2$CH$_2$CH$_2$—COOC$_2$H$_5$ | mp 94–95° C. |
| 165 | Br | H | —O—CH$_2$CH=CH—COOH | mp 145–148° C. |
| 166 | Cl | H | —O—CH$_2$CH=CHCOOC$_2$H$_5$ | mp 110–111° C. |
| 167 | Br | H | —O—CH$_2$CH=CH—COOC$_2$H$_5$ | mp 121–122° C. |
| 168 | Cl | Cl | —O—CH$_2$CH=CHCOOC$_2$H$_5$ | mp 154–156° C. |
| 169 | Cl | H | —O—CH(C$_4$H$_9$—n)COOH | mp 102–104.5° C. |
| 170 | Br | H | —O—CH(C$_4$H$_9$—n)—COOH | mp 106–110° C. |
| 171 | Cl | H | —O—CH(C$_4$H$_9$—n)—COOH.HN(C$_3$H$_7$—i)$_2$ | mp 147–151° C. |
| 172 | Cl | H | —O—CH(C$_4$H$_9$—n)—COOH.N(C$_2$H$_5$)$_3$ | amorphous solid |

TABLE 1-continued

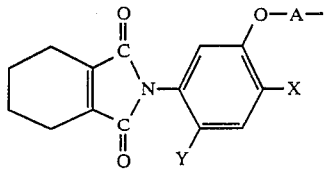

| | X | Y | —O—A—B | m.p. or $n_D$ |
|---|---|---|---|---|
| 173 | Cl | H | —O—CH(C$_4$H$_9$—n)—COOCH$_3$ | $n_D^{28}$ 1.5479 |
| 174 | Br | H | —O—CH(C$_4$H$_9$—n)—COOCH$_3$ | $n_D^{28}$ 1.5573 |
| 175 | Cl | H | —O—CH(C$_4$H$_9$—n)—COOC$_2$H$_5$ | mp 77–78° C. |
| 176 | Br | H | —O—CH(C$_4$H$_9$—n)—COOC$_2$H$_5$ | mp 97–98° C. |
| 177 | Br | H | —O—CH(C$_4$H$_9$—n)—COSC$_2$H$_5$ | $n_D^{22}$ 1.5700 |
| 178 | Cl | H | —O—CH(C$_4$H$_9$—n)—COOC$_3$H$_7$—n | mp 61.5–63° C. |
| 179 | Br | H | —O—CH(C$_4$H$_9$—n)—COOC$_3$H$_7$—n | mp 79.5–82° C. |
| 180 | Cl | H | —O—CH(C$_4$H$_9$—n)—COOC$_4$H$_9$—n | mp 55.5–57° C. |
| 181 | Br | H | —O—CH(C$_4$H$_9$—n)—COOC$_4$H$_9$—n | mp 63.5–65.5° C. |
| 182 | Cl | H | —O—CH(C$_4$H$_9$—n)—COOC$_4$H$_9$—i | $n_D^{28}$ 1.5305 |
| 183 | Br | H | —O—CH(C$_4$H$_9$—n)—COOC$_4$H$_9$—i | $n_D^{28}$ 1.5398 |
| 184 | Cl | H | —O—CH(C$_4$H$_9$—n)—COOC$_5$H$_{11}$—n | $n_D^{28}$ 1.5285 |
| 185 | Br | H | —O—CH(C$_4$H$_9$—n)—COOC$_5$H$_{11}$—n | $n_D^{28}$ 1.5376 |
| 186 | Br | H | —o—CH(C$_4$H$_9$—n)—COSC$_5$H$_{11}$—sec | $n_D^{22}$ 1.5590 |
| 187 | Br | H | —O—CH(C$_4$H$_9$—n)—COOCH$_2$CH$_2$F | mp 68.5–71° C. |
| 188 | Br | H | —O—CH(C$_4$H$_9$—n)—COOCH$_2$COCH$_3$ | mp 75–76° C. |
| 189 | Cl | H | —O—CH(C$_6$H$_{13}$—n)—COOC$_2$H$_5$ | $n_D^{14}$ 1.5305 |

TABLE 1-continued

[Structure: tetrahydrophthalimide substituted phenyl with O-A-B, X, Y substituents]

| | X | Y | —O—A—B | m.p. or $n_D$ |
|---|---|---|---|---|
| 190 | Br | H | —O—CH(C$_6$H$_{13}$-n)—COOC$_2$H$_5$ | $n_D^{14}$ 1.5413 |
| 191 | Cl | H | —O—CH(COOH)—C$_6$H$_5$ | mp 175.5–178° C. |
| 192 | Br | H | —O—CH(COOH)—C$_6$H$_5$ | mp 174–176° C. |
| 193 | Br | H | —O—CH(COOCH$_3$)—C$_6$H$_5$ | mp 139–139.5° C. |
| 194 | Cl | H | —O—CH(COOC$_2$H$_5$)—C$_6$H$_5$ | mp 97–98° C. |
| 195 | Br | H | —O—CH(COOC$_2$H$_5$)—C$_6$H$_5$ | mp 116–119° C. |
| 196 | Cl | H | —O—CH(COOC$_3$H$_7$-n)—C$_6$H$_5$ | mp 100.5–103° C. |
| 197 | Br | H | —O—CH(COOC$_3$H$_7$-n)—C$_6$H$_5$ | mp 82–82.5° C. |
| 198 | Cl | H | —O—CH(COSC$_3$H$_7$-n)—C$_6$H$_5$ | amorphous solid |
| 199 | Cl | H | —O—CH(COOC$_4$H$_9$-n)—C$_6$H$_5$ | mp 106.5–107.5° C. |
| 200 | Br | H | —O—CH(COOC$_4$H$_9$-n)—C$_6$H$_5$ | mp 108–108.5° C. |
| 201 | Br | H | —O—CH(COOC$_4$H$_9$-i)—C$_6$H$_5$ | mp 98–98.5° C. |

TABLE 1-continued

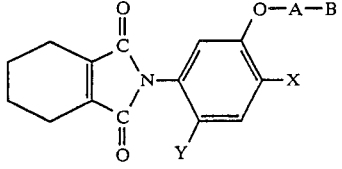

| | X | Y | —O—A—B | m.p. or $n_D$ |
|---|---|---|---|---|
| 202 | Br | H | $COOCH_2CH_2F$<br>$-O-CH-C_6H_5$ | mp 104.5–105.5° C. |
| 203 | Br | H | $COOCH_2CF_2CHF_2$<br>$-O-CH-C_6H_5$ | mp 93–94° C. |
| 204 | Br | H | $COO(CH_2CH_2O)_2CH_3$<br>$-O-CH-C_6H_5$ | $n_D{}^{25}$ 1.5515 |
| 205 | Br | H | $COO(CH_2)_2SC_2H_5$<br>$-O-CH-C_6H_5$ | mp 105–106° C. |
| 206 | Cl | H | $COO(CH_2)_2SC_4H_9-n$<br>$-O-CH-C_6H_5$ | $n_D{}^{27}$ 1.5823 |
| 207 | Br | H | $COOCH_2COCH_3$<br>$-O-CH-C_6H_5$ | mp 111.5–113° C. |
| 208 | Br | H | $COO(CH_2)_3COCH_3$<br>$-O-CH-C_6H_5$ | amorphous solid |
| 209 | Cl | H | $COOC_2H_5$<br>$-O-CH-C_6H_4-Cl$ | mp 112–114° C. |
| 210 | Cl | H | $COOC_4H_9-n$<br>$-O-CH-C_6H_4-Cl$ | mp 127–129° C. |
| 211 | Cl | H | $COOC_2H_5$<br>$-O-CH-C_6H_4-Br$ | mp 116–117° C. |
| 212 | Br | H | $COOC_2H_5$<br>$-O-CH-C_6H_4-Br$ | mp 130–131.5° C. |

TABLE 1-continued

[Structure: tetrahydrophthalimide N-linked to phenyl ring bearing O-A-B (para to N), X, and Y substituents]

| No. | X | Y | —O—A—B | m.p. or $n_D$ |
|---|---|---|---|---|
| 213 | Cl | H | —O—CH(COOC$_4$H$_9$-n)—C$_6$H$_4$—Br(p) | mp 120–121° C. |
| 214 | Br | H | —O—CH(CH$_3$)—COO—CH(CH$_3$)CH$_2$—O—C(=O)— (γ-butyrolactone) | mp 140–151° C. |
| 215 | Br | H | —O—CH(C$_2$H$_5$)—COO—CH—CH$_2$—O—C(=O)— (γ-butyrolactone) | mp 53–57° C. |
| 216 | Cl | H | —O—CH$_2$—COOH | mp 174–175° C. |
| 217 | Cl | H | —O—CH$_2$COOC$_4$H$_9$—n | mp 56–57° C. |
| 218 | Br | H | —O—CH$_2$COOC$_4$H$_9$—n | mp 51–53° C. |
| 219 | Cl | H | —O—CH$_2$—COOC$_5$H$_{11}$—n | mp 68–69° C. |
| 220 | Cl | H | —O—CH(CH$_3$)—COOCH$_2$CN | $n_D^{21}$ 1.5516 |
| 221 | Br | H | —O—CH(CH$_3$)—COSCH$_2$—C$_6$H$_5$ | amorphous solid |
| 222 | H | H | —O—CH$_2$—COOC$_2$H$_5$ | mp 78–79° C. |
| 223 | H | H | —O—CH(CH$_3$)—COOCH$_3$ | mp 62–64° C. |
| 224 | H | H | —O—CH(CH$_3$)—COOC$_2$H$_5$ | mp 94–95° C. |
| 225 | H | H | —O—CH(C$_2$H$_5$)—COOC$_2$H$_5$ | mp 43–44° C. |
| 226 | H | H | —O—CH$_2$CH$_2$CH$_2$—COOC$_2$H$_5$ | mp 48–49° C. |
| 227 | H | H | —O—CH$_2$CN | mp 135–136° C. |
| 228 | Cl | H | —O—CH$_2$CN | mp 123–125° C. |
| 229 | Br | H | —O—CH$_2$CN | mp 149–150° C. |
| 230 | Cl | H | —O—CH(CH$_3$)CN | mp 96–98° C. |
| 231 | Br | H | —O—CH(CH$_3$)CN | mp 120–121° C. |
| 232 | Cl | Cl | —O—CH(CH$_3$)CN | mp 141.5–142° C. |

TABLE 1-continued

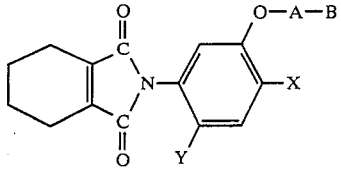

| | X | Y | —O—A—B | m.p. or $n_D$ |
|---|---|---|---|---|
| 233 | Br | H | —O—CH(C$_2$H$_5$)CN | mp 76–81° C. |
| 234 | Cl | H | —O—CH$_2$CH$_2$CH$_2$CN | mp 89–90° C. |
| 235 | Cl | H | —O—CH(C$_3$H$_7$-n)—CN | mp 79–80° C. |
| 236 | Br | H | —O—CH(C$_3$H$_7$-n)—CN | mp 88–89° C. |
| 237 | Cl | H | —O—CH(C$_5$H$_{11}$-n)—CN | $n_D^{25}$ 1.5491 |
| 238 | Br | H | —O—CH(C$_5$H$_{11}$-n)—CN | $n_D^{25}$ 1.5598 |
| 239 | Cl | H | —O—CH$_2$CONHC$_3$H$_7$-n | mp 225–230° C. |
| 240 | Cl | H | —O—CH(CH$_3$)—CONHCH$_3$ | mp 163.5–164.5° C. |
| 241 | Br | H | —O—CH(CH$_3$)CONHCH$_3$ | mp 180–181° C. |
| 242 | Cl | H | —O—CH(CH$_3$)CONHC$_2$H$_5$ | mp 166–166.5° C. |
| 243 | Br | H | —O—CH(CH$_3$)CONHC$_2$H$_5$ | mp 159–161° C. |
| 244 | Cl | H | —O—CH(CH$_3$)CONHC$_3$H$_7$-n | mp 116.5–117° C. |
| 245 | Br | H | —O—CH(CH$_3$)CONHC$_3$H$_7$-n | mp 116–117° C. |
| 246 | Cl | Cl | —O—CH(CH$_3$)CONHC$_3$H$_7$-n | mp 145–146° C. |
| 247 | Br | H | —O—CH(CH$_3$)CONHC$_3$H$_7$-i | mp 118–120° C. |
| 248 | Br | H | —O—CH(CH$_3$)CONHC$_4$H$_9$-n | mp 111–112° C. |
| 249 | Br | H | —O—CH(CH$_3$)CONHC$_4$H$_9$-i | mp 112–113° C. |
| 250 | Br | H | —O—CH(CH$_3$)CONHC$_4$H$_9$-t | mp 186.5–187° C. |
| 251 | Cl | H | —O—CH(CH$_3$)CONHC$_5$H$_{11}$-n | mp 110–112° C. |

TABLE 1-continued

[Structure: tetrahydrophthalimide with N-phenyl group bearing O-A-B, X, Y substituents]

| | X | Y | —O—A—B | m.p. or $n_D$ |
|---|---|---|---|---|
| 252 | Br | H | —O—CH(CH₃)CONHC₇H₁₅—n | mp 105–106° C. |
| 253 | Cl | H | —O—CH(CH₃)CONHCH₂CH=CH₂ | mp 120–121° C. |
| 254 | Br | H | —O—CH(CH₃)CONHCH₂CH=CH₂ | mp 120.5–121° C. |
| 255 | Cl | H | —O—CH(CH₃)CONHCH₂C≡CH | mp 172–173° C. |
| 256 | Br | H | —O—CH(CH₃)CONHCH₂C≡CH | mp 167–168.5° C. |
| 257 | Br | H | —O—CH(CH₃)CONHCH₂CHClCH₃ | mp 114–115° C. |
| 258 | Br | H | —O—CH(CH₃)CONHCH₂CH₂OCH₃ | mp 178.5–179.5° C. |
| 259 | Br | H | —O—CH(CH₃)CONHCH₂—C₆H₅ | mp 95–98° C. |
| 260 | Cl | H | —O—CH(CH₃)—CONH—C₆H₅ | mp 163–164° C. |
| 261 | Br | H | —O—CH(CH₃)—CONH—C₆H₅ | mp 187–188° C. |
| 262 | Cl | Cl | —O—CH(CH₃)CONH—C₆H₅ | mp 126–127° C. |
| 263 | Cl | H | —O—CH(CH₃)—CONH—OCH₃ | mp 162–162.5° C. |
| 264 | Cl | H | —O—CH(CH₃)—CONH—OC₃H₇—n | mp 145–145.5° C. |
| 265 | Cl | H | —O—CH(CH₃)—CONHOCH₂CH=CH₂ | mp 138–139.5° C. |
| 266 | Br | H | —O—CH(CH₃)—CONH—N(CH₃)₂ | mp 152–154° C. |
| 267 | Cl | H | —O—CH(CH₃)—CONHSO₂—C₆H₅ | mp 78–82° C. |
| 268 | Cl | H | —O—CH(CH₃)—CON(CH₃)₂ | mp 121.5–122.5° C. |
| 269 | Br | H | —O—CH(CH₃)—CON(CH₃)₂ | mp 135–136° C. |

TABLE 1-continued

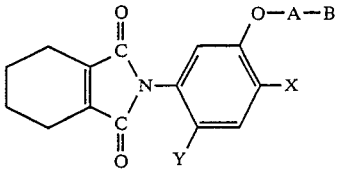

| | X | Y | —O—A—B | m.p. or $n_D$ |
|---|---|---|---|---|
| 270 | Cl | Cl | —O—CH(CH₃)—CON(CH₃)₂ | mp 116–117° C. |
| 271 | Br | H | —O—CH(CH₃)—CON(C₄H₉-n)—CH₃ | mp 118–119° C. |
| 272 | Br | H | —O—CH(CH₃)—CON(C₂H₅)₂ | mp 88.5–89.5° C. |
| 273 | Br | H | —O—CH(CH₃)—CON(C₄H₉-n)—C₂H₅ | $n_D^{25.5}$ 1.5549 |
| 274 | Br | H | —O—CH(CH₃)—CON(CH₂CH=CH₂)—CH₂CH=CH₂ | mp 99–100° C. |
| 275 | Br | H | —O—CH(CH₃)—CON(CH₃)(C₆H₅) | mp 51–54° C. |
| 276 | Br | H | —O—CH(CH₃)—CON(C₂H₅)(C₆H₅) | mp 129.5–130° C. |
| 277 | Br | H | —O—CH(CH₃)—CON(C₃H₇-n)(C₆H₅) | mp 121–122° C. |
| 278 | Cl | H | —O—CH(CH₃)—CON(OCH₃)—CH₃ | mp 124–125° C. |
| 279 | Cl | H | —O—CH(CH₃)—CON(SO₂CH₃)—C₂H₅ | mp 97.5–98.5° C. |
| 280 | Cl | H | —O—CH(CH₃)—CON(SO₂CH₃)—CH₂CH=CH₂ | mp 109–109.5° C. |
| 281 | Br | H | —O—CH(CH₃)—CO—N(piperidinyl) | mp 131–132° C. |
| 282 | Br | H | —O—CH(CH₃)—CO—N(morpholinyl) | mp 63–67° C. |
| 283 | Br | H | —O—CH(C₂H₅)—CONH—(2-pyrimidinyl) | mp 108–110° C. |
| 284 | Cl | H | —O—CH(C₂H₅)—CONH—C₂H₅ | mp 202.5–204° C. |

TABLE 1-continued

Structure: tetrahydrophthalimide N-substituted with phenyl bearing O-A-B (position ortho to N via O), X, and Y substituents.

| No. | X | Y | —O—A—B | m.p. or $n_D$ |
|---|---|---|---|---|
| 285 | Br | H | —O—CH(C$_2$H$_5$)—CONH—C$_2$H$_5$ | mp 199–200° C. |
| 286 | Cl | H | —O—CH(C$_2$H$_5$)—CONH—C$_3$H$_7$-n | mp 148.5–149° C. |
| 287 | Br | H | —O—CH(C$_2$H$_5$)—CONH—C$_3$H$_7$-n | mp 143.5–144.5° C. |
| 288 | Br | H | —O—CH(C$_2$H$_5$)—CONH—C$_4$H$_9$-n | mp 124–125° C |
| 289 | Br | H | —O—CH(C$_2$H$_5$)—CONH—CH$_2$CH=CH$_2$ | mp 155.5–156.5° C. |
| 290 | Cl | H | —O—CH(C$_2$H$_5$)—CONH—CH$_2$C≡CH | mp 136.5–138° C. |
| 291 | Br | H | —O—CH(C$_2$H$_5$)—CONH—C(CH$_3$)(CH$_3$)—CH$_2$Cl | mp 127–128.5° C. |
| 292 | Cl | H | —O—CH(C$_2$H$_5$)—CONH—C(CH$_3$)(CH$_3$)—CH$_2$OH | mp 122–130° C. decomp. |
| 293 | Br | H | —O—CH(C$_2$H$_5$)—CONH—cyclohexyl | mp 152–154.5° C. |
| 294 | Cl | H | —O—CH(C$_2$H$_5$)—CONH—C$_6$H$_5$ | mp 142–144° C. |
| 295 | Br | H | —O—CH(C$_2$H$_5$)—CONH—C$_6$H$_5$ | mp 148–149° C. |
| 296 | Br | H | —O—CH(C$_2$H$_5$)—CONH—C$_6$H$_4$-4-Cl | mp 181–183° C. |
| 297 | Cl | H | —O—CH(C$_2$H$_5$)—CON(CH$_3$)—CH$_3$ | mp 101–102° C. |
| 298 | Br | H | —O—CH(C$_2$H$_5$)—CON(C$_4$H$_9$-n)—CH$_3$ | mp 113.5–114.5° C. |
| 299 | Cl | H | —O—CH(C$_2$H$_5$)—CON(CH$_3$)—C$_6$H$_5$ | mp 97–98° C. |
| 300 | Cl | H | —O—CH(C$_2$H$_5$)—CON(OCH$_3$)CH$_3$ | mp 130–130.5° C. |
| 301 | Br | H | —O—CH(C$_2$H$_5$)—CO—N(morpholino) | mp 144–145.5° C. |

TABLE 1-continued

[Structure: tetrahydrophthalimide with N-phenyl bearing O-A-B, X, Y substituents]

| | X | Y | —O—A—B | m.p. or $n_D$ |
|---|---|---|---|---|
| 302 | Cl | H | —O—CH(C$_3$H$_7$-n)—CONHCH$_3$ | mp 183.5–185.5° C. |
| 303 | Cl | H | —O—CH(C$_3$H$_7$-n)—CONHC$_2$H$_5$ | mp 213.5–215.5° C. |
| 304 | Br | H | —O—CH(C$_3$H$_7$-n)—CONHC$_2$H$_5$ | mp 218.5–219.5° C. |
| 305 | Br | H | —O—CH(C$_3$H$_7$-n)—CONHC$_3$H$_7$-n | mp 185–186° C. |
| 306 | Cl | H | —O—CH(C$_3$H$_7$-n)—CONHC$_4$H$_9$-n | mp 121.5–122° C. |
| 307 | Cl | H | —O—CH(C$_3$H$_7$-n)—CONHCH$_2$CH=CH$_2$ | mp 182.5–183° C. |
| 308 | Cl | H | —O—CH(C$_3$H$_7$-n)—CONHCH$_2$C≡CH | mp 161–162° C. |
| 309 | Br | H | —O—CH(C$_3$H$_7$-n)—CONHCH$_2$C≡CH | mp 160.5–161° C. |
| 310 | Cl | H | —O—CH(C$_3$H$_7$-n)—CONHCH$_2$—C$_6$H$_5$ | mp 156–158° C. |
| 311 | Cl | H | —O—CH(C$_3$H$_7$-n)—CONH—C$_6$H$_5$ | mp 135–136.5° C. |
| 312 | Br | H | —O—CH(C$_3$H$_7$-n)—CONH—C$_6$H$_5$ | mp 157–158° C. |
| 313 | Cl | H | —O—CH(C$_3$H$_7$-n)—CON(CH$_3$)—CH$_3$ | mp 132–133° C. |
| 314 | Br | H | —O—CH(C$_3$H$_7$-n)—CON(OCH$_3$)—CH$_3$ | mp 92–93° C. |
| 315 | Cl | H | —O—CH(C$_4$H$_9$-n)—CONHC$_2$H$_5$ | mp 186–187° C. |
| 316 | Br | H | —O—CH(C$_4$H$_9$-n)—CONHC$_2$H$_5$ | mp 203–204° C. |
| 317 | Br | H | —O—CH(C$_4$H$_9$-n)—CONHCH$_2$—C$_6$H$_5$ | mp 124.5–125.5° C. |

TABLE 1-continued
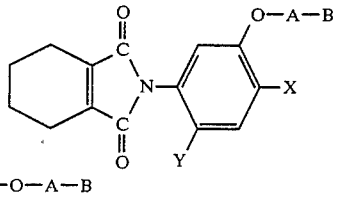
| | X | Y | —O—A—B | m.p. or $n_D$ |
|---|---|---|---|---|
| 318 | Cl | H | 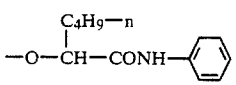 | mp 115.5–116.5° C. |
| 319 | Br | H | 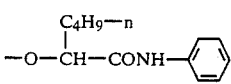 | mp 168–169° C. |
| 320 | Br | H | 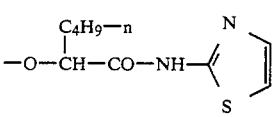 | mp 165–166° C. |
| 321 | Br | H | 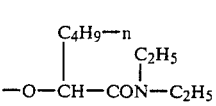 | amorphous solid |
| 322 | Cl | H | 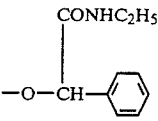 | mp 172–173.5° C. |
| 323 | Br | H | 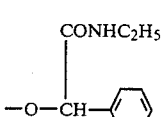 | mp 157–158° C. |
| 324 | Cl | H | 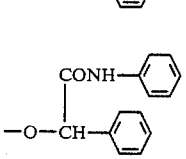 | mp 172.5–174° C. |
| 325 | Br | H | 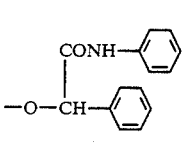 | mp 168–169° C. |
| 326 | Cl | H | 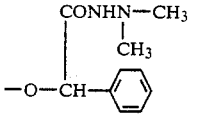 | mp 193.5–195° C. |
| 327 | Cl | H | 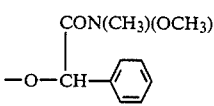 | mp 65–68° C. |
| 328 | Br | H | 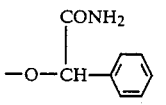 | mp 186–188° C. |
| 329 | Br | H | 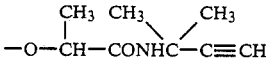 | mp 170.5–171° C. |

TABLE 1-continued

| | X | Y | —O—A—B | m.p. or $n_D$ |
|---|---|---|---|---|
| 330 | Br | H | —O—CH(C$_2$H$_5$)—CONH—(2-CH$_3$-C$_6$H$_4$) | mp 186.5–187° C. |
| 331 | Br | H | —O—CH(C$_2$H$_5$)—CONH—(3-OCH$_3$-C$_6$H$_4$) | mp 123.5–125.5° C. |
| 332 | Cl | H | —O—CH(C$_2$H$_5$)—CONH—NH—C$_6$H$_5$ | mp 165–167° C. |
| 333 | Br | H | —O—CH(C$_2$H$_5$)—CON(CH$_3$)—SO$_2$C$_4$H$_9$-n | mp 167–168° C. |
| 334 | Br | H | —O—CH(C$_3$H$_7$-n)—CONH—(4-pyridyl) | mp 173.5–175° C. |
| 335 | Cl | H | —O—CH(C$_4$H$_9$-n)—CONH—SO$_2$—(4-CH$_3$-C$_6$H$_4$) | mp 171–173° C. |
| 336 | Cl | H | —O—CH$_2$CON(CH$_3$)—CH$_3$ | mp 127.5–129° C. |
| 337 | Br | H | —O—CH$_2$—CON(CH$_3$)—C$_2$H$_5$ | mp 121–122.5° C. |
| 338 | Cl | H | —O—CH$_2$—CON(CH$_3$)—C$_3$H$_7$-n | mp 87–88° C. |
| 339 | Br | H | —O—CH$_2$—CON(CH$_3$)—OCH$_3$ | mp 130–131° C. |
| 340 | Cl | H | —O—CH$_2$—CON(CH$_3$)—OC$_2$H$_5$ | mp 124–125.5° C. |
| 341 | Cl | H | —O—CH(CH$_3$)—CON(CH$_3$)C$_2$H$_5$ | mp 143–144° C. |
| 342 | Br | H | —O—CH(CH$_3$)CON(CH$_3$)—C$_2$H$_5$ | mp 128–129.5° C. |
| 343 | Cl | H | —O—CH(CH$_3$)—CON(CH$_3$)—C$_3$H$_7$-n | mp 92.5–93.5° C. |
| 344 | Br | H | —O—CH(CH$_3$)—CON(CH$_3$)—C$_3$H$_7$-n | mp 100–101° C. |
| 345 | Cl | H | —O—CH(CH$_3$)—CON(CH$_3$)CH$_2$CH=CH$_2$ | mp 96.5–97.5° C. |
| 346 | Br | H | —O—CH(CH$_3$)—CON(CH$_3$)CH$_2$CH=CH$_2$ | mp 88.5–89° C. |

TABLE 1-continued

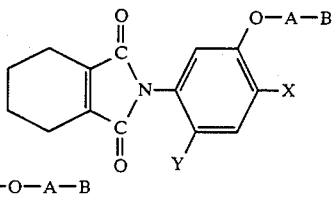

| | X | Y | —O—A—B | m.p. or $n_D$ |
|---|---|---|---|---|
| 347 | Cl | H | —O—CH(CH$_3$)—CON(CH$_3$)CH$_2$C≡CH | mp 144–145° C. |
| 348 | Br | H | —O—CH(CH$_3$)—CON(CH$_3$)CH$_2$C≡CH | mp 108–109° C. |
| 349 | Br | H | —O—CH(CH$_3$)—CON(CH$_3$)—CH$_2$—C$_6$H$_5$ | mp 130–131° C. |
| 350 | Cl | H | —O—CH(CH$_3$)—CON(CH$_3$)CH$_2$CH$_2$OH | mp 136–137° C. |
| 351 | Cl | H | —O—CH(CH$_3$)—CON(CH$_3$)CH$_2$CH$_2$Cl | mp 112–113.5° C. |
| 352 | Cl | H | —O—CH(CH$_3$)—CON(CH$_3$)CH$_2$CH$_2$OCH$_3$ | mp 73–75° C. |
| 353 | Br | H | —O—CH(CH$_3$)—CON(CH$_3$)—OCH$_3$ | mp 113.5–114.5° C. |
| 354 | Cl | Cl | —O—CH(CH$_3$)—CON(CH$_3$)OCH$_3$ | mp 131–132.5° C. |
| 355 | Cl | H | —O—CH(CH$_3$)—CON(CH$_3$)—OC$_2$H$_5$ | mp 153.5–155° C. |
| 356 | Br | H | —O—CH(CH$_3$)—CON(CH$_3$)—OC$_2$H$_5$ | mp 152–153.5° C. |
| 357 | Cl | H | —O—CH(CH$_3$)—CON(CH$_3$)OC$_3$H$_7$—n | mp 104–105° C. |
| 358 | Cl | H | —O—CH(CH$_3$)—CON(CH$_3$)OC$_3$H$_7$—i | mp 138–139° C. |
| 359 | Cl | H | —O—CH(CH$_3$)—CON(CH$_3$)OCH$_2$CH=CH$_2$ | mp 92.5–93° C. |
| 360 | Cl | H | —O—CH(CH$_3$)—CON(C$_2$H$_5$)—OCH$_3$ | mp 108–110° C. |
| 361 | Br | H | —O—CH(CH$_3$)—CON(C$_2$H$_5$)—OCH$_3$ | mp 117.5–119.5° C. |
| 362 | Cl | H | —O—CH(CH$_3$)—CON(C$_3$H$_7$—n)—OCH$_3$ | mp 79.5–80.5° C. |
| 363 | Br | H | —O—CH(CH$_3$)—CON(C$_3$H$_7$—n)—OCH$_3$ | mp 100.5–101.5° C. |
| 364 | Cl | H | —O—CH(CH$_3$)—CON(C$_3$H$_7$—i)—OCH$_3$ | mp 135–136° C. |

TABLE 1-continued

| | X | Y | —O—A—B | m.p. or $n_D$ |
|---|---|---|---|---|
| 365 | Cl | H | —O—CH(CH₃)—CON(OCH₃)—CH₂CH=CH₂ | mp 84–85° C. |
| 366 | Br | H | —O—CH(CH₃)—CON(OCH₃)—CH₂CH=CH₂ | mp 95–96.5° C. |
| 367 | Cl | H | —O—CH(CH₃)—CON(OCH₃)—CH₂C≡CH | mp 116–117.5° C. |
| 368 | Br | H | —O—CH(CH₃)—CON(OCH₃)—CH₂C≡CH | amorphous solid |
| 369 | Cl | H | —O—CH(CH₃)—CON(OCH₃)—C₂H₅ | mp 104–105° C. |
| 370 | Br | H | —O—CH(CH₃)—CON(OC₂H₅)—C₂H₅ | mp 105.5–106.5° C. |
| 371 | Cl | H | —O—CH(CH₃)—CONHCH₂CH=CHCH₃ | mp 156–158° C. |
| 372 | Br | H | —O—CH(CH₃)—CONHCH₂CH=CHCH₃ | mp 158–160° C. |
| 373 | Cl | H | —O—CH(CH₃)—CONHCH₂CH₂CH=CH₂ | mp 125–127° C. |
| 374 | Cl | H | —O—CH(CH₃)—CON(—O—)  (pyrrolidinyl-oxy) | mp 142.5–144° C. |
| 375 | Br | H | —O—CH(CH₃)—CON(—O—)  (pyrrolidinyl-oxy) | mp 120.5–122° C. |
| 376 | Cl | H | —O—CH(CH₃)—CON(—O—)  (piperidinyl-oxy) | mp 140–141° C. |
| 377 | Br | H | —O—CH(C₂H₅)—CON(CH₃)—CH₃ | mp 109.5–110° C. |
| 378 | Cl | H | —O—CH(C₂H₅)—CON(CH₃)—C₂H₅ | mp 123–124° C. |
| 379 | Br | H | —O—CH(C₂H₅)—CON(CH₃)—C₂H₅ | mp 126.5–128° C. |
| 380 | Cl | H | —O—CH(C₂H₅)—CON(CH₃)—C₃H₇—n | mp 95–95.5° C. |

TABLE 1-continued

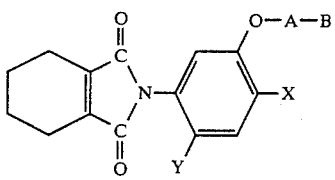

| | X | Y | —O—A—B | m.p. or $n_D$ |
|---|---|---|---|---|
| 381 | Br | H | —O—CH(C$_2$H$_5$)—CON(CH$_3$)—C$_3$H$_7$-n | mp 102.5–103.5° C. |
| 382 | Cl | H | —O—CH(C$_2$H$_5$)—CON(CH$_3$)CH$_2$CH=CH$_2$ | mp 101–102° C. |
| 383 | Br | H | —O—CH(C$_2$H$_5$)—CON(CH$_3$)CH$_2$CH=CH$_2$ | mp 104.5–105.5° C. |
| 384 | Cl | H | —O—CH(C$_2$H$_5$)—CON(CH$_3$)CH$_2$C≡CH | mp 106–107° C. |
| 385 | Br | H | —O—CH(C$_2$H$_5$)—CON(CH$_3$)—CH$_2$C≡CH | amorphous solid |
| 386 | Cl | H | —O—CH(C$_2$H$_5$)—CON(CH$_3$)—CH$_2$CH$_2$OCH$_3$ | mp 94.5–95.5° C. |
| 387 | Cl | Cl | —O—CH(C$_2$H$_5$)—CON(CH$_3$)—C$_6$H$_5$ | mp 107–108° C. |
| 388 | Br | H | —O—CH(C$_2$H$_5$)—CON(C$_2$H$_5$)—C$_6$H$_5$ | mp 133–134° C. |
| 389 | Br | H | —O—CH(C$_2$H$_5$)—CON(CH$_3$)—OCH$_3$ | mp 126–127° C. |
| 390 | Cl | H | —O—CH(C$_2$H$_5$)—CON(CH$_3$)—OC$_2$H$_5$ | mp 83–84.5° C. |
| 391 | Cl | H | —O—CH(C$_2$H$_5$)—CON(CH$_3$)—OC$_3$H$_7$-n | mp 85–86° C. |
| 392 | Cl | H | —O—CH(C$_2$H$_5$)—CON(CH$_3$)OCH$_2$CH=CH$_2$ | mp 94.5–95° C. |
| 393 | Cl | H | —O—CH(C$_2$H$_5$)—CON(C$_2$H$_5$)—OCH$_3$ | mp 99–100° C. |
| 394 | Cl | H | —O—CH(C$_2$H$_5$)—CON(C$_2$H$_5$)—OC$_2$H$_5$ | mp 95–96° C. |
| 395 | Cl | H | —O—CH(C$_2$H$_5$)—CON(C$_3$H$_7$-n)—OCH$_3$ | mp 101–102° C. |
| 396 | Cl | H | —O—CH(C$_2$H$_5$)—CON(C$_3$H$_7$-i)OCH$_3$ | mp 112.5–113° C. |
| 397 | Cl | H | —O—CH(C$_2$H$_5$)—CON(CH$_2$CH=CH$_2$)—OCH$_3$ | mp 81–82° C. |

TABLE 1-continued

[Structure: tetrahydrophthalimide N-linked to phenyl ring bearing O—A—B, X, Y substituents]

| | X | Y | —O—A—B | m.p. or $n_D$ |
|---|---|---|---|---|
| 398 | Cl | H | —O—CH(C$_2$H$_5$)—CON(OCH$_3$)—CH$_2$C≡CH | amorphous solid |
| 399 | Cl | H | —O—CH(C$_2$H$_5$)—CONHCH$_3$ | mp 187.5–189° C. |
| 400 | Cl | H | —O—CH(C$_2$H$_5$)—CONHCH$_2$CH=CH$_2$ | mp 159–160° C. |
| 401 | Br | H | —O—CH(C$_2$H$_5$)—CONHCH$_2$C≡CH | mp 130–131° C. |
| 402 | Cl | Cl | —O—CH(C$_2$H$_5$)—CONHCH$_2$C≡CH | mp 149–150° C. |
| 403 | Cl | H | —O—CH(C$_2$H$_5$)—CONHCH$_2$CH=CHCH$_3$ | mp 156–158° C. |
| 404 | Cl | H | —O—CH(C$_2$H$_5$)—CONHCH$_2$CH$_2$CH=CH$_2$ | mp 122.5–124° C. |
| 405 | Br | H | —O—CH(C$_2$H$_5$)—CONHCH$_2$—C$_6$H$_5$ | mp 169–170° C. |
| 406 | Cl | H | —O—CH(C$_2$H$_5$)—CON(morpholino via 5-ring, O) | mp 167–168° C. |
| 407 | Cl | H | —O—CH(C$_2$H$_5$)—CON(morpholino 6-ring, O) | mp 141–141.5° C. |
| 408 | Br | H | —O—CH(n-C$_3$H$_7$)—CON(CH$_3$)—CH$_3$ | mp 138–139° C. |
| 409 | Cl | Cl | —O—CH(n-C$_3$H$_7$)—CON(CH$_3$)—CH$_3$ | amorphous solid |
| 410 | Cl | H | —O—CH(n-C$_3$H$_7$)—CON(CH$_3$)—C$_2$H$_5$ | mp 127.5–128.5° C. |
| 411 | Br | H | —O—CH(n-C$_3$H$_7$)—CON(CH$_3$)—C$_2$H$_5$ | mp 134.5–135° C. |
| 412 | Cl | H | —O—CH(n-C$_3$H$_7$)—CON(CH$_3$)—n-C$_3$H$_7$ | $n_D^{25}$ 1.5526 |

TABLE 1-continued

[Structure: tetrahydrophthalimide with N-phenyl group bearing O-A-B, X, Y substituents]

| | X | Y | —O—A—B | m.p. or $n_D$ |
|---|---|---|---|---|
| 413 | Cl | H | —O—CH(C$_3$H$_7$-n)—CON(CH$_3$)—CH$_2$CH=CH$_2$ | mp 76–78° C. |
| 414 | Br | H | —O—CH(C$_3$H$_7$-n)—CON(CH$_3$)—C$_6$H$_5$ | amorphous solid |
| 415 | Cl | H | —O—CH(C$_3$H$_7$-n)—CON(CH$_3$)—OCH$_3$ | mp 104.5–106° C. |
| 416 | Cl | Cl | —O—CH(C$_3$H$_7$-n)—CON(CH$_3$)—OCH$_3$ | amorphous solid |
| 417 | Cl | H | —O—CH(C$_3$H$_7$-n)—CON(C$_2$H$_5$)—OCH$_3$ | mp 92–93.5° C. |
| 418 | Br | H | —O—CH(C$_3$H$_7$-n)—CON(C$_2$H$_5$)—OC$_2$H$_5$ | mp 96–97° C. |
| 419 | Br | H | —O—CH(C$_3$H$_7$-n)—CON(C$_3$H$_7$-n)—OCH$_3$ | mp 108–109.5° C. |
| 420 | Br | H | —O—CH(C$_3$H$_7$-n)—CONHCH$_3$ | mp 187.5–188.5° C. |
| 421 | Cl | H | —O—CH(C$_3$H$_7$-n)—CONHCH$_2$CH$_2$CH=CH$_2$ | mp 115–116.5° C. |
| 422 | Br | H | —O—CH(C$_3$H$_7$-n)—CONHCH$_2$—C$_6$H$_5$ | mp 151–152.5° C. |
| 423 | Cl | H | —O—CH(C$_4$H$_9$-n)—CON(CH$_3$)—CH$_3$ | mp 141–142° C. |
| 424 | Br | H | —O—CH(C$_4$H$_9$-n)—CON(CH$_3$)—CH$_3$ | mp 156–157° C. |
| 425 | Br | H | —O—CH(C$_4$H$_9$-n)—CON(CH$_3$)—C$_2$H$_5$ | mp 155.5–156.5° C. |
| 426 | Br | H | —O—CH(C$_4$H$_9$-n)—CON(CH$_3$)—C$_3$H$_7$-n | mp 81–83° C. |

TABLE 1-continued

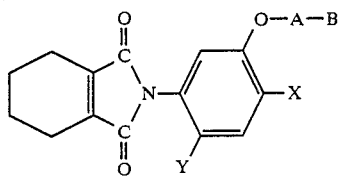

| | X | Y | —O—A—B | m.p. or $n_D$ |
|---|---|---|---|---|
| 427 | Br | H | —O—CH(C₄H₉-n)—CON(CH₃)—CH₂CH=CH₂ | mp 99–100° C. |
| 428 | Br | H | —O—CH(C₄H₉-n)—CON(CH₃)CH₂C≡CH | mp 93.5–95° C. |
| 429 | Br | H | —O—CH(C₄H₉-n)—CON(CH₃)—Ph | amorphous solid |
| 430 | Cl | H | —CH(C₄H₉-n)—CON(CH₃)—OCH₃ | mp 101.5–102° C. |
| 431 | Br | H | —O—CH(C₄H₉-n)—CONHCH₃ | mp 158–159° C. |
| 432 | Br | H | —O—CH(CON(CH₃)₂)—Ph | mp 157–159° C. |
| 433 | Br | H | —O—CH(C₃H₇-n)—CON(CH₃)—OC₂H₅ | mp 82–83.5° C. |
| 434 | Cl | H | —O—CH(C₃H₇-n)—CON(CH₃)—CH₂C≡CH | mp 87.5–89° C. |

The following compounds are also included as the compounds (I) of the present invention; N-[4-chloro-3-(2-cyanoethoxy)phenyl]-3,4,5,6-tetrahydrophthalimide, N-[4-bromo-3-(2-cyanoethoxy)phenyl]-3,4,5,6-tetrahydrophthalimide, N-[4-chloro-3-(1-cyanopropoxy)phenyl]-3,4,5,6-tetrahydrophthalimide, N-[4-bromo-3-(3-cyanopropoxy)phenyl]-3,4,5,6-tetrahydrophthalimide, N-[4-chloro-3-(1-cyanopentyloxy)phenyl]-3,4,5,6-tetrahydrophthalimide, and N-[4-bromo-3-(1-cyanopentyloxy)phenyl]-3,4,5,6-tetrahydrophthalimide.

The following compounds are especially preferable as herbicides used in upland.

The compounds having the formula (I) wherein X is Cl; Y is H and A is

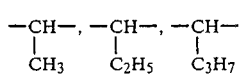

and B is

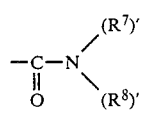

and $(R^7)'$ is H, methyl or methoxy group and $(R^8)'$ is a $C_{1-4}$ alkyl, a $C_{1-4}$ alkoxy, allyl or propargyl group.

The following compounds are also preferable as herbicides used in upland. The compounds having the formula (I) wherein X is Br; Y, A and B are defined above. The following compounds are also useful.

The compounds having the formula (I) wherein X is Cl; B is CN; and Y and B are defined above; or X is Br; B is CN and Y and B are defined above.

These compounds are Compounds Nos. 278, 290, 300, 355, 356, 360, 363, 377, 378, 382, 384, 393, 401, 408, 411, 230, 231, 233 and 235.

The following compounds are especially preferable as herbicides used in paddy field.

The compounds having the formula (I) wherein X is Br or Cl; Y is H; A is

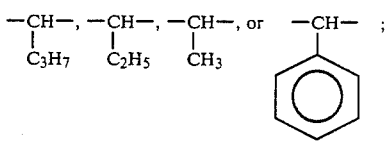

B is

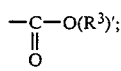

and $(R^3)'$ is a $C_{1-4}$ alkyl group; or B is

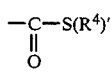

and $(R^4)'$ is a a $C_{2-3}$ alkyl group; or B is

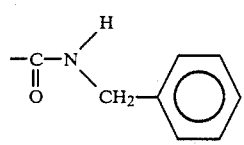

These compounds are Compounds Nos. 60, 61, 87, 90, 95, 96, 93, 94, 99, 100, 195, 259, 317, 349, 405 and 422.

The compounds (I) can be used as herbicides without an adjuvant. Thus, the compounds (I) are usually used in a form of herbicidal compositions such as an emulsifiable concentrate, a wettable powder, a dust, a granule and a tablet which can be prepared by admixing the active ingredient with a suitable inert liquid or solid carrier and another adjuvant such as suitable surfactants.

Suitable liquid carriers include toluene, xylene, methyl naphthalene, cyclohexane, butanol, glycol, dimethylsulfoxide, dimethylformamide, acetone, methyl isobutyl ketone, animal or vegetable oils, fatty acid, fatty acid esters and water.

Suitable solid carriers include clay, kaolin clay, talc, bentonite, diatomaceous earth, silica, calcium carbonate, soybean powder, wheat powder, other plant powder etc.

It is also possible to incorporate the other agricultural chemical such as agricultural fungicides, insecticides, nematocides, and the other herbicides, plant growth regulators, soil improvers and fertilizers.

It is also possible to incorporate a suitable adjuvant such as a spreader, an emulsifier, a wet spreader and a sticker for improving the herbicidal effect.

Suitable amounts of the active ingredient and the adjuvants in the herbicidal compositions of the present invention are as follows.

|  | Active ingredient | Surfactant | Carrier | Other additive |
|---|---|---|---|---|
|  |  |  |  | (% by weight) |
| Wettable powder | 5 to 80 | 2 to 20 | 10 to 93 | 0 to 5 |
| Flowable | 5 to 60 | 5 to 30 | 10 to 90 | 0 to 20 |
| Granule | 1 to 20 | 2 to 10 | 70 to 97 | 0 to 5 |
| Emulsifiable concentrate | 5 to 80 | 5 to 30 | 10 to 90 | 0 to 5 |

A dose of the compound (I) as the herbicide is depending upon a kind of the compound, a kind of weed, a season and method of the application and a kind of soil and is usually in a range of 2 to 80 g./are.

The compounds (I) as the herbicide of the present invention can be applied in flooded soil treatment at preemergence or in treatments at growth period, and impart excellent herbicidal activity to annual weeds and perennial weeds and have low phytotoxicity to transplanted rice seedling which are remarkably preferable as herbicide in paddy field. In the soil treatment at preemergence and the foliage and soil treatment in upland, the compounds of the present invention impart excellent herbicidal activity to annual weeds and perennial weeds and high residual effect. The phytotoxicity to crop plants is remarkably low, even though it is applied at high concentration.

The compounds as a herbicide of the present invention are used for controlling the following weeds.

| Scientific name | (American name) |
|---|---|
| Dicotyledonous weeds: | |
| lpomoea spp. | (morningglories) |
| Galium aparine | (bedstraw) |
| Stellaria media | (common chickweed) |
| Galinsoga ciliata | (hairy galinsoga) |
| Chenopodium album var. controrubrum | |
| Chenopodium album | (lambsquarters) |
| Abutilon theophrasti | (velvetleaf) |
| Brassica kaber var. pinnatifida | (wild mustard) |
| Capsella bursa-pastoris | (shepherdspurse) |
| Rumex japonicus | |
| Polygonum persicaria | (ladysthumb) |
| Portulaca aleracea | (common purslane) |
| Amaranthus lividus | (livid amaranth) |
| Ambrosia artemisifolia | (common ragweed) |
| Rotala indica | (toothcup) |
| Lindernia procumbens | |
| Eclipta prostrata | |
| Bidens tripartita | |
| Dopatrium junceum | |
| Elatine triandra | |
| Polygonum thunbergii | |
| Monocotyledonous weeds: | |
| Echinochloa crus-galli | (barnyard grass) |
| Digitaria sanguinalis | (large crabgrass) |
| Eleusine indica | (goosegrass) |
| Setaria viridis | (green foxtail) |
| Poa annua | (annual bluegrass) |
| Alopecurus aequalis | (water foxtail) |
| Cynodon dactylon | (bermudagrass) |
| Agropyron repens | (quackgrass) |
| Cyperus microiria | |
| Cyperus difformis | |
| Eleocharis kuroguwai | (water chestnut) |
| Eleocharis acicularis | (slender spikerush) |
| Scirpus juncoides | (hardstem bulrush) |
| Cyperus serotinus | |
| Scirpus maritimus | |
| Monochoria vaginalis | |
| Sagitaria pygmaea | |
| Alisma canaliculatum | |
| Sagitaria trifolia | |

The compounds as a herbicide of the present invention can be used as selective herbicides in the cultivation of the following crops.

| Dicotyledonous crops: | |
|---|---|
| Glycine max | (soybean) |
| Gossypium indicum | (cotton) |
| Beta vulgaris | (sugar beet) |
| Helianthus annuus | (sunflower) |
| Pisum sativum | (pea) |
| Solanum tuberosum | (potato) |
| Cucumis sativus | (cucumber) |

-continued

| Monocotyledonous crops: | |
|---|---|
| Oryza sativa | (rice) |
| Triticum aestivum | (wheat) |
| Hordoum vulgare | (barley) |
| Avena fatua | (oat) |
| Secale cereale | (rye) |
| Zea mays | (corn) |
| Saccharum officinarum | (sugar cane) |

The application of the compounds as a herbicide of the present invention is not only to the aforementioned plants but also to the other plants by the same manner.

The herbicides and herbicidal compositions of the present invention will be further illustrated by certain examples for preparations and herbicidal experimental tests which are provided for purposes of illustration only and are not intended to be limiting the present invention.

In the preparations and the experiments, the term "part" means "parts by weight" and Compound numbers correspond to Compounds shown in Table 1. As references, the following compounds are also used.

Reference A: N-(3-methoxy-4-chlorophenyl)-3,4,5,6-tetrahydrophthalimide
Reference B: N-(3-methoxy-4-bromophenyl)-3,4,5,6-tetrahydrophthalimide
Reference C: 2,4,6-trichlorophenyl-4'-nitrophenyl ether
Reference D: S-(2-chlorobenzyl)-N,N-diethylthiol-carbamate
Reference E: 3-(3,4-dichlorophenyl)-1,1-dimethylurea
Reference F: 2,4-dichlorophenyl-4'-nitrophenyl ether
Reference G: 3,4-dichloropropionic anilide

Wettable powder

Compound shown in Table 1—50 parts
Carplex #80 (Shionogi Seiyaku K.K.)—15 parts
N,N-kaolin clay (Tsuchiya Kaolin K.K.)—30 parts
Sorpol 8070 (Toho Kagaku K.K.) (higher alkyl sulfate surfactant)—5 parts The components were uniformly mixed and ground to obtain a wettable powder containing 50% of the active ingredient.

Granule

Compound shown in Table 1—5 parts
Clay (Nippon Talc K.K.)—38 parts
Bentonite (Hojunyoko K.K.)—55 parts
Aerol CT-1 (Toho Kagaku K.K.) (succinate type surfactant)—2 parts The components were mixed with water and kneaded and granulated by a granulating machine and dried at 60° C. for 2 hours to obtain a granule containing 5% of the active ingredient.

Emulsifiable concentrate

Compound shown in Table 1—30 parts
Xylene—30 parts
Dimethylformamide—25 parts

The compound was dissolved into the mixed solvent and then, 15 parts of polyoxyethylene type surfactant (Sorpol 3005X: Toho Kagaku K.K.) was admixed to obtain an emulsifiable concentrate containing 30% of the active ingredient.

In the tests, the following weeds were used and the weeds are shown by the following symbols.
Barnyardgrass (*Echinochloa crus-galli*): B.G.
Tooth cup (*Rotala indica*): T.C.
Narrowleaf waterplantain (*Alisma canaliculatum*): N.W.
Hardstem bulrush (*Scirpus juncoides*): H.B.
Crabgrass (*Digitaria songuinalis* (L.) Scop): C.G.
Ladys thumb (*Polygonum persicaria*): L.T.
Lambsguarter (*Chenopoduim album* L.): L.A.
Sawa millet (*Echinochloa frumentacea*): S.M.

Test A (i) Flooded paddy field test for preemergence of paddy weeds

Each pot of 1/2500 are filled with paddy diluvium soil and manured (fertilizer application) and seeds of Barnyardgrass, Tooth cup, Hardstem bulrush, and Narrowleaf waterplantain were sown. The seeds were mixed well in the upper layer having a thickness of 2 cm and the pot was flooded in a depth of about 3 cm. Next day, each wettable powder containing each of Compounds of the present invention and Reference Compounds as the active ingredient was diluted with water and the diluted solution was applied so as to give each dose (40, 20, 10 or 5 g./are) of the active ingredient by a drop treatment under the flooded surface.

For three days after the treatment, a leaching loss of water was given at a rate of 3 cm/day and the pot was kept in a greenhouse.

Twenty one days after the treatment, survival quantities of the plants were measured to find herbicidal effects to weeds. The results are shown in Table 2. Herbicidal effects are rated by the following equation and ratings.

$$\left(1 - \frac{\text{Survival terrestrial weed weight in treated pot}}{\text{Survival terrestrial weed in non-treated pot}}\right) \times 100 = Y(\%)$$

| Herbicidal effect rating | Y (%) |
|---|---|
| 0 | 0–5 |
| 1 | 5–30 |
| 2 | 30–50 |
| 3 | 50–70 |
| 4 | 70–90 |
| 5 | 90–100 |

In tables, "Dose" means "dose of active ingredient" (g/are).

Test B

In accordance with the experiment of Test A, each test was carried out by using the compounds shown in Table 1. The results are shown in Table 3.

Test C

In accordance with the experiment of Test A, each test was carried out by using the compounds shown in Table 1. The results are shown in Table 4.

TABLE 2

| Compound No. | Dose of active ingredient (g/a) | Herbicidal Effect | | | |
|---|---|---|---|---|---|
| | | B.G. | T.C. | N.W. | H.B. |
| 1 | 40 | 5 | 5 | 5 | 5 |
| | 20 | 5 | 5 | 5 | 5 |

TABLE 2-continued

| Compound No. | Dose of active ingredient (g/a) | Herbicidal Effect B.G. | T.C. | N.W. | H.B. |
|---|---|---|---|---|---|
| 2 | 10 | 4 | 5 | 5 | 5 |
|  | 40 | 5 | 5 | 5 | 5 |
|  | 20 | 4 | 5 | 5 | 5 |
| 3 | 10 | 4 | 5 | 5 | 5 |
|  | 40 | 5 | 5 | 5 | 5 |
|  | 20 | 4 | 5 | 5 | 5 |
| 4 | 10 | 4 | 5 | 4 | 4 |
|  | 40 | 5 | 5 | 5 | 5 |
|  | 20 | 5 | 5 | 5 | 5 |
| 5 | 10 | 4 | 5 | 5 | 5 |
|  | 40 | 5 | 5 | 5 | 5 |
|  | 20 | 5 | 5 | 5 | 5 |
| 6 | 10 | 5 | 5 | 5 | 4 |
|  | 40 | 5 | 5 | 5 | 5 |
|  | 20 | 4 | 5 | 5 | 5 |
| 7 | 10 | 4 | 5 | 4 | 4 |
|  | 40 | 5 | 5 | 5 | 5 |
|  | 20 | 5 | 5 | 5 | 5 |
| 8 | 10 | 3 | 5 | 5 | 4 |
|  | 40 | 4 | 5 | 5 | 5 |
|  | 20 | 4 | 5 | 5 | 5 |
| 9 | 10 | 4 | 5 | 5 | 4 |
|  | 40 | 5 | 5 | 5 | 5 |
|  | 20 | 4 | 5 | 5 | 5 |
| 10 | 10 | 4 | 5 | 5 | 4 |
|  | 40 | 5 | 5 | 5 | 5 |
|  | 20 | 4 | 5 | 5 | 5 |
| 11 | 10 | 4 | 5 | 5 | 3 |
|  | 40 | 5 | 5 | 5 | 5 |
|  | 20 | 4 | 5 | 5 | 4 |
| 12 | 10 | 4 | 5 | 5 | 3 |
|  | 40 | 5 | 5 | 5 | 5 |
|  | 20 | 5 | 5 | 5 | 4 |
| 13 | 10 | 4 | 5 | 5 | 4 |
|  | 40 | 5 | 5 | 5 | 5 |
|  | 20 | 5 | 5 | 5 | 5 |
| 14 | 10 | 4 | 5 | 4 | 4 |
|  | 40 | 5 | 5 | 5 | 5 |
|  | 20 | 5 | 5 | 5 | 5 |
| 15 | 10 | 4 | 5 | 5 | 4 |
|  | 40 | 5 | 5 | 5 | 5 |
|  | 20 | 5 | 5 | 5 | 5 |
| 16 | 10 | 5 | 5 | 5 | 5 |
|  | 20 | 5 | 5 | 5 | 5 |
|  | 10 | 5 | 5 | 5 | 5 |
|  | 5 | 5 | 5 | 5 | 5 |
| 17 | 20 | 5 | 5 | 5 | 5 |
|  | 10 | 5 | 5 | 5 | 5 |
|  | 5 | 5 | 5 | 5 | 4 |
| 18 | 20 | 5 | 5 | 5 | 5 |
|  | 10 | 5 | 5 | 5 | 5 |
|  | 5 | 5 | 5 | 5 | 5 |
| 19 | 20 | 5 | 5 | 5 | 5 |
|  | 10 | 5 | 5 | 5 | 5 |
|  | 5 | 4 | 5 | 5 | 5 |
| 20 | 20 | 5 | 5 | 5 | 5 |
|  | 10 | 5 | 5 | 5 | 5 |
|  | 5 | 4 | 5 | 5 | 5 |
| 21 | 20 | 5 | 5 | 5 | 5 |
|  | 10 | 5 | 5 | 5 | 5 |
|  | 5 | 5 | 5 | 5 | 5 |
| 22 | 20 | 5 | 5 | 5 | 5 |
|  | 10 | 5 | 5 | 5 | 5 |
|  | 5 | 5 | 5 | 5 | 5 |
| 23 | 20 | 5 | 5 | 5 | 5 |
|  | 10 | 5 | 5 | 5 | 5 |
|  | 5 | 5 | 5 | 5 | 5 |
| 24 | 20 | 5 | 5 | 5 | 5 |
|  | 10 | 5 | 5 | 5 | 5 |
|  | 5 | 5 | 5 | 5 | 5 |
| 25 | 20 | 5 | 5 | 5 | 5 |
|  | 10 | 5 | 5 | 5 | 5 |
|  | 5 | 5 | 5 | 5 | 5 |
| 26 | 40 | 5 | 5 | 5 | 5 |
|  | 20 | 5 | 5 | 5 | 5 |
|  | 10 | 5 | 5 | 5 | 5 |
| 27 | 20 | 5 | 5 | 5 | 5 |
|  | 10 | 5 | 5 | 5 | 5 |
|  | 5 | 5 | 5 | 5 | 5 |
| 28 | 40 | 5 | 5 | 5 | 5 |
|  | 20 | 5 | 5 | 5 | 5 |
|  | 10 | 4 | 5 | 5 | 5 |
| 29 | 40 | 5 | 5 | 5 | 5 |
|  | 20 | 5 | 5 | 5 | 5 |
|  | 10 | 5 | 5 | 5 | 5 |
| 30 | 40 | 5 | 5 | 5 | 5 |
|  | 20 | 5 | 5 | 5 | 5 |
|  | 10 | 5 | 5 | 5 | 5 |
| 31 | 40 | 5 | 5 | 5 | 5 |
|  | 20 | 5 | 5 | 5 | 5 |
|  | 10 | 3 | 5 | 5 | 4 |
| 32 | 40 | 5 | 5 | 5 | 5 |
|  | 20 | 5 | 5 | 5 | 5 |
|  | 10 | 5 | 5 | 5 | 5 |
| 33 | 40 | 5 | 5 | 5 | 5 |
|  | 20 | 5 | 5 | 5 | 5 |
|  | 10 | 5 | 5 | 5 | 5 |
| 34 | 40 | 5 | 5 | 5 | 5 |
|  | 20 | 5 | 5 | 5 | 4 |
|  | 10 | 5 | 5 | 5 | 4 |
| 35 | 40 | 5 | 5 | 5 | 5 |
|  | 20 | 5 | 5 | 5 | 5 |
|  | 10 | 5 | 5 | 5 | 5 |
| 36 | 40 | 5 | 5 | 5 | 5 |
|  | 20 | 4 | 5 | 5 | 5 |
|  | 10 | 3 | 5 | 4 | 3 |
| 37 | 40 | 5 | 5 | 5 | 5 |
|  | 20 | 5 | 5 | 5 | 5 |
|  | 10 | 5 | 5 | 5 | 4 |
| 38 | 40 | 5 | 5 | 5 | 5 |
|  | 20 | 5 | 5 | 5 | 4 |
|  | 10 | 5 | 5 | 5 | 4 |
| 39 | 40 | 5 | 5 | 5 | 5 |
|  | 20 | 5 | 5 | 5 | 5 |
|  | 10 | 5 | 5 | 5 | 4 |
| 40 | 20 | 5 | 5 | 5 | 5 |
|  | 10 | 5 | 5 | 5 | 5 |
|  | 5 | 5 | 5 | 5 | 5 |
| 41 | 40 | 5 | 5 | 5 | 5 |
|  | 20 | 5 | 5 | 5 | 5 |
|  | 10 | 4 | 5 | 5 | 4 |
| 42 | 40 | 5 | 5 | 5 | 5 |
|  | 20 | 5 | 5 | 5 | 5 |
|  | 10 | 4 | 5 | 5 | 4 |
| 43 | 40 | 5 | 5 | 5 | 5 |
|  | 20 | 5 | 5 | 5 | 4 |
|  | 10 | 4 | 5 | 5 | 5 |
| 44 | 20 | 5 | 5 | 5 | 5 |
|  | 10 | 5 | 5 | 5 | 5 |
|  | 5 | 5 | 5 | 5 | 5 |
| 45 | 20 | 5 | 5 | 5 | 5 |
|  | 10 | 5 | 5 | 5 | 5 |
|  | 5 | 5 | 5 | 5 | 5 |
| 46 | 20 | 5 | 5 | 5 | 5 |
|  | 10 | 5 | 5 | 5 | 5 |
|  | 5 | 5 | 5 | 5 | 5 |
| 47 | 40 | 5 | 5 | 5 | 5 |
|  | 20 | 5 | 5 | 5 | 5 |
|  | 10 | 5 | 5 | 5 | 4 |
| 48 | 20 | 5 | 5 | 5 | 5 |
|  | 10 | 5 | 5 | 5 | 4 |
|  | 5 | 5 | 5 | 5 | 4 |
| 49 | 40 | 5 | 5 | 5 | 5 |
|  | 20 | 5 | 5 | 5 | 4 |
|  | 10 | 3 | 5 | 4 | 3 |
| 50 | 40 | 5 | 5 | 5 | 5 |
|  | 20 | 5 | 5 | 5 | 5 |
|  | 10 | 5 | 5 | 5 | 3 |
| 51 | 40 | 5 | 5 | 5 | 4 |
|  | 20 | 4 | 5 | 5 | 4 |
|  | 10 | 4 | 5 | 4 | 3 |
| 52 | 40 | 4 | 5 | 5 | 5 |
|  | 20 | 4 | 5 | 5 | 5 |
|  | 10 | 3 | 5 | 5 | 3 |

TABLE 2-continued

| Compound No. | Dose of active ingredient (g/a) | Herbicidal Effect B.G. | T.C. | N.W. | H.B. |
|---|---|---|---|---|---|
| 53 | 20 | 5 | 5 | 5 | 5 |
|  | 10 | 5 | 5 | 5 | 5 |
|  | 5 | 5 | 5 | 5 | 5 |
| 54 | 40 | 5 | 5 | 5 | 5 |
|  | 20 | 5 | 5 | 5 | 5 |
|  | 10 | 5 | 5 | 5 | 4 |
| 55 | 40 | 5 | 5 | 5 | 5 |
|  | 20 | 4 | 5 | 5 | 5 |
|  | 10 | 4 | 5 | 5 | 3 |
| 56 | 40 | 5 | 5 | 5 | 5 |
|  | 20 | 4 | 5 | 5 | 5 |
|  | 10 | 3 | 5 | 5 | 3 |
| 57 | 20 | 5 | 5 | 5 | 5 |
|  | 10 | 5 | 5 | 5 | 5 |
|  | 5 | 5 | 5 | 5 | 5 |
| 58 | 20 | 5 | 5 | 5 | 5 |
|  | 10 | 5 | 5 | 5 | 5 |
|  | 5 | 5 | 5 | 5 | 5 |
| 59 | 20 | 5 | 5 | 5 | 5 |
|  | 10 | 5 | 5 | 5 | 5 |
|  | 5 | 5 | 5 | 5 | 5 |
| 60 | 20 | 5 | 5 | 5 | 5 |
|  | 10 | 5 | 5 | 5 | 5 |
|  | 5 | 5 | 5 | 5 | 4 |
| 61 | 20 | 5 | 5 | 5 | 5 |
|  | 10 | 5 | 5 | 5 | 5 |
|  | 5 | 5 | 5 | 5 | 5 |
| 62 | 20 | 5 | 5 | 5 | 5 |
|  | 10 | 5 | 5 | 5 | 5 |
|  | 5 | 5 | 5 | 5 | 5 |
| 63 | 40 | 5 | 5 | 5 | 5 |
|  | 20 | 5 | 5 | 5 | 5 |
|  | 10 | 5 | 5 | 5 | 3 |
| 64 | 40 | 5 | 5 | 5 | 5 |
|  | 20 | 5 | 5 | 5 | 5 |
|  | 10 | 5 | 5 | 5 | 4 |
| 64 | 40 | 5 | 5 | 5 | 5 |
|  | 20 | 5 | 5 | 5 | 4 |
|  | 10 | 4 | 5 | 4 | 3 |
| 66 | 40 | 5 | 5 | 5 | 5 |
|  | 20 | 5 | 5 | 5 | 4 |
|  | 10 | 4 | 5 | 5 | 4 |
| 67 | 40 | 5 | 5 | 5 | 5 |
|  | 20 | 5 | 5 | 5 | 5 |
|  | 10 | 5 | 5 | 5 | 3 |
| 68 | 40 | 5 | 5 | 5 | 5 |
|  | 20 | 5 | 5 | 5 | 5 |
|  | 10 | 5 | 5 | 5 | 5 |
| 69 | 40 | 5 | 5 | 5 | 5 |
|  | 20 | 5 | 5 | 5 | 4 |
|  | 10 | 5 | 5 | 5 | 4 |
| 70 | 40 | 5 | 5 | 5 | 5 |
|  | 20 | 5 | 5 | 5 | 5 |
|  | 10 | 4 | 5 | 5 | 4 |
| 71 | 40 | 5 | 5 | 5 | 5 |
|  | 20 | 5 | 5 | 5 | 4 |
|  | 10 | 5 | 5 | 5 | 3 |
| 72 | 40 | 5 | 5 | 5 | 5 |
|  | 20 | 4 | 5 | 5 | 4 |
|  | 10 | 3 | 5 | 4 | 3 |
| 73 | 40 | 5 | 5 | 5 | 4 |
|  | 20 | 5 | 5 | 5 | 5 |
|  | 10 | 5 | 5 | 5 | 4 |
| 74 | 40 | 5 | 5 | 5 | 5 |
|  | 20 | 5 | 5 | 5 | 5 |
|  | 10 | 5 | 5 | 5 | 4 |
| 75 | 40 | 5 | 5 | 5 | 5 |
|  | 20 | 5 | 5 | 5 | 5 |
|  | 10 | 5 | 5 | 5 | 4 |
| 76 | 40 | 5 | 5 | 5 | 4 |
|  | 20 | 5 | 5 | 5 | 4 |
|  | 10 | 3 | 5 | 5 | 4 |
| 77 | 40 | 5 | 5 | 5 | 4 |
|  | 20 | 5 | 5 | 5 | 4 |
|  | 10 | 4 | 5 | 5 | 4 |
| 78 | 40 | 5 | 5 | 5 | 4 |
|  | 20 | 4 | 5 | 5 | 4 |
|  | 10 | 4 | 5 | 4 | 3 |
| 79 | 40 | 5 | 5 | 5 | 5 |
|  | 20 | 5 | 5 | 5 | 4 |
|  | 10 | 5 | 5 | 5 | 4 |
| 80 | 40 | 5 | 5 | 5 | 5 |
|  | 20 | 5 | 5 | 5 | 5 |
|  | 10 | 4 | 5 | 5 | 3 |
| 81 | 40 | 5 | 5 | 5 | 5 |
|  | 20 | 4 | 5 | 5 | 4 |
|  | 10 | 4 | 5 | 4 | 3 |
| 82 | 40 | 5 | 5 | 5 | 5 |
|  | 20 | 5 | 5 | 5 | 5 |
|  | 10 | 5 | 5 | 5 | 4 |
| 83 | 40 | 5 | 5 | 5 | 5 |
|  | 20 | 4 | 5 | 5 | 5 |
|  | 10 | 3 | 5 | 5 | 3 |
| 84 | 40 | 5 | 5 | 5 | 5 |
|  | 20 | 5 | 5 | 5 | 5 |
|  | 10 | 4 | 5 | 5 | 4 |
| 85 | 40 | 5 | 5 | 5 | 5 |
|  | 20 | 5 | 5 | 5 | 5 |
|  | 10 | 5 | 5 | 5 | 4 |
| 86 | 40 | 5 | 5 | 5 | 5 |
|  | 20 | 5 | 5 | 5 | 5 |
|  | 10 | 4 | 5 | 5 | 5 |
| 87 | 20 | 5 | 5 | 5 | 5 |
|  | 10 | 5 | 5 | 5 | 5 |
|  | 5 | 5 | 5 | 5 | 5 |
| 88 | 20 | 5 | 5 | 5 | 5 |
|  | 10 | 5 | 5 | 5 | 5 |
|  | 5 | 5 | 5 | 5 | 5 |
| 89 | 20 | 5 | 5 | 5 | 5 |
|  | 10 | 5 | 5 | 5 | 5 |
|  | 5 | 5 | 5 | 5 | 5 |
| 90 | 20 | 5 | 5 | 5 | 5 |
|  | 10 | 5 | 5 | 5 | 5 |
|  | 5 | 5 | 5 | 5 | 5 |
| 91 | 20 | 5 | 5 | 5 | 5 |
|  | 10 | 5 | 5 | 5 | 5 |
|  | 5 | 5 | 5 | 5 | 5 |
| 92 | 20 | 5 | 5 | 5 | 5 |
|  | 10 | 5 | 5 | 5 | 5 |
|  | 5 | 5 | 5 | 5 | 5 |
| 93 | 20 | 5 | 5 | 5 | 5 |
|  | 10 | 5 | 5 | 5 | 5 |
|  | 5 | 5 | 5 | 5 | 5 |
| 94 | 20 | 5 | 5 | 5 | 5 |
|  | 10 | 5 | 5 | 5 | 5 |
|  | 5 | 5 | 5 | 5 | 5 |
| 95 | 40 | 5 | 5 | 5 | 5 |
|  | 20 | 4 | 5 | 5 | 4 |
|  | 10 | 4 | 5 | 4 | 3 |
| 96 | 40 | 5 | 5 | 5 | 4 |
|  | 20 | 4 | 5 | 5 | 4 |
|  | 10 | 3 | 5 | 5 | 3 |
| 97 | 40 | 5 | 5 | 5 | 5 |
|  | 20 | 5 | 5 | 5 | 4 |
|  | 10 | 5 | 5 | 5 | 4 |
| 98 | 40 | 5 | 5 | 5 | 5 |
|  | 20 | 5 | 5 | 5 | 4 |
|  | 10 | 4 | 5 | 5 | 5 |
| 99 | 40 | 5 | 5 | 5 | 5 |
|  | 20 | 5 | 5 | 5 | 5 |
|  | 10 | 5 | 5 | 5 | 5 |
| 100 | 40 | 5 | 5 | 5 | 5 |
|  | 20 | 5 | 5 | 5 | 5 |
|  | 10 | 5 | 5 | 5 | 5 |
| 150 | 40 | 5 | 5 | 5 | 5 |
|  | 20 | 5 | 5 | 5 | 4 |
|  | 10 | 4 | 5 | 5 | 4 |
| 151 | 40 | 5 | 5 | 5 | 5 |
|  | 20 | 5 | 5 | 5 | 5 |
|  | 10 | 4 | 5 | 5 | 3 |
| 152 | 40 | 5 | 5 | 5 | 5 |
|  | 20 | 5 | 5 | 5 | 5 |
|  | 10 | 3 | 5 | 5 | 4 |
| 153 | 40 | 5 | 5 | 5 | 5 |

TABLE 2-continued

| Compound No. | Dose of active ingredient (g/a) | Herbicidal Effect B.G. | T.C. | N.W. | H.B. |
|---|---|---|---|---|---|
|  | 20 | 4 | 5 | 5 | 5 |
|  | 10 | 4 | 5 | 4 | 3 |
| 154 | 40 | 4 | 5 | 5 | 5 |
|  | 20 | 4 | 5 | 5 | 5 |
|  | 10 | 4 | 5 | 5 | 4 |
| 155 | 40 | 4 | 5 | 5 | 5 |
|  | 20 | 4 | 5 | 5 | 4 |
|  | 10 | 3 | 5 | 5 | 4 |
| 156 | 40 | 5 | 5 | 5 | 5 |
|  | 20 | 5 | 5 | 5 | 5 |
|  | 10 | 5 | 5 | 5 | 4 |
| 157 | 40 | 5 | 5 | 5 | 5 |
|  | 20 | 5 | 5 | 5 | 5 |
|  | 10 | 5 | 5 | 5 | 4 |
| 158 | 40 | 5 | 5 | 5 | 5 |
|  | 20 | 5 | 5 | 5 | 5 |
|  | 10 | 5 | 5 | 5 | 4 |
| 159 | 40 | 5 | 5 | 5 | 5 |
|  | 20 | 5 | 5 | 5 | 5 |
|  | 10 | 5 | 5 | 5 | 4 |
| 160 | 40 | 5 | 5 | 5 | 5 |
|  | 20 | 5 | 5 | 5 | 4 |
|  | 10 | 5 | 5 | 5 | 4 |
| 161 | 40 | 5 | 5 | 5 | 5 |
|  | 20 | 4 | 5 | 5 | 5 |
|  | 10 | 3 | 5 | 5 | 3 |
| 162 | 20 | 5 | 5 | 5 | 5 |
|  | 10 | 5 | 5 | 5 | 5 |
|  | 5 | 5 | 5 | 5 | 5 |
| 163 | 20 | 5 | 5 | 5 | 5 |
|  | 10 | 5 | 5 | 5 | 5 |
|  | 5 | 5 | 5 | 5 | 5 |
| 164 | 20 | 5 | 5 | 5 | 5 |
|  | 10 | 5 | 5 | 5 | 5 |
|  | 5 | 5 | 5 | 5 | 4 |
| 165 | 40 | 5 | 5 | 5 | 5 |
|  | 20 | 4 | 5 | 5 | 4 |
|  | 10 | 4 | 5 | 5 | 4 |
| 166 | 40 | 5 | 5 | 5 | 5 |
|  | 20 | 5 | 5 | 5 | 5 |
|  | 10 | 5 | 5 | 5 | 4 |
| 167 | 40 | 5 | 5 | 5 | 5 |
|  | 20 | 5 | 5 | 5 | 5 |
|  | 10 | 5 | 5 | 5 | 3 |
| 168 | 40 | 5 | 5 | 5 | 5 |
|  | 20 | 4 | 5 | 5 | 4 |
|  | 10 | 4 | 4 | 4 | 3 |
| 169 | 40 | 5 | 5 | 5 | 5 |
|  | 20 | 4 | 5 | 5 | 5 |
|  | 10 | 4 | 5 | 4 | 3 |
| 170 | 40 | 5 | 5 | 5 | 5 |
|  | 20 | 4 | 5 | 5 | 4 |
|  | 10 | 3 | 5 | 5 | 4 |
| 171 | 40 | 5 | 5 | 5 | 5 |
|  | 20 | 5 | 5 | 5 | 4 |
|  | 10 | 4 | 5 | 5 | 4 |
| 172 | 40 | 5 | 5 | 5 | 5 |
|  | 20 | 5 | 5 | 5 | 5 |
|  | 10 | 5 | 5 | 5 | 4 |
| 173 | 40 | 5 | 5 | 5 | 5 |
|  | 20 | 5 | 5 | 5 | 5 |
|  | 10 | 5 | 5 | 5 | 5 |
| 174 | 40 | 5 | 5 | 5 | 5 |
|  | 20 | 5 | 5 | 5 | 5 |
|  | 10 | 5 | 5 | 5 | 5 |
| 175 | 40 | 5 | 5 | 5 | 5 |
|  | 20 | 5 | 5 | 5 | 5 |
|  | 10 | 5 | 5 | 5 | 5 |
| 176 | 40 | 5 | 5 | 5 | 5 |
|  | 20 | 5 | 5 | 5 | 5 |
|  | 10 | 5 | 5 | 5 | 5 |
| 177 | 40 | 5 | 5 | 5 | 5 |
|  | 20 | 5 | 5 | 5 | 5 |
|  | 10 | 5 | 5 | 5 | 4 |
| 178 | 40 | 5 | 5 | 5 | 5 |
|  | 20 | 5 | 5 | 5 | 5 |
|  | 10 | 4 | 5 | 5 | 4 |
| 179 | 40 | 5 | 5 | 5 | 5 |
|  | 20 | 5 | 5 | 5 | 4 |
|  | 10 | 5 | 5 | 5 | 4 |
| 180 | 40 | 5 | 5 | 5 | 5 |
|  | 20 | 5 | 5 | 5 | 5 |
|  | 10 | 4 | 5 | 5 | 3 |
| 181 | 40 | 5 | 5 | 5 | 5 |
|  | 20 | 4 | 5 | 5 | 4 |
|  | 10 | 4 | 5 | 5 | 3 |
| 182 | 40 | 5 | 5 | 5 | 5 |
|  | 20 | 5 | 5 | 5 | 5 |
|  | 10 | 5 | 5 | 5 | 4 |
| 183 | 40 | 5 | 5 | 5 | 5 |
|  | 20 | 5 | 5 | 5 | 4 |
|  | 10 | 5 | 5 | 5 | 4 |
| 184 | 40 | 5 | 5 | 5 | 5 |
|  | 20 | 5 | 5 | 5 | 5 |
|  | 10 | 4 | 5 | 5 | 3 |
| 185 | 40 | 5 | 5 | 5 | 5 |
|  | 20 | 5 | 5 | 5 | 4 |
|  | 10 | 4 | 5 | 5 | 3 |
| 186 | 40 | 5 | 5 | 5 | 5 |
|  | 20 | 4 | 5 | 5 | 4 |
|  | 10 | 3 | 5 | 4 | 3 |
| 187 | 40 | 5 | 5 | 5 | 5 |
|  | 20 | 5 | 5 | 5 | 5 |
|  | 10 | 5 | 5 | 5 | 3 |
| 188 | 40 | 5 | 5 | 5 | 5 |
|  | 20 | 5 | 5 | 5 | 4 |
|  | 10 | 5 | 5 | 5 | 4 |
| 189 | 40 | 5 | 5 | 5 | 5 |
|  | 20 | 5 | 5 | 5 | 5 |
|  | 10 | 5 | 5 | 5 | 4 |
| 190 | 40 | 5 | 5 | 5 | 5 |
|  | 20 | 5 | 5 | 5 | 5 |
|  | 10 | 5 | 5 | 5 | 5 |
| 191 | 40 | 5 | 5 | 5 | 5 |
|  | 20 | 5 | 5 | 5 | 4 |
|  | 10 | 3 | 4 | 5 | 3 |
| 192 | 40 | 5 | 5 | 5 | 4 |
|  | 20 | 4 | 5 | 5 | 4 |
|  | 10 | 4 | 5 | 4 | 3 |
| 193 | 40 | 5 | 5 | 5 | 5 |
|  | 20 | 4 | 5 | 5 | 4 |
|  | 10 | 3 | 5 | 4 | 3 |
| 194 | 20 | 5 | 5 | 5 | 5 |
|  | 10 | 5 | 5 | 5 | 5 |
|  | 5 | 5 | 5 | 5 | 5 |
| 195 | 20 | 5 | 5 | 5 | 5 |
|  | 10 | 5 | 5 | 5 | 5 |
|  | 5 | 5 | 5 | 5 | 4 |
| 196 | 40 | 5 | 5 | 5 | 5 |
|  | 20 | 4 | 5 | 5 | 5 |
|  | 10 | 3 | 5 | 5 | 4 |
| 197 | 40 | 5 | 5 | 5 | 5 |
|  | 20 | 4 | 5 | 5 | 4 |
|  | 10 | 4 | 5 | 4 | 3 |
| 198 | 40 | 5 | 5 | 5 | 5 |
|  | 20 | 4 | 5 | 5 | 4 |
|  | 10 | 3 | 5 | 4 | 3 |
| 199 | 40 | 4 | 5 | 5 | 5 |
|  | 20 | 4 | 5 | 5 | 4 |
|  | 10 | 4 | 5 | 5 | 3 |
| 200 | 40 | 5 | 5 | 5 | 5 |
|  | 20 | 4 | 5 | 5 | 4 |
|  | 10 | 3 | 5 | 5 | 4 |
| Reference A | 40 | 5 | 5 | 5 | 5 |
|  | 20 | 4 | 4 | 4 | 4 |
|  | 10 | 3 | 3 | 4 | 2 |
| Reference B | 40 | 5 | 5 | 5 | 5 |
|  | 20 | 3 | 5 | 4 | 3 |
|  | 10 | 3 | 3 | 3 | 3 |
| Reference C | 20 | 5 | 5 | 2 | 4 |
|  | 10 | 4 | 4 | 1 | 2 |
|  | 5 | 2 | 3 | 0 | 0 |
| Reference D | 40 | 5 | 4 | 2 | 5 |
|  | 20 | 4 | 3 | 0 | 4 |

TABLE 2-continued

| Compound No. | Dose of active ingredient (g/a) | Herbicidal Effect B.G. | T.C. | N.W. | H.B. |
|---|---|---|---|---|---|
|  | 10 | 1 | 2 | 0 | 2 |
| Non-treatment | 0 | 0 | 0 | 0 | 0 |

TABLE 3

| Compound No. | Dose of active ingredient (g/a) | Herbicidal Effect B.G. | T.C. | N.W. | H.B. |
|---|---|---|---|---|---|
| 227 | 40 | 5 | 5 | 5 | 5 |
|  | 20 | 4 | 5 | 5 | 5 |
|  | 10 | 4 | 5 | 5 | 4 |
| 228 | 20 | 5 | 5 | 5 | 5 |
|  | 10 | 5 | 5 | 5 | 5 |
|  | 5 | 5 | 5 | 5 | 5 |
| 229 | 20 | 5 | 5 | 5 | 5 |
|  | 10 | 5 | 5 | 5 | 5 |
|  | 5 | 5 | 5 | 5 | 5 |
| 230 | 20 | 5 | 5 | 5 | 5 |
|  | 10 | 5 | 5 | 5 | 5 |
|  | 5 | 5 | 5 | 5 | 5 |
| 231 | 20 | 5 | 5 | 5 | 5 |
|  | 10 | 5 | 5 | 5 | 5 |
|  | 5 | 5 | 5 | 5 | 5 |
| 232 | 40 | 5 | 5 | 5 | 5 |
|  | 20 | 5 | 5 | 5 | 5 |
|  | 10 | 4 | 5 | 5 | 4 |
| 233 | 20 | 5 | 5 | 5 | 5 |
|  | 10 | 5 | 5 | 5 | 5 |
|  | 5 | 5 | 5 | 5 | 4 |
| 234 | 20 | 5 | 5 | 5 | 5 |
|  | 10 | 5 | 5 | 5 | 5 |
|  | 5 | 5 | 5 | 5 | 5 |
| 235 | 20 | 5 | 5 | 5 | 5 |
|  | 10 | 5 | 5 | 5 | 5 |
|  | 5 | 4 | 5 | 5 | 5 |
| 236 | 20 | 5 | 5 | 5 | 5 |
|  | 10 | 5 | 5 | 5 | 5 |
|  | 5 | 5 | 5 | 5 | 4 |
| 237 | 40 | 5 | 5 | 5 | 5 |
|  | 20 | 5 | 5 | 5 | 5 |
|  | 10 | 5 | 5 | 5 | 5 |
| 238 | 40 | 5 | 5 | 5 | 5 |
|  | 20 | 5 | 5 | 5 | 5 |
|  | 10 | 5 | 5 | 5 | 5 |
| Reference A | 40 | 5 | 5 | 5 | 5 |
|  | 20 | 4 | 4 | 5 | 4 |
|  | 10 | 3 | 4 | 3 | 3 |
| Reference B | 40 | 5 | 5 | 5 | 5 |
|  | 20 | 4 | 5 | 4 | 4 |
|  | 10 | 3 | 4 | 3 | 2 |
| Reference C | 20 | 5 | 5 | 3 | 3 |
|  | 10 | 4 | 5 | 1 | 0 |
|  | 5 | 2 | 4 | 0 | 0 |
| Reference D | 40 | 5 | 4 | 2 | 5 |
|  | 20 | 4 | 4 | 0 | 4 |
|  | 10 | 1 | 2 | 0 | 3 |
| Non-treatment | — | 0 | 0 | 0 | 0 |

TABLE 4

| Compound No. | Dose of active ingredient (g/a) | Herbicidal Effect B.G. | T.C. | N.W. | H.B. |
|---|---|---|---|---|---|
| 239 | 20 | 5 | 5 | 5 | 5 |
|  | 10 | 5 | 5 | 5 | 5 |
|  | 5 | 5 | 5 | 5 | 4 |
| 240 | 20 | 5 | 5 | 5 | 5 |
|  | 10 | 5 | 5 | 5 | 5 |
|  | 5 | 5 | 5 | 5 | 5 |
| 241 | 20 | 5 | 5 | 5 | 5 |
|  | 10 | 5 | 5 | 5 | 5 |
|  | 5 | 5 | 5 | 5 | 5 |

TABLE 4-continued

| Compound No. | Dose of active ingredient (g/a) | Herbicidal Effect B.G. | T.C. | N.W. | H.B. |
|---|---|---|---|---|---|
| 242 | 20 | 5 | 5 | 5 | 5 |
|  | 10 | 5 | 5 | 5 | 5 |
|  | 5 | 5 | 5 | 5 | 5 |
| 243 | 20 | 5 | 5 | 5 | 5 |
|  | 10 | 5 | 5 | 5 | 5 |
|  | 5 | 5 | 5 | 5 | 4 |
| 244 | 20 | 5 | 5 | 5 | 5 |
|  | 10 | 5 | 5 | 5 | 5 |
|  | 5 | 5 | 5 | 5 | 5 |
| 245 | 20 | 5 | 5 | 5 | 5 |
|  | 10 | 5 | 5 | 5 | 5 |
|  | 5 | 5 | 5 | 5 | 4 |
| 246 | 20 | 5 | 5 | 5 | 5 |
|  | 10 | 5 | 5 | 5 | 5 |
|  | 5 | 4 | 5 | 5 | 4 |
| 247 | 20 | 5 | 5 | 5 | 5 |
|  | 10 | 5 | 5 | 5 | 5 |
|  | 5 | 5 | 5 | 5 | 4 |
| 248 | 20 | 5 | 5 | 5 | 5 |
|  | 10 | 5 | 5 | 5 | 5 |
|  | 5 | 5 | 5 | 5 | 4 |
| 249 | 20 | 5 | 5 | 5 | 5 |
|  | 10 | 5 | 5 | 5 | 5 |
|  | 5 | 5 | 5 | 5 | 4 |
| 250 | 20 | 5 | 5 | 5 | 5 |
|  | 10 | 5 | 5 | 5 | 5 |
|  | 5 | 4 | 5 | 5 | 4 |
| 251 | 20 | 5 | 5 | 5 | 5 |
|  | 10 | 5 | 5 | 5 | 5 |
|  | 5 | 5 | 5 | 5 | 5 |
| 252 | 40 | 5 | 5 | 5 | 5 |
|  | 20 | 5 | 5 | 5 | 4 |
|  | 10 | 4 | 5 | 5 | 4 |
| 253 | 20 | 5 | 5 | 5 | 5 |
|  | 10 | 5 | 5 | 5 | 5 |
|  | 5 | 5 | 5 | 5 | 4 |
| 254 | 20 | 5 | 5 | 5 | 5 |
|  | 10 | 5 | 5 | 5 | 4 |
|  | 5 | 5 | 5 | 5 | 4 |
| 255 | 20 | 5 | 5 | 5 | 5 |
|  | 10 | 5 | 5 | 5 | 5 |
|  | 5 | 4 | 5 | 5 | 4 |
| 256 | 40 | 5 | 5 | 5 | 5 |
|  | 20 | 5 | 5 | 5 | 5 |
|  | 10 | 4 | 5 | 5 | 4 |
| 257 | 20 | 5 | 5 | 5 | 5 |
|  | 10 | 5 | 5 | 5 | 4 |
|  | 5 | 4 | 5 | 5 | 4 |
| 258 | 40 | 5 | 5 | 5 | 5 |
|  | 20 | 5 | 5 | 5 | 5 |
|  | 10 | 5 | 5 | 5 | 4 |
| 259 | 20 | 5 | 5 | 5 | 5 |
|  | 10 | 5 | 5 | 5 | 5 |
|  | 5 | 5 | 5 | 5 | 5 |
| 260 | 40 | 5 | 5 | 5 | 5 |
|  | 20 | 5 | 5 | 5 | 5 |
|  | 10 | 4 | 5 | 5 | 3 |
| 261 | 40 | 5 | 5 | 5 | 5 |
|  | 20 | 5 | 5 | 5 | 5 |
|  | 10 | 4 | 5 | 5 | 3 |
| 262 | 40 | 5 | 5 | 5 | 5 |
|  | 20 | 5 | 5 | 5 | 5 |
|  | 10 | 5 | 5 | 5 | 5 |
| 263 | 20 | 5 | 5 | 5 | 5 |
|  | 10 | 5 | 5 | 5 | 5 |
|  | 5 | 5 | 5 | 5 | 5 |
| 264 | 20 | 5 | 5 | 5 | 5 |
|  | 10 | 5 | 5 | 5 | 5 |
|  | 5 | 4 | 5 | 5 | 4 |
| 265 | 20 | 5 | 5 | 5 | 5 |
|  | 10 | 5 | 5 | 5 | 5 |
|  | 5 | 5 | 5 | 5 | 5 |
| 266 | 20 | 5 | 5 | 5 | 5 |
|  | 10 | 5 | 5 | 5 | 5 |
|  | 5 | 5 | 5 | 5 | 5 |
| 267 | 40 | 5 | 5 | 5 | 5 |
|  | 20 | 5 | 5 | 5 | 5 |

TABLE 4-continued

| Compound No. | Dose of active ingredient (g/a) | Herbicidal Effect | | | |
|---|---|---|---|---|---|
| | | B.G. | T.C. | N.W. | H.B. |
| 268 | 10 | 5 | 5 | 5 | 4 |
| | 20 | 5 | 5 | 5 | 5 |
| | 10 | 5 | 5 | 5 | 5 |
| | 5 | 5 | 5 | 5 | 5 |
| 269 | 20 | 5 | 5 | 5 | 5 |
| | 10 | 5 | 5 | 5 | 5 |
| | 5 | 5 | 5 | 5 | 5 |
| 270 | 40 | 5 | 5 | 5 | 5 |
| | 20 | 5 | 5 | 5 | 5 |
| | 10 | 5 | 5 | 5 | 4 |
| 271 | 20 | 5 | 5 | 5 | 5 |
| | 10 | 5 | 5 | 5 | 5 |
| | 5 | 5 | 5 | 5 | 4 |
| 272 | 20 | 5 | 5 | 5 | 5 |
| | 10 | 5 | 5 | 5 | 5 |
| | 5 | 5 | 5 | 5 | 5 |
| 273 | 20 | 5 | 5 | 5 | 5 |
| | 10 | 5 | 5 | 5 | 5 |
| | 5 | 5 | 5 | 5 | 5 |
| 274 | 20 | 5 | 5 | 5 | 5 |
| | 10 | 5 | 5 | 5 | 5 |
| | 5 | 5 | 5 | 5 | 5 |
| 275 | 20 | 5 | 5 | 5 | 5 |
| | 10 | 5 | 5 | 5 | 5 |
| | 5 | 5 | 5 | 5 | 4 |
| 276 | 40 | 5 | 5 | 5 | 5 |
| | 20 | 5 | 5 | 5 | 5 |
| | 10 | 5 | 5 | 5 | 5 |
| 277 | 40 | 5 | 5 | 5 | 5 |
| | 20 | 5 | 5 | 5 | 5 |
| | 10 | 4 | 5 | 5 | 4 |
| 278 | 20 | 5 | 5 | 5 | 5 |
| | 10 | 5 | 5 | 5 | 5 |
| | 5 | 5 | 5 | 5 | 5 |
| 279 | 20 | 5 | 5 | 5 | 5 |
| | 10 | 5 | 5 | 5 | 5 |
| | 5 | 5 | 5 | 5 | 5 |
| 280 | 20 | 5 | 5 | 5 | 5 |
| | 10 | 5 | 5 | 5 | 5 |
| | 5 | 5 | 5 | 5 | 4 |
| 281 | 20 | 5 | 5 | 5 | 5 |
| | 10 | 5 | 5 | 5 | 5 |
| | 5 | 5 | 5 | 5 | 5 |
| 282 | 20 | 5 | 5 | 5 | 5 |
| | 10 | 5 | 5 | 5 | 5 |
| | 5 | 5 | 5 | 5 | 4 |
| 283 | 20 | 5 | 5 | 5 | 5 |
| | 10 | 5 | 5 | 5 | 5 |
| | 5 | 5 | 5 | 5 | 4 |
| 284 | 20 | 5 | 5 | 5 | 5 |
| | 10 | 5 | 5 | 5 | 5 |
| | 5 | 5 | 5 | 5 | 4 |
| 285 | 20 | 5 | 5 | 5 | 5 |
| | 10 | 5 | 5 | 5 | 5 |
| | 5 | 5 | 5 | 5 | 5 |
| 286 | 20 | 5 | 5 | 5 | 5 |
| | 10 | 5 | 5 | 5 | 5 |
| | 5 | 5 | 5 | 5 | 4 |
| 287 | 20 | 5 | 5 | 5 | 5 |
| | 10 | 5 | 5 | 5 | 5 |
| | 5 | 5 | 5 | 5 | 4 |
| 288 | 20 | 5 | 5 | 5 | 5 |
| | 10 | 5 | 5 | 5 | 5 |
| | 5 | 5 | 5 | 5 | 5 |
| 289 | 20 | 5 | 5 | 5 | 5 |
| | 10 | 5 | 5 | 5 | 5 |
| | 5 | 5 | 5 | 5 | 4 |
| 290 | 20 | 5 | 5 | 5 | 5 |
| | 10 | 5 | 5 | 5 | 5 |
| | 5 | 5 | 5 | 5 | 5 |
| 291 | 40 | 5 | 5 | 5 | 5 |
| | 20 | 5 | 5 | 5 | 4 |
| | 10 | 4 | 5 | 5 | 4 |
| 292 | 40 | 5 | 5 | 5 | 5 |
| | 20 | 5 | 5 | 5 | 5 |
| | 10 | 4 | 5 | 5 | 3 |
| 293 | 40 | 5 | 5 | 5 | 5 |
| | 20 | 5 | 5 | 5 | 5 |
| | 10 | 5 | 5 | 5 | 4 |
| 294 | 20 | 5 | 5 | 5 | 5 |
| | 10 | 5 | 5 | 5 | 5 |
| | 5 | 5 | 5 | 5 | 5 |
| 295 | 20 | 5 | 5 | 5 | 5 |
| | 10 | 5 | 5 | 5 | 5 |
| | 5 | 5 | 5 | 5 | 4 |
| 296 | 40 | 5 | 5 | 5 | 5 |
| | 20 | 4 | 5 | 5 | 5 |
| | 10 | 4 | 5 | 5 | 3 |
| 297 | 20 | 5 | 5 | 5 | 5 |
| | 10 | 5 | 5 | 5 | 5 |
| | 5 | 5 | 5 | 5 | 5 |
| 298 | 40 | 5 | 5 | 5 | 5 |
| | 20 | 5 | 5 | 5 | 5 |
| | 10 | 5 | 5 | 5 | 4 |
| 299 | 20 | 5 | 5 | 5 | 5 |
| | 10 | 5 | 5 | 5 | 5 |
| | 5 | 5 | 5 | 5 | 4 |
| 300 | 20 | 5 | 5 | 5 | 5 |
| | 10 | 5 | 5 | 5 | 5 |
| | 5 | 5 | 5 | 5 | 5 |
| 301 | 20 | 5 | 5 | 5 | 5 |
| | 10 | 5 | 5 | 5 | 5 |
| | 5 | 5 | 5 | 5 | 5 |
| 302 | 20 | 5 | 5 | 5 | 5 |
| | 10 | 5 | 5 | 5 | 5 |
| | 5 | 5 | 5 | 5 | 4 |
| 303 | 40 | 5 | 5 | 5 | 5 |
| | 20 | 5 | 5 | 5 | 4 |
| | 10 | 5 | 5 | 5 | 4 |
| 304 | 40 | 5 | 5 | 5 | 5 |
| | 20 | 5 | 5 | 5 | 5 |
| | 10 | 4 | 5 | 5 | 4 |
| 305 | 40 | 5 | 5 | 5 | 5 |
| | 20 | 4 | 5 | 5 | 5 |
| | 10 | 4 | 5 | 5 | 4 |
| 306 | 20 | 5 | 5 | 5 | 5 |
| | 10 | 5 | 5 | 5 | 5 |
| | 5 | 5 | 5 | 5 | 4 |
| 307 | 20 | 5 | 5 | 5 | 5 |
| | 10 | 5 | 5 | 5 | 5 |
| | 5 | 4 | 5 | 5 | 4 |
| 308 | 20 | 5 | 5 | 5 | 5 |
| | 10 | 5 | 5 | 5 | 5 |
| | 5 | 5 | 5 | 5 | 5 |
| 309 | 20 | 5 | 5 | 5 | 5 |
| | 10 | 5 | 5 | 5 | 5 |
| | 5 | 4 | 5 | 5 | 5 |
| 310 | 40 | 5 | 5 | 5 | 5 |
| | 20 | 5 | 5 | 5 | 4 |
| | 10 | 5 | 5 | 5 | 4 |
| 311 | 40 | 5 | 5 | 5 | 5 |
| | 20 | 4 | 5 | 5 | 4 |
| | 10 | 4 | 5 | 5 | 4 |
| 312 | 40 | 5 | 5 | 5 | 5 |
| | 20 | 5 | 5 | 5 | 4 |
| | 10 | 4 | 5 | 5 | 4 |
| 313 | 20 | 5 | 5 | 5 | 5 |
| | 10 | 5 | 5 | 5 | 5 |
| | 5 | 5 | 5 | 5 | 4 |
| 336 | 20 | 5 | 5 | 5 | 5 |
| | 10 | 4 | 5 | 5 | 4 |
| | 5 | 4 | 5 | 5 | 4 |
| 337 | 20 | 5 | 5 | 5 | 5 |
| | 10 | 5 | 5 | 5 | 5 |
| | 5 | 4 | 5 | 5 | 5 |
| 338 | 20 | 5 | 5 | 5 | 5 |
| | 10 | 5 | 5 | 5 | 5 |
| | 5 | 5 | 5 | 5 | 4 |
| 339 | 20 | 5 | 5 | 5 | 5 |
| | 10 | 5 | 5 | 5 | 5 |
| | 5 | 4 | 5 | 5 | 5 |
| 340 | 20 | 5 | 5 | 5 | 5 |
| | 10 | 5 | 5 | 5 | 5 |
| | 5 | 5 | 5 | 5 | 5 |

TABLE 4-continued

| Compound No. | Dose of active ingredient (g/a) | Herbicidal Effect B.G. | T.C. | N.W. | H.B. |
|---|---|---|---|---|---|
| 341 | 20 | 5 | 5 | 5 | 5 |
|  | 10 | 5 | 5 | 5 | 5 |
|  | 5 | 5 | 5 | 5 | 5 |
| 342 | 20 | 5 | 5 | 5 | 5 |
|  | 10 | 5 | 5 | 5 | 5 |
|  | 5 | 5 | 5 | 5 | 4 |
| 343 | 20 | 5 | 5 | 5 | 5 |
|  | 10 | 5 | 5 | 5 | 5 |
|  | 5 | 5 | 5 | 5 | 5 |
| 344 | 20 | 5 | 5 | 5 | 5 |
|  | 10 | 5 | 5 | 5 | 5 |
|  | 5 | 5 | 5 | 5 | 5 |
| 345 | 20 | 5 | 5 | 5 | 5 |
|  | 10 | 5 | 5 | 5 | 5 |
|  | 5 | 5 | 5 | 5 | 5 |
| 346 | 20 | 5 | 5 | 5 | 5 |
|  | 10 | 5 | 5 | 5 | 5 |
|  | 5 | 5 | 5 | 5 | 5 |
| 347 | 20 | 5 | 5 | 5 | 5 |
|  | 10 | 5 | 5 | 5 | 5 |
|  | 5 | 5 | 5 | 5 | 5 |
| 348 | 20 | 5 | 5 | 5 | 5 |
|  | 10 | 5 | 5 | 5 | 5 |
|  | 5 | 5 | 5 | 5 | 5 |
| 349 | 20 | 5 | 5 | 5 | 5 |
|  | 10 | 5 | 5 | 5 | 5 |
|  | 5 | 5 | 5 | 5 | 5 |
| 350 | 20 | 5 | 5 | 5 | 5 |
|  | 10 | 4 | 5 | 5 | 4 |
|  | 5 | 4 | 5 | 4 | 3 |
| 351 | 20 | 5 | 5 | 5 | 4 |
|  | 10 | 5 | 5 | 5 | 4 |
|  | 5 | 3 | 5 | 4 | 3 |
| 352 | 20 | 5 | 5 | 5 | 5 |
|  | 10 | 5 | 5 | 5 | 5 |
|  | 5 | 4 | 5 | 5 | 4 |
| 353 | 20 | 5 | 5 | 5 | 5 |
|  | 10 | 5 | 5 | 5 | 5 |
|  | 5 | 5 | 5 | 5 | 5 |
| 354 | 20 | 5 | 5 | 5 | 5 |
|  | 10 | 5 | 5 | 5 | 5 |
|  | 5 | 4 | 5 | 5 | 5 |
| 355 | 20 | 5 | 5 | 5 | 5 |
|  | 10 | 5 | 5 | 5 | 5 |
|  | 5 | 5 | 5 | 5 | 5 |
| 356 | 20 | 5 | 5 | 5 | 5 |
|  | 10 | 5 | 5 | 5 | 5 |
|  | 5 | 5 | 5 | 5 | 5 |
| 357 | 20 | 5 | 5 | 5 | 5 |
|  | 10 | 5 | 5 | 5 | 5 |
|  | 5 | 5 | 5 | 5 | 5 |
| 358 | 20 | 5 | 5 | 5 | 5 |
|  | 10 | 5 | 5 | 5 | 5 |
|  | 5 | 5 | 5 | 5 | 5 |
| 359 | 20 | 5 | 5 | 5 | 5 |
|  | 10 | 5 | 5 | 5 | 5 |
|  | 5 | 5 | 5 | 5 | 5 |
| 360 | 20 | 5 | 5 | 5 | 5 |
|  | 10 | 5 | 5 | 5 | 5 |
|  | 5 | 4 | 5 | 5 | 5 |
| 361 | 20 | 5 | 5 | 5 | 5 |
|  | 10 | 5 | 5 | 5 | 5 |
|  | 5 | 5 | 5 | 5 | 4 |
| 362 | 20 | 5 | 5 | 5 | 5 |
|  | 10 | 5 | 5 | 5 | 5 |
|  | 5 | 4 | 5 | 5 | 5 |
| 363 | 20 | 5 | 5 | 5 | 5 |
|  | 10 | 5 | 5 | 5 | 5 |
|  | 5 | 5 | 5 | 5 | 5 |
| 364 | 20 | 5 | 5 | 5 | 5 |
|  | 10 | 5 | 5 | 5 | 5 |
|  | 5 | 5 | 5 | 5 | 4 |
| 365 | 20 | 5 | 5 | 5 | 5 |
|  | 10 | 5 | 5 | 5 | 5 |
|  | 5 | 4 | 5 | 5 | 4 |
| 366 | 20 | 5 | 5 | 5 | 5 |
|  | 10 | 5 | 5 | 5 | 5 |
|  | 5 | 5 | 5 | 5 | 5 |
| 367 | 20 | 5 | 5 | 5 | 5 |
|  | 10 | 5 | 5 | 5 | 5 |
|  | 5 | 5 | 5 | 5 | 3 |
| 368 | 20 | 5 | 5 | 5 | 5 |
|  | 10 | 5 | 5 | 5 | 5 |
|  | 5 | 5 | 5 | 5 | 3 |
| 369 | 20 | 5 | 5 | 5 | 5 |
|  | 10 | 5 | 5 | 5 | 5 |
|  | 5 | 5 | 5 | 5 | 5 |
| 370 | 20 | 5 | 5 | 5 | 5 |
|  | 10 | 5 | 5 | 5 | 5 |
|  | 5 | 4 | 5 | 5 | 5 |
| 371 | 20 | 5 | 5 | 5 | 5 |
|  | 10 | 5 | 5 | 5 | 5 |
|  | 5 | 5 | 5 | 5 | 5 |
| 372 | 20 | 5 | 5 | 5 | 5 |
|  | 10 | 5 | 5 | 5 | 5 |
|  | 5 | 5 | 5 | 5 | 5 |
| 373 | 20 | 5 | 5 | 5 | 5 |
|  | 10 | 5 | 5 | 5 | 5 |
|  | 5 | 4 | 5 | 5 | 4 |
| 374 | 20 | 5 | 5 | 5 | 5 |
|  | 10 | 5 | 5 | 5 | 5 |
|  | 5 | 4 | 5 | 5 | 4 |
| 375 | 20 | 5 | 5 | 5 | 5 |
|  | 10 | 5 | 5 | 5 | 5 |
|  | 5 | 4 | 5 | 5 | 3 |
| 376 | 20 | 5 | 5 | 5 | 5 |
|  | 10 | 5 | 5 | 5 | 5 |
|  | 5 | 4 | 5 | 5 | 4 |
| 377 | 20 | 5 | 5 | 5 | 5 |
|  | 10 | 5 | 5 | 5 | 5 |
|  | 5 | 5 | 5 | 5 | 5 |
| 378 | 20 | 5 | 5 | 5 | 5 |
|  | 10 | 5 | 5 | 5 | 5 |
|  | 5 | 5 | 5 | 5 | 5 |
| 379 | 20 | 5 | 5 | 5 | 5 |
|  | 10 | 5 | 5 | 5 | 5 |
|  | 5 | 5 | 5 | 5 | 4 |
| 380 | 20 | 5 | 5 | 5 | 5 |
|  | 10 | 5 | 5 | 5 | 5 |
|  | 5 | 5 | 5 | 5 | 5 |
| 381 | 20 | 5 | 5 | 5 | 5 |
|  | 10 | 5 | 5 | 5 | 5 |
|  | 5 | 5 | 5 | 5 | 5 |
| 382 | 20 | 5 | 5 | 5 | 5 |
|  | 10 | 5 | 5 | 5 | 5 |
|  | 5 | 5 | 5 | 5 | 5 |
| 383 | 20 | 5 | 5 | 5 | 5 |
|  | 10 | 5 | 5 | 5 | 5 |
|  | 5 | 5 | 5 | 5 | 5 |
| 384 | 20 | 5 | 5 | 5 | 5 |
|  | 10 | 5 | 5 | 5 | 5 |
|  | 5 | 5 | 5 | 5 | 5 |
| 385 | 20 | 5 | 5 | 5 | 5 |
|  | 10 | 5 | 5 | 5 | 5 |
|  | 5 | 5 | 5 | 5 | 4 |
| 386 | 20 | 5 | 5 | 5 | 5 |
|  | 10 | 5 | 5 | 5 | 5 |
|  | 5 | 5 | 5 | 5 | 4 |
| 387 | 20 | 5 | 5 | 5 | 5 |
|  | 10 | 5 | 5 | 5 | 5 |
|  | 5 | 5 | 5 | 5 | 5 |
| 388 | 20 | 5 | 5 | 5 | 5 |
|  | 10 | 5 | 5 | 5 | 5 |
|  | 5 | 5 | 5 | 5 | 5 |
| 389 | 20 | 5 | 5 | 5 | 5 |
|  | 10 | 5 | 5 | 5 | 5 |
|  | 5 | 5 | 5 | 5 | 5 |
| 390 | 20 | 5 | 5 | 5 | 5 |
|  | 10 | 5 | 5 | 5 | 5 |
|  | 5 | 5 | 5 | 5 | 5 |
| 391 | 20 | 5 | 5 | 5 | 5 |
|  | 10 | 5 | 5 | 5 | 5 |
|  | 5 | 5 | 5 | 5 | 5 |
| 392 | 20 | 5 | 5 | 5 | 5 |

TABLE 4-continued

| Compound No. | Dose of active ingredient (g/a) | Herbicidal Effect | | | |
|---|---|---|---|---|---|
| | | B.G. | T.C. | N.W. | H.B. |
| | 10 | 5 | 5 | 5 | 5 |
| | 5 | 5 | 5 | 5 | 4 |
| 393 | 20 | 5 | 5 | 5 | 5 |
| | 10 | 5 | 5 | 5 | 5 |
| | 5 | 5 | 5 | 5 | 5 |
| 394 | 20 | 5 | 5 | 5 | 5 |
| | 10 | 5 | 5 | 5 | 5 |
| | 5 | 5 | 5 | 5 | 5 |
| 395 | 20 | 5 | 5 | 5 | 5 |
| | 10 | 5 | 5 | 5 | 5 |
| | 5 | 5 | 5 | 5 | 5 |
| 396 | 20 | 5 | 5 | 5 | 5 |
| | 10 | 5 | 5 | 5 | 4 |
| | 5 | 5 | 5 | 5 | 4 |
| 397 | 20 | 5 | 5 | 5 | 5 |
| | 10 | 5 | 5 | 5 | 5 |
| | 5 | 5 | 5 | 5 | 4 |
| 398 | 20 | 5 | 5 | 5 | 5 |
| | 10 | 5 | 5 | 5 | 5 |
| | 5 | 5 | 5 | 5 | 5 |
| 399 | 20 | 5 | 5 | 5 | 5 |
| | 10 | 5 | 5 | 5 | 5 |
| | 5 | 5 | 5 | 5 | 5 |
| 400 | 20 | 5 | 5 | 5 | 5 |
| | 10 | 5 | 5 | 5 | 5 |
| | 5 | 5 | 5 | 5 | 5 |
| 401 | 20 | 5 | 5 | 5 | 5 |
| | 10 | 5 | 5 | 5 | 5 |
| | 5 | 5 | 5 | 5 | 5 |
| 402 | 20 | 5 | 5 | 5 | 5 |
| | 10 | 5 | 5 | 5 | 5 |
| | 5 | 4 | 5 | 5 | 4 |
| 403 | 20 | 5 | 5 | 5 | 5 |
| | 10 | 5 | 5 | 5 | 5 |
| | 5 | 5 | 5 | 5 | 5 |
| 404 | 20 | 5 | 5 | 5 | 5 |
| | 10 | 5 | 5 | 5 | 5 |
| | 5 | 5 | 5 | 5 | 4 |
| 405 | 20 | 5 | 5 | 5 | 5 |
| | 10 | 4 | 5 | 5 | 5 |
| | 5 | 4 | 5 | 4 | 3 |
| 406 | 20 | 5 | 5 | 5 | 5 |
| | 10 | 5 | 5 | 5 | 5 |
| | 5 | 4 | 5 | 4 | 4 |
| 407 | 20 | 5 | 5 | 5 | 5 |
| | 10 | 5 | 5 | 5 | 5 |
| | 5 | 5 | 5 | 5 | 3 |
| 408 | 20 | 5 | 5 | 5 | 5 |
| | 10 | 5 | 5 | 5 | 5 |
| | 5 | 5 | 5 | 5 | 5 |
| Reference A | 40 | 5 | 5 | 5 | 5 |
| | 20 | 4 | 4 | 5 | 4 |
| | 10 | 3 | 3 | 3 | 2 |
| Reference B | 40 | 5 | 5 | 5 | 5 |
| | 20 | 4 | 5 | 4 | 4 |
| | 10 | 2 | 3 | 3 | 2 |
| Reference C | 20 | 5 | 5 | 3 | 4 |
| | 10 | 4 | 5 | 1 | 2 |
| | 5 | 2 | 3 | 0 | 0 |
| Reference D | 40 | 5 | 4 | 2 | 5 |
| | 20 | 4 | 3 | 0 | 4 |
| | 10 | 1 | 2 | 0 | 3 |
| Non-treatment | — | 0 | 0 | 0 | 0 |

Test D

Phytotoxicity test for rice seedlings

Each Wagner pot of 1/5,000 was filled with paddy diluvium soil and manured (fertilizer application) and puddled with suitable water and two rice seedlings of 2.6 leaf stage (Sasanishiki, height of 14.3 cm: good seedling) were transplanted in a depth of about 2 cm, and the pot was flooded in a depth of 1.5 cm.

One or seven days after the transplantation, each granule containing each of Compounds of the present invention and Reference Compound was fallen on the flooded surface at each dose (40, 20 or 10 g/are) of the compound.

For three days after the treatment, a leaching loss of water was given at a rate of 3 cm/day and the pot was kept in greenhouse.

Twenty one days after the treatment, phytotoxicities of the compounds to rice seedlings were observed. The results are shown in Table 5.

The phytotoxicities were rated as follows.

$$\left(1 - \frac{\text{Weight of exposed rice seedling in treated pot}}{\text{Weight of exposed rice seedling in non-treated pot}}\right) \times 100 = Y(\%)$$

| Rating of phytotoxicity | Y(%) |
|---|---|
| 0 | 0–5 |
| 1 | 5–10 |
| 2 | 10–20 |
| 3 | 20–40 |
| 4 | 40–60 |
| 5 | 60–100 |

Test E

In accordance with the experiment of Test D, each test was carried out by using the compounds shown in Table 1. The results are shown in Table 6.

Test F

In accordance with the experiment of Test D, each test was carried out by using the compounds shown in Table 1. The results are shown in Table 7.

TABLE 5

| Compound No. | Dose of active ingredient (g/a) | Phytotoxicity to rice seedling | |
|---|---|---|---|
| | | one day after transplantation | 7 days after transplantion |
| 1 | 40 | 1 | 0 |
| | 20 | 0 | 0 |
| | 10 | 0 | 0 |
| 2 | 40 | 0 | 0 |
| | 20 | 0 | 0 |
| | 10 | 0 | 0 |
| 3 | 40 | 0 | 0 |
| | 20 | 0 | 0 |
| | 10 | 0 | 0 |
| 4 | 40 | 2 | 0 |
| | 20 | 0 | 0 |
| | 10 | 0 | 0 |
| 5 | 40 | 2 | 1 |
| | 20 | 0 | 0 |
| | 10 | 0 | 0 |
| 6 | 40 | 0 | 0 |
| | 20 | 0 | 0 |
| | 10 | 0 | 0 |
| 7 | 40 | 1 | 0 |
| | 20 | 0 | 0 |
| | 10 | 0 | 0 |
| 8 | 40 | 0 | 0 |
| | 20 | 0 | 0 |
| | 10 | 0 | 0 |
| 9 | 40 | 0 | 0 |
| | 20 | 0 | 0 |
| | 10 | 0 | 0 |
| 10 | 40 | 0 | 0 |
| | 20 | 0 | 0 |
| | 10 | 0 | 0 |
| 11 | 40 | 1 | 0 |

TABLE 5-continued

| Compound No. | Dose of active ingredient (g/a) | Phytotoxicity to rice seedling one day after transplantation | 7 days after transplantion |
|---|---|---|---|
| | 20 | 0 | 0 |
| | 10 | 0 | 0 |
| 12 | 40 | 1 | 0 |
| | 20 | 0 | 0 |
| | 10 | 0 | 0 |
| 13 | 40 | 0 | 0 |
| | 20 | 0 | 0 |
| | 10 | 0 | 0 |
| 14 | 40 | 1 | 0 |
| | 20 | 0 | 0 |
| | 10 | 0 | 0 |
| 15 | 40 | 2 | 0 |
| | 20 | 0 | 0 |
| | 10 | 0 | 0 |
| 16 | 40 | 1 | 0 |
| | 20 | 0 | 0 |
| | 10 | 0 | 0 |
| 17 | 40 | 1 | 1 |
| | 20 | 0 | 0 |
| | 10 | 0 | 0 |
| 18 | 40 | 1 | 0 |
| | 20 | 0 | 0 |
| | 10 | 0 | 0 |
| 19 | 40 | 0 | 0 |
| | 20 | 0 | 0 |
| | 10 | 0 | 0 |
| 20 | 40 | 1 | 0 |
| | 20 | 0 | 0 |
| | 10 | 0 | 0 |
| 21 | 40 | 1 | 1 |
| | 20 | 0 | 0 |
| | 10 | 0 | 0 |
| 22 | 40 | 2 | 0 |
| | 20 | 0 | 0 |
| | 10 | 0 | 0 |
| 23 | 40 | 0 | 0 |
| | 20 | 0 | 0 |
| | 10 | 0 | 0 |
| 24 | 40 | 0 | 0 |
| | 20 | 0 | 0 |
| | 10 | 0 | 0 |
| 25 | 40 | 1 | 0 |
| | 20 | 0 | 0 |
| | 10 | 0 | 0 |
| 26 | 40 | 1 | 0 |
| | 20 | 0 | 0 |
| | 10 | 0 | 0 |
| 27 | 40 | 1 | 0 |
| | 20 | 0 | 0 |
| | 10 | 0 | 0 |
| 28 | 40 | 1 | 0 |
| | 20 | 0 | 0 |
| | 10 | 0 | 0 |
| 29 | 40 | 1 | 0 |
| | 20 | 0 | 0 |
| | 10 | 0 | 0 |
| 30 | 40 | 1 | 0 |
| | 20 | 0 | 0 |
| | 10 | 0 | 0 |
| 31 | 40 | 0 | 0 |
| | 20 | 0 | 0 |
| | 10 | 0 | 0 |
| 32 | 40 | 1 | 1 |
| | 20 | 0 | 0 |
| | 10 | 0 | 0 |
| 33 | 40 | 0 | 0 |
| | 20 | 0 | 0 |
| | 10 | 0 | 0 |
| 34 | 40 | 0 | 0 |
| | 20 | 0 | 0 |
| | 10 | 0 | 0 |
| 35 | 40 | 2 | 0 |
| | 20 | 0 | 0 |
| | 10 | 0 | 0 |
| 36 | 40 | 0 | 0 |
| | 20 | 0 | 0 |
| | 10 | 0 | 0 |
| 37 | 40 | 1 | 0 |
| | 20 | 0 | 0 |
| | 10 | 0 | 0 |
| 38 | 40 | 0 | 0 |
| | 20 | 0 | 0 |
| | 10 | 0 | 0 |
| 39 | 40 | 0 | 0 |
| | 20 | 0 | 0 |
| | 10 | 0 | 0 |
| 40 | 40 | 1 | 0 |
| | 20 | 0 | 0 |
| | 10 | 0 | 0 |
| 41 | 40 | 0 | 0 |
| | 20 | 0 | 0 |
| | 10 | 0 | 0 |
| 42 | 40 | 0 | 0 |
| | 20 | 0 | 0 |
| | 10 | 0 | 0 |
| 43 | 40 | 0 | 0 |
| | 20 | 0 | 0 |
| | 10 | 0 | 0 |
| 44 | 40 | 1 | 1 |
| | 20 | 0 | 0 |
| | 10 | 0 | 0 |
| 45 | 40 | 1 | 0 |
| | 20 | 0 | 0 |
| | 10 | 0 | 0 |
| 46 | 40 | 1 | 0 |
| | 20 | 0 | 0 |
| | 10 | 0 | 0 |
| 47 | 40 | 0 | 0 |
| | 20 | 0 | 0 |
| | 10 | 0 | 0 |
| 48 | 40 | 0 | 0 |
| | 20 | 0 | 0 |
| | 10 | 0 | 0 |
| 49 | 40 | 0 | 0 |
| | 20 | 0 | 0 |
| | 10 | 0 | 0 |
| 50 | 40 | 1 | 0 |
| | 20 | 0 | 0 |
| | 10 | 0 | 0 |
| 151 | 40 | 0 | 0 |
| | 20 | 0 | 0 |
| | 10 | 0 | 0 |
| 152 | 40 | 0 | 0 |
| | 20 | 0 | 0 |
| | 10 | 0 | 0 |
| 153 | 40 | 1 | 1 |
| | 20 | 0 | 0 |
| | 10 | 0 | 0 |
| 154 | 40 | 1 | 0 |
| | 20 | 0 | 0 |
| | 10 | 0 | 0 |
| 155 | 40 | 0 | 0 |
| | 20 | 0 | 0 |
| | 10 | 0 | 0 |
| 156 | 40 | 0 | 0 |
| | 20 | 0 | 0 |
| | 10 | 0 | 0 |
| 157 | 40 | 0 | 0 |
| | 20 | 0 | 0 |
| | 10 | 0 | 0 |
| 158 | 40 | 0 | 0 |
| | 20 | 0 | 0 |
| | 10 | 0 | 0 |
| 159 | 40 | 1 | 0 |
| | 20 | 0 | 0 |
| | 10 | 0 | 0 |
| 160 | 40 | 0 | 0 |
| | 20 | 0 | 0 |
| | 10 | 0 | 0 |
| 161 | 40 | 0 | 0 |
| | 20 | 0 | 0 |
| | 10 | 0 | 0 |
| 162 | 40 | 1 | 0 |
| | 20 | 0 | 0 |

TABLE 5-continued

| Compound No. | Dose of active ingredient (g/a) | Phytotoxicity to rice seedling one day after transplantation | 7 days after transplantion |
|---|---|---|---|
| 163 | 10 | 0 | 0 |
|  | 40 | 0 | 0 |
|  | 20 | 0 | 0 |
|  | 10 | 0 | 0 |
| 164 | 40 | 1 | 0 |
|  | 20 | 0 | 0 |
|  | 10 | 0 | 0 |
| 165 | 40 | 0 | 0 |
|  | 20 | 0 | 0 |
|  | 10 | 0 | 0 |
| 166 | 40 | 1 | 0 |
|  | 20 | 0 | 0 |
|  | 10 | 0 | 0 |
| 167 | 40 | 0 | 0 |
|  | 20 | 0 | 0 |
|  | 10 | 0 | 0 |
| 168 | 40 | 0 | 0 |
|  | 20 | 0 | 0 |
|  | 10 | 0 | 0 |
| 169 | 40 | 0 | 0 |
|  | 20 | 0 | 0 |
|  | 10 | 0 | 0 |
| 170 | 40 | 0 | 0 |
|  | 20 | 0 | 0 |
|  | 10 | 0 | 0 |
| 171 | 40 | 0 | 0 |
|  | 20 | 0 | 0 |
|  | 10 | 0 | 0 |
| 172 | 40 | 1 | 0 |
|  | 20 | 0 | 0 |
|  | 10 | 0 | 0 |
| 173 | 40 | 0 | 0 |
|  | 20 | 0 | 0 |
|  | 10 | 0 | 0 |
| 174 | 40 | 1 | 0 |
|  | 20 | 0 | 0 |
|  | 10 | 0 | 0 |
| 175 | 40 | 2 | 0 |
|  | 20 | 0 | 0 |
|  | 10 | 0 | 0 |
| 176 | 40 | 1 | 1 |
|  | 20 | 0 | 0 |
|  | 10 | 0 | 0 |
| 177 | 40 | 1 | 0 |
|  | 20 | 0 | 0 |
|  | 10 | 0 | 0 |
| 178 | 40 | 0 | 0 |
|  | 20 | 0 | 0 |
|  | 10 | 0 | 0 |
| 179 | 40 | 1 | 0 |
|  | 20 | 0 | 0 |
|  | 10 | 0 | 0 |
| 180 | 40 | 0 | 0 |
|  | 20 | 0 | 0 |
|  | 10 | 0 | 0 |
| 181 | 40 | 0 | 0 |
|  | 20 | 0 | 0 |
|  | 10 | 0 | 0 |
| 182 | 40 | 0 | 0 |
|  | 20 | 0 | 0 |
|  | 10 | 0 | 0 |
| 183 | 40 | 1 | 0 |
|  | 20 | 0 | 0 |
|  | 10 | 0 | 0 |
| 184 | 40 | 0 | 0 |
|  | 20 | 0 | 0 |
|  | 10 | 0 | 0 |
| 185 | 40 | 0 | 0 |
|  | 20 | 0 | 0 |
|  | 10 | 0 | 0 |
| 186 | 40 | 0 | 0 |
|  | 20 | 0 | 0 |
|  | 10 | 0 | 0 |
| 187 | 40 | 1 | 0 |
|  | 20 | 0 | 0 |
|  | 10 | 0 | 0 |
| 188 | 40 | 1 | 1 |
|  | 20 | 0 | 0 |
|  | 10 | 0 | 0 |
| 189 | 40 | 1 | 0 |
|  | 20 | 0 | 0 |
|  | 10 | 0 | 0 |
| 190 | 40 | 1 | 0 |
|  | 20 | 0 | 0 |
|  | 10 | 0 | 0 |
| 191 | 40 | 0 | 0 |
|  | 20 | 0 | 0 |
|  | 10 | 0 | 0 |
| 192 | 40 | 0 | 0 |
|  | 20 | 0 | 0 |
|  | 10 | 0 | 0 |
| 193 | 40 | 0 | 0 |
|  | 20 | 0 | 0 |
|  | 10 | 0 | 0 |
| 194 | 40 | 1 | 0 |
|  | 20 | 0 | 0 |
|  | 10 | 0 | 0 |
| 195 | 40 | 1 | 0 |
|  | 20 | 0 | 0 |
|  | 10 | 0 | 0 |
| 196 | 40 | 0 | 0 |
|  | 20 | 0 | 0 |
|  | 10 | 0 | 0 |
| 197 | 40 | 0 | 0 |
|  | 20 | 0 | 0 |
|  | 10 | 0 | 0 |
| 198 | 40 | 0 | 0 |
|  | 20 | 0 | 0 |
|  | 10 | 0 | 0 |
| 199 | 40 | 0 | 0 |
|  | 20 | 0 | 0 |
|  | 10 | 0 | 0 |
| 200 | 40 | 0 | 0 |
|  | 20 | 0 | 0 |
|  | 10 | 0 | 0 |
| 201 | 40 | 0 | 0 |
|  | 20 | 0 | 0 |
|  | 10 | 0 | 0 |
| 202 | 40 | 0 | 0 |
|  | 20 | 0 | 0 |
|  | 10 | 0 | 0 |
| 203 | 40 | 1 | 0 |
|  | 20 | 0 | 0 |
|  | 10 | 0 | 0 |
| 204 | 40 | 0 | 0 |
|  | 20 | 0 | 0 |
|  | 10 | 0 | 0 |
| 205 | 40 | 1 | 0 |
|  | 20 | 0 | 0 |
|  | 10 | 0 | 0 |
| 206 | 40 | 0 | 0 |
|  | 20 | 0 | 0 |
|  | 10 | 0 | 0 |
| 207 | 40 | 0 | 0 |
|  | 20 | 0 | 0 |
|  | 10 | 0 | 0 |
| 208 | 40 | 0 | 0 |
|  | 20 | 0 | 0 |
|  | 10 | 0 | 0 |
| 209 | 40 | 0 | 0 |
|  | 20 | 0 | 0 |
|  | 10 | 0 | 0 |
| 210 | 40 | 0 | 0 |
|  | 20 | 0 | 0 |
|  | 10 | 0 | 0 |
| 211 | 40 | 0 | 0 |
|  | 20 | 0 | 0 |
|  | 10 | 0 | 0 |
| 212 | 40 | 1 | 0 |
|  | 20 | 0 | 0 |
|  | 10 | 0 | 0 |
| 213 | 40 | 0 | 0 |
|  | 20 | 0 | 0 |
|  | 10 | 0 | 0 |

TABLE 5-continued

| Compound No. | Dose of active ingredient (g/a) | Phytotoxicity to rice seedling one day after transplantation | 7 days after transplantion |
|---|---|---|---|
| 214 | 40 | 0 | 0 |
| | 20 | 0 | 0 |
| | 10 | 0 | 0 |
| 215 | 40 | 0 | 0 |
| | 20 | 0 | 0 |
| | 10 | 0 | 0 |
| Reference A | 40 | 2 | 2 |
| | 20 | 1 | 0 |
| | 10 | 0 | 0 |
| Reference B | 40 | 2 | 1 |
| | 20 | 1 | 1 |
| | 10 | 0 | 0 |
| Reference C | 40 | 3 | 2 |
| | 20 | 2 | 0 |
| | 10 | 0 | 0 |
| Reference D | 40 | 4 | 2 |
| | 20 | 2 | 1 |
| | 10 | 0 | 0 |
| Non-Treatment | 40 | 0 | 0 |
| | 20 | | |
| | 10 | | |

TABLE 6

| Compound No. | Dose of active ingredeient (g/a) | Phytotoxicity to rice seedling one day after transplantation | 7 days after transplantation |
|---|---|---|---|
| 227 | 40 | 0 | 0 |
| | 20 | 0 | 0 |
| | 10 | 0 | 0 |
| 228 | 40 | 1 | 1 |
| | 20 | 0 | 0 |
| | 10 | 0 | 0 |
| 229 | 40 | 1 | 0 |
| | 20 | 0 | 0 |
| | 10 | 0 | 0 |
| 230 | 40 | 2 | 0 |
| | 20 | 0 | 0 |
| | 10 | 0 | 0 |
| 231 | 40 | 1 | 0 |
| | 20 | 0 | 0 |
| | 10 | 0 | 0 |
| 232 | 40 | 1 | 0 |
| | 20 | 0 | 0 |
| | 10 | 0 | 0 |
| 233 | 40 | 0 | 0 |
| | 20 | 0 | 0 |
| | 10 | 0 | 0 |
| 234 | 40 | 1 | 0 |
| | 20 | 0 | 0 |
| | 10 | 0 | 0 |
| 235 | 40 | 0 | 0 |
| | 20 | 0 | 0 |
| | 10 | 0 | 0 |
| 236 | 40 | 1 | 0 |
| | 20 | 0 | 0 |
| | 10 | 0 | 0 |
| 237 | 40 | 1 | 0 |
| | 20 | 0 | 0 |
| | 10 | 0 | 0 |
| 238 | 40 | 0 | 0 |
| | 20 | 0 | 0 |
| | 10 | 0 | 0 |
| Reference A | 40 | 2 | 2 |
| | 20 | 1 | 0 |
| | 10 | 0 | 0 |
| Reference B | 40 | 2 | 1 |
| | 20 | 0 | 0 |
| | 10 | 0 | 0 |
| Reference C | 20 | 3 | 2 |
| | 10 | 2 | 0 |
| | 5 | 0 | 0 |
| Reference D | 40 | 4 | 2 |
| | 20 | 2 | 0 |
| | 10 | 0 | 0 |

TABLE 6-continued

| Compound No. | Dose of active ingredeient (g/a) | Phytotoxicity to rice seedling one day after transplantation | 7 days after transplantation |
|---|---|---|---|
| Non-treatment | — | 0 | 0 |

TABLE 7

| Compound No. | Dose of active ingredient (g/a) | Phytotoxicity to rice seedling one day after transplantation | 7 days after transplantation |
|---|---|---|---|
| 239 | 40 | 1 | 0 |
| | 20 | 0 | 0 |
| | 10 | 0 | 0 |
| 240 | 40 | 1 | 1 |
| | 20 | 0 | 0 |
| | 10 | 0 | 0 |
| 241 | 40 | 2 | 1 |
| | 20 | 0 | 0 |
| | 10 | 0 | 0 |
| 242 | 40 | 1 | 0 |
| | 20 | 0 | 0 |
| | 10 | 0 | 0 |
| 243 | 40 | 0 | 0 |
| | 20 | 0 | 0 |
| | 10 | 0 | 0 |
| 244 | 40 | 1 | 0 |
| | 20 | 0 | 0 |
| | 10 | 0 | 0 |
| 245 | 40 | 0 | 0 |
| | 20 | 0 | 0 |
| | 10 | 0 | 0 |
| 246 | 40 | 0 | 0 |
| | 20 | 0 | 0 |
| | 10 | 0 | 0 |
| 247 | 40 | 1 | 0 |
| | 20 | 0 | 0 |
| | 10 | 0 | 0 |
| 248 | 40 | 0 | 0 |
| | 20 | 0 | 0 |
| | 10 | 0 | 0 |
| 249 | 40 | 0 | 0 |
| | 20 | 0 | 0 |
| | 10 | 0 | 0 |
| 250 | 40 | 0 | 0 |
| | 20 | 0 | 0 |
| | 10 | 0 | 0 |
| 251 | 40 | 1 | 0 |
| | 20 | 0 | 0 |
| | 10 | 0 | 0 |
| 252 | 40 | 0 | 0 |
| | 20 | 0 | 0 |
| | 10 | 0 | 0 |
| 253 | 40 | 1 | 0 |
| | 20 | 0 | 0 |
| | 10 | 0 | 0 |
| 254 | 40 | 0 | 0 |
| | 20 | 0 | 0 |
| | 10 | 0 | 0 |
| 255 | 40 | 0 | 0 |
| | 20 | 0 | 0 |
| | 10 | 0 | 0 |
| 256 | 40 | 0 | 0 |
| | 20 | 0 | 0 |
| | 10 | 0 | 0 |
| 257 | 40 | 0 | 0 |
| | 20 | 0 | 0 |
| | 10 | 0 | 0 |
| 258 | 40 | 1 | 0 |
| | 20 | 0 | 0 |
| | 10 | 0 | 0 |
| 259 | 40 | 1 | 1 |
| | 20 | 0 | 0 |
| | 10 | 0 | 0 |
| 260 | 40 | 0 | 0 |
| | 20 | 0 | 0 |
| | 10 | 0 | 0 |
| 261 | 40 | 0 | 0 |
| | 20 | 0 | 0 |

TABLE 7-continued

| Compound No. | Dose of active ingredient (g/a) | Phytotoxicity to rice seedling one day after transplantation | 7 days after transplantation |
|---|---|---|---|
| 262 | 10 | 0 | 0 |
|  | 40 | 2 | 0 |
|  | 20 | 0 | 0 |
| 263 | 10 | 0 | 0 |
|  | 40 | 1 | 0 |
|  | 20 | 0 | 0 |
| 264 | 10 | 0 | 0 |
|  | 40 | 0 | 0 |
|  | 20 | 0 | 0 |
| 265 | 10 | 0 | 0 |
|  | 40 | 1 | 0 |
|  | 20 | 0 | 0 |
| 266 | 10 | 0 | 0 |
|  | 40 | 1 | 0 |
|  | 20 | 0 | 0 |
| 267 | 10 | 0 | 0 |
|  | 40 | 1 | 0 |
|  | 20 | 0 | 0 |
| 268 | 10 | 0 | 0 |
|  | 40 | 0 | 0 |
|  | 20 | 0 | 0 |
| 267 | 10 | 0 | 0 |
|  | 40 | 1 | 0 |
|  | 20 | 0 | 0 |
| 270 | 10 | 0 | 0 |
|  | 40 | 1 | 0 |
|  | 20 | 0 | 0 |
| 271 | 10 | 0 | 0 |
|  | 40 | 0 | 0 |
|  | 20 | 0 | 0 |
| 272 | 10 | 0 | 0 |
|  | 40 | 1 | 0 |
|  | 20 | 0 | 0 |
| 273 | 10 | 0 | 0 |
|  | 40 | 2 | 1 |
|  | 20 | 0 | 0 |
| 274 | 10 | 0 | 0 |
|  | 40 | 1 | 0 |
|  | 20 | 0 | 0 |
| 275 | 10 | 0 | 0 |
|  | 40 | 0 | 0 |
|  | 20 | 0 | 0 |
| 276 | 10 | 0 | 0 |
|  | 40 | 0 | 0 |
|  | 20 | 0 | 0 |
| 277 | 10 | 0 | 0 |
|  | 40 | 0 | 0 |
|  | 20 | 0 | 0 |
| 278 | 10 | 0 | 0 |
|  | 40 | 1 | 0 |
|  | 20 | 0 | 0 |
| 279 | 10 | 0 | 0 |
|  | 40 | 1 | 1 |
|  | 20 | 0 | 0 |
| 280 | 10 | 0 | 0 |
|  | 40 | 0 | 0 |
|  | 20 | 0 | 0 |
| 281 | 10 | 0 | 0 |
|  | 40 | 0 | 0 |
|  | 20 | 0 | 0 |
| 282 | 10 | 0 | 0 |
|  | 40 | 0 | 0 |
|  | 20 | 0 | 0 |
| 283 | 10 | 0 | 0 |
|  | 40 | 0 | 0 |
|  | 20 | 0 | 0 |
| 284 | 10 | 0 | 0 |
|  | 40 | 0 | 0 |
|  | 20 | 0 | 0 |
| 285 | 10 | 0 | 0 |
|  | 40 | 1 | 0 |
|  | 20 | 0 | 0 |
| 286 | 10 | 0 | 0 |
|  | 40 | 0 | 0 |
|  | 20 | 0 | 0 |
| 287 | 10 | 0 | 0 |
|  | 40 | 0 | 0 |
|  | 20 | 0 | 0 |
| 288 | 10 | 0 | 0 |
|  | 40 | 1 | 1 |
|  | 20 | 0 | 0 |
| 313 | 10 | 0 | 0 |
|  | 40 | 0 | 0 |
|  | 20 | 0 | 0 |
| 314 | 10 | 0 | 0 |
|  | 40 | 1 | 0 |
|  | 20 | 0 | 0 |
| 315 | 10 | 0 | 0 |
|  | 40 | 0 | 0 |
|  | 20 | 0 | 0 |
| 316 | 10 | 0 | 0 |
|  | 40 | 0 | 0 |
|  | 20 | 0 | 0 |
| 317 | 10 | 0 | 0 |
|  | 40 | 1 | 0 |
|  | 20 | 0 | 0 |
| 318 | 10 | 0 | 0 |
|  | 40 | 0 | 0 |
|  | 20 | 0 | 0 |
| 319 | 10 | 0 | 0 |
|  | 40 | 0 | 0 |
|  | 20 | 0 | 0 |
| 320 | 10 | 0 | 0 |
|  | 40 | 1 | 0 |
|  | 20 | 0 | 0 |
| 321 | 10 | 0 | 0 |
|  | 40 | 0 | 0 |
|  | 20 | 0 | 0 |
| 322 | 10 | 0 | 0 |
|  | 40 | 0 | 0 |
|  | 20 | 0 | 0 |
| 323 | 10 | 0 | 0 |
|  | 40 | 1 | 1 |
|  | 20 | 0 | 0 |
| 324 | 10 | 0 | 0 |
|  | 40 | 0 | 0 |
|  | 20 | 0 | 0 |
| 325 | 10 | 0 | 0 |
|  | 40 | 0 | 0 |
|  | 20 | 0 | 0 |
| 326 | 10 | 0 | 0 |
|  | 40 | 1 | 0 |
|  | 20 | 0 | 0 |
| 327 | 10 | 0 | 0 |
|  | 40 | 1 | 1 |
|  | 20 | 0 | 0 |
| 328 | 10 | 0 | 0 |
|  | 40 | 0 | 0 |
|  | 20 | 0 | 0 |
| 329 | 10 | 0 | 0 |
|  | 40 | 0 | 0 |
|  | 20 | 0 | 0 |
| 330 | 10 | 0 | 0 |
|  | 40 | 0 | 0 |
|  | 20 | 0 | 0 |
| 331 | 10 | 0 | 0 |
|  | 40 | 1 | 0 |
|  | 20 | 0 | 0 |
| 332 | 10 | 0 | 0 |
|  | 40 | 0 | 0 |
|  | 20 | 0 | 0 |
| 333 | 10 | 0 | 0 |
|  | 40 | 0 | 0 |
|  | 20 | 0 | 0 |
| 334 | 10 | 0 | 0 |
|  | 40 | 1 | 0 |
|  | 20 | 0 | 0 |
| 335 | 10 | 0 | 0 |
|  | 40 | 0 | 0 |
|  | 20 | 0 | 0 |
| 336 | 10 | 0 | 0 |
|  | 40 | 0 | 0 |
|  | 20 | 0 | 0 |

TABLE 7-continued

| Compound No. | Dose of active ingredient (g/a) | Phytotoxicity to rice seedling one day after transplantation | 7 days after transplantation |
|---|---|---|---|
| 337 | 40 | 0 | 0 |
|  | 20 | 0 | 0 |
|  | 10 | 0 | 0 |
| 338 | 40 | 1 | 0 |
|  | 20 | 0 | 0 |
|  | 10 | 0 | 0 |
| 339 | 40 | 0 | 0 |
|  | 20 | 0 | 0 |
|  | 10 | 0 | 0 |
| 340 | 40 | 0 | 0 |
|  | 20 | 0 | 0 |
|  | 10 | 0 | 0 |
| 341 | 40 | 1 | 0 |
|  | 20 | 1 | 0 |
|  | 10 | 0 | 0 |
| 342 | 40 | 1 | 0 |
|  | 20 | 0 | 0 |
|  | 10 | 0 | 0 |
| 343 | 40 | 1 | 1 |
|  | 20 | 0 | 0 |
|  | 10 | 0 | 0 |
| 344 | 40 | 2 | 0 |
|  | 20 | 0 | 0 |
|  | 10 | 0 | 0 |
| 345 | 40 | 1 | 1 |
|  | 20 | 0 | 0 |
|  | 10 | 0 | 0 |
| 346 | 40 | 2 | 1 |
|  | 20 | 0 | 0 |
|  | 10 | 0 | 0 |
| 347 | 40 | 1 | 1 |
|  | 20 | 1 | 0 |
|  | 10 | 0 | 0 |
| 348 | 40 | 1 | 1 |
|  | 20 | 0 | 0 |
|  | 10 | 0 | 0 |
| 349 | 40 | 1 | 0 |
|  | 20 | 0 | 0 |
|  | 10 | 0 | 0 |
| 350 | 40 | 1 | 0 |
|  | 20 | 0 | 0 |
|  | 10 | 0 | 0 |
| 351 | 40 | 0 | 0 |
|  | 20 | 0 | 0 |
|  | 10 | 0 | 0 |
| 352 | 40 | 0 | 0 |
|  | 20 | 0 | 0 |
|  | 10 | 0 | 0 |
| 353 | 40 | 1 | 0 |
|  | 20 | 0 | 0 |
|  | 10 | 0 | 0 |
| 354 | 40 | 1 | 0 |
|  | 20 | 1 | 0 |
|  | 10 | 0 | 0 |
| 355 | 40 | 1 | 0 |
|  | 20 | 0 | 0 |
|  | 10 | 0 | 0 |
| 356 | 40 | 0 | 0 |
|  | 20 | 0 | 0 |
|  | 10 | 0 | 0 |
| 357 | 40 | 1 | 0 |
|  | 20 | 0 | 0 |
|  | 10 | 0 | 0 |
| 358 | 40 | 1 | 1 |
|  | 20 | 0 | 0 |
|  | 10 | 0 | 0 |
| 359 | 40 | 1 | 0 |
|  | 20 | 0 | 0 |
|  | 10 | 0 | 0 |
| 360 | 40 | 2 | 0 |
|  | 20 | 0 | 0 |
|  | 10 | 0 | 0 |
| 361 | 40 | 1 | 0 |
|  | 20 | 0 | 0 |
|  | 10 | 0 | 0 |
| 362 | 40 | 1 | 0 |
|  | 20 | 0 | 0 |
|  | 10 | 0 | 0 |
| 363 | 40 | 1 | 0 |
|  | 20 | 0 | 0 |
|  | 10 | 0 | 0 |
| 364 | 40 | 1 | 0 |
|  | 20 | 0 | 0 |
|  | 10 | 0 | 0 |
| 365 | 40 | 2 | 1 |
|  | 20 | 0 | 0 |
|  | 10 | 0 | 0 |
| 366 | 40 | 1 | 1 |
|  | 20 | 0 | 0 |
|  | 10 | 0 | 0 |
| 367 | 40 | 0 | 0 |
|  | 20 | 0 | 0 |
|  | 10 | 0 | 0 |
| 368 | 40 | 1 | 0 |
|  | 20 | 0 | 0 |
|  | 10 | 0 | 0 |
| 369 | 40 | 1 | 1 |
|  | 20 | 0 | 0 |
|  | 10 | 0 | 0 |
| 370 | 40 | 1 | 0 |
|  | 20 | 0 | 0 |
|  | 10 | 0 | 0 |
| 371 | 40 | 0 | 0 |
|  | 20 | 0 | 0 |
|  | 10 | 0 | 0 |
| 372 | 40 | 0 | 0 |
|  | 20 | 0 | 0 |
|  | 10 | 0 | 0 |
| 373 | 40 | 1 | 0 |
|  | 20 | 0 | 0 |
|  | 10 | 0 | 0 |
| 374 | 40 | 0 | 0 |
|  | 20 | 0 | 0 |
|  | 10 | 0 | 0 |
| 375 | 40 | 1 | 0 |
|  | 20 | 0 | 0 |
|  | 10 | 0 | 0 |
| 376 | 40 | 1 | 0 |
|  | 20 | 0 | 0 |
|  | 10 | 0 | 0 |
| 377 | 40 | 2 | 1 |
|  | 20 | 0 | 0 |
|  | 10 | 0 | 0 |
| Reference A | 40 | 2 | 1 |
|  | 20 | 1 | 1 |
|  | 10 | 0 | 0 |
| Reference B | 40 | 1 | 1 |
|  | 20 | 1 | 0 |
|  | 10 | 0 | 0 |
| Reference C | 40 | 3 | 2 |
|  | 20 | 2 | 1 |
|  | 10 | 0 | 0 |
| Reference D | 40 | 4 | 2 |
|  | 20 | 2 | 1 |
|  | 10 | 0 | 0 |
| Non-treatment | — | 0 | 0 |

Test G

Up-land soil treatment test

Each plastic pot of 1/2,500 are was filled with black volcano ash soil and manured and seeds of wheat, corn, soybean, and cotton were sown and were covered with the soil in a depth of 2 to 3 cm and seeds of weeds of Large crabgrass, Ladys thumb and Lambsquarter were mixed in the covered soil layer. Each wettable powder containing each of Compounds of the present invention and Reference Compound was diluted with water and the solution was sprayed uniformly on the surface of the soil at a dose (40, 20 or 10 g/are) of the compound by a small size power pressurized spray.

Twenty days after the treatment, herbicidal effects were observed and phytotoxicities to the crop plants were also observed. The results are shown in Table 8.

The herbicidal effects are rated as those of Test A and the phytotoxicities to crop plants are rated as those of Test C.

Test H

In accordance with the experiment of Test G, each test was carried out by using the compounds shown in Table 1. The results are shown in Table 9.

Test I

In accordance with the experiment of Test G, each test was carried out by using the compounds shown in Table 1. The results are shown in Table 10.

TABLE 8

| Comp. No. | Dose of Comp. (g/a) | Herbicidal effect | | | Phytotoxicity to crop plants | | | |
|---|---|---|---|---|---|---|---|---|
| | | C.G. | L.T. | L.A. | Wheat | Corn | Soybean | Cotton |
| 25 | 40 | 5 | 5 | 5 | 0 | 0 | 0 | 0 |
| | 20 | 5 | 4 | 5 | 0 | 0 | 0 | 0 |
| | 10 | 4 | 4 | 5 | 0 | 0 | 0 | 0 |
| 26 | 40 | 5 | 5 | 5 | 0 | 0 | 0 | 0 |
| | 20 | 5 | 5 | 5 | 0 | 0 | 0 | 0 |
| | 10 | 3 | 3 | 4 | 0 | 0 | 0 | 0 |
| 27 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 28 | 40 | 5 | 5 | 5 | 0 | 0 | 0 | 0 |
| | 20 | 4 | 4 | 5 | 0 | 0 | 0 | 0 |
| | 10 | 3 | 4 | 4 | 0 | 0 | 0 | 0 |
| 29 | 40 | 5 | 5 | 5 | 0 | 0 | 0 | 0 |
| | 20 | 4 | 4 | 5 | 0 | 0 | 0 | 0 |
| | 10 | 3 | 4 | 4 | 0 | 0 | 0 | 0 |
| 30 | 40 | 5 | 5 | 5 | 1 | 0 | 0 | 0 |
| | 20 | 5 | 5 | 5 | 0 | 0 | 0 | 0 |
| | 10 | 5 | 4 | 5 | 0 | 0 | 0 | 0 |
| 31 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 32 | 40 | 5 | 5 | 5 | 0 | 0 | 0 | 0 |
| | 20 | 5 | 5 | 5 | 0 | 0 | 0 | 0 |
| | 10 | 3 | 4 | 5 | 0 | 0 | 0 | 0 |
| 33 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 34 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 35 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 36 | 40 | 4 | 4 | 5 | 0 | 0 | 0 | 0 |
| | 20 | 4 | 4 | 5 | 0 | 0 | 0 | 0 |
| | 10 | 4 | 4 | 4 | 0 | 0 | 0 | 0 |
| 37 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 38 | 40 | 5 | 5 | 5 | 0 | 0 | 0 | 0 |
| | 20 | 5 | 5 | 5 | 0 | 0 | 0 | 0 |
| | 10 | 3 | 5 | 5 | 0 | 0 | 0 | 0 |
| 39 | 40 | 5 | 5 | 5 | 0 | 0 | 0 | 0 |
| | 20 | 5 | 5 | 5 | 0 | 0 | 0 | 0 |
| | 10 | 3 | 4 | 5 | 0 | 0 | 0 | 0 |
| 40 | 40 | 4 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 41 | 40 | 5 | 5 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |
| 42 | 40 | 4 | 5 | 5 | 0 | 0 | 0 | 0 |
| | 20 | 4 | 5 | 5 | 0 | 0 | 0 | 0 |
| | 10 | 3 | 3 | 5 | 0 | 0 | 0 | 0 |
| 43 | 40 | 5 | 5 | 5 | 0 | 0 | 0 | 0 |
| | 20 | 4 | 5 | 5 | 0 | 0 | 0 | 0 |
| | 10 | 3 | 3 | 5 | 0 | 0 | 0 | 0 |
| 44 | 40 | 4 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 45 | 40 | 5 | 4 | 5 | 0 | 0 | 0 | 0 |
| | 20 | 4 | 4 | 5 | 0 | 0 | 0 | 0 |
| | 10 | 4 | 4 | 5 | 0 | 0 | 0 | 0 |
| 46 | 40 | 5 | 5 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |
| 47 | 40 | 5 | 5 | 5 | 0 | 0 | 0 | 0 |
| | 20 | 4 | 5 | 5 | 0 | 0 | 0 | 0 |
| | 10 | 3 | 3 | 4 | 0 | 0 | 0 | 0 |
| 48 | 40 | 5 | 5 | 5 | 1 | 0 | 0 | 1 |
| | 20 | 5 | 5 | 5 | 0 | 0 | 0 | 0 |
| | 10 | 5 | 5 | 5 | 0 | 0 | 0 | 0 |
| 49 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 50 | 40 | 5 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 51 | 40 | 5 | 5 | 5 | 0 | 0 | 0 | 0 |
| | 20 | 4 | 4 | 5 | 0 | 0 | 0 | 0 |
| | 10 | 3 | 3 | 4 | 0 | 0 | 0 | 0 |
| 52 | 40 | 4 | 5 | 5 | 0 | 0 | 0 | 0 |
| | 20 | 4 | 5 | 5 | 0 | 0 | 0 | 0 |
| | 10 | 3 | 3 | 5 | 0 | 0 | 0 | 0 |
| 53 | 40 | 5 | 5 | 5 | 1 | 0 | 0 | 0 |
| | 20 | 5 | 5 | 5 | 0 | 0 | 0 | 0 |
| | 10 | 5 | 5 | 5 | 0 | 0 | 0 | 0 |
| 54 | 40 | 5 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 55 | 40 | 5 | 4 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |
| 56 | 40 | 5 | 5 | 5 | 0 | 0 | 0 | 0 |
| | 20 | 4 | 4 | 5 | 0 | 0 | 0 | 0 |
| | 10 | 3 | 3 | 5 | 0 | 0 | 0 | 0 |
| 57 | 40 | 5 | 5 | 5 | 0 | 0 | 0 | 0 |
| | 20 | 4 | 4 | 5 | 0 | 0 | 0 | 0 |
| | 10 | 4 | 4 | 5 | 0 | 0 | 0 | 0 |
| 58 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 59 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 60 | 40 | 5 | 5 | 5 | 0 | 0 | 0 | 0 |
| | 20 | 4 | 4 | 5 | 0 | 0 | 0 | 0 |
| | 10 | 4 | 5 | 5 | 0 | 0 | 0 | 0 |
| 61 | 40 | 4 | 4 | 5 | 0 | 0 | 0 | 0 |
| | 20 | 4 | 4 | 5 | 0 | 0 | 0 | 0 |
| | 10 | 4 | 3 | 5 | 0 | 0 | 0 | 0 |
| 62 | 40 | 5 | 5 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |
| 63 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 64 | 40 | 5 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 65 | 40 | 5 | 5 | 5 | 0 | 0 | 0 | 0 |
| | 20 | 4 | 4 | 5 | 0 | 0 | 0 | 0 |
| | 10 | 3 | 3 | 4 | 0 | 0 | 0 | 0 |
| 66 | 40 | 5 | 5 | 5 | 1 | 0 | 0 | 0 |
| | 20 | 5 | 5 | 5 | 0 | 0 | 0 | 0 |
| | 10 | 4 | 5 | 5 | 0 | 0 | 0 | 0 |
| 67 | 40 | 4 | 5 | 5 | 0 | 0 | 0 | 0 |
| | 20 | 4 | 4 | 5 | 0 | 0 | 0 | 0 |
| | 10 | 4 | 3 | 5 | 0 | 0 | 0 | 0 |
| 68 | 40 | 5 | 5 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |

TABLE 8-continued

| Comp. No. | Dose of Comp. (g/a) | Herbicidal effect | | | Phytotoxicity to crop plants | | | |
|---|---|---|---|---|---|---|---|---|
| | | C.G. | L.T. | L.A. | Wheat | Corn | Soybean | Cotton |
| 69 | 40 | 5 | 5 | 5 | 0 | 0 | 0 | 0 |
| | 20 | 3 | 5 | 5 | 0 | 0 | 0 | 0 |
| | 10 | 3 | 4 | 5 | 0 | 0 | 0 | 0 |
| 70 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 71 | 40 | 5 | 5 | 5 | 0 | 0 | 0 | 0 |
| | 20 | 5 | 5 | 5 | 0 | 0 | 0 | 0 |
| | 10 | 3 | 4 | 5 | 0 | 0 | 0 | 0 |
| 72 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 73 | 40 | 5 | 5 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |
| 74 | 40 | 4 | 5 | 5 | 0 | 0 | 0 | 0 |
| | 20 | 4 | 5 | 5 | 0 | 0 | 0 | 0 |
| | 10 | 4 | 3 | 5 | 0 | 0 | 0 | 0 |
| 75 | 40 | 5 | 5 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |
| 76 | 40 | 5 | 5 | 5 | 1 | 0 | 0 | 0 |
| | 20 | 5 | 5 | 5 | 0 | 0 | 0 | 0 |
| | 10 | 3 | 4 | 5 | 0 | 0 | 0 | 0 |
| 105 | 40 | 4 | 5 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |
| 106 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 107 | 40 | 5 | 5 | 5 | 1 | 0 | 0 | 1 |
| | 20 | 5 | 5 | 5 | 0 | 0 | 0 | 0 |
| | 10 | 4 | 5 | 5 | 0 | 0 | 0 | 0 |
| 108 | 40 | 5 | 5 | 5 | 0 | 0 | 0 | 0 |
| | 20 | 5 | 5 | 5 | 0 | 0 | 0 | 0 |
| | 10 | 3 | 4 | 5 | 0 | 0 | 0 | 0 |
| 109 | 40 | 4 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 110 | 40 | 5 | 5 | 5 | 0 | 0 | 0 | 0 |
| | 20 | 5 | 5 | 5 | 0 | 0 | 0 | 0 |
| | 10 | 3 | 4 | 5 | 0 | 0 | 0 | 0 |
| 111 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 112 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 113 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 114 | 40 | 4 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 115 | 40 | 5 | 5 | 5 | 0 | 0 | 0 | 0 |
| | 20 | 4 | 5 | 5 | 0 | 0 | 0 | 0 |
| | 10 | 3 | 3 | 5 | 0 | 0 | 0 | 0 |
| 116 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 117 | 40 | 4 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 118 | 40 | 4 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 119 | 40 | 5 | 5 | 5 | 0 | 0 | 0 | 0 |
| | 20 | 4 | 4 | 5 | 0 | 0 | 0 | 0 |
| | 10 | 4 | 4 | 5 | 0 | 0 | 0 | 0 |
| 120 | 40 | 4 | 5 | 5 | 0 | 0 | 0 | 0 |
| | 20 | 4 | 5 | 5 | 0 | 0 | 0 | 0 |
| | 10 | 3 | 3 | 5 | 0 | 0 | 0 | 0 |
| 121 | 40 | 5 | 5 | 5 | 0 | 0 | 0 | 0 |
| | 20 | 4 | 4 | 5 | 0 | 0 | 0 | 0 |
| | 10 | 3 | 4 | 4 | 0 | 0 | 0 | 0 |
| 122 | 40 | 4 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 123 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 124 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 125 | 40 | 5 | 5 | 5 | 0 | 0 | 0 | 0 |
| | 20 | 5 | 5 | 5 | 0 | 0 | 0 | 0 |
| | 10 | 3 | 4 | 5 | 0 | 0 | 0 | 0 |
| Ref. A | 40 | 5 | 5 | 5 | 2 | 0 | 0 | 1 |
| | 20 | 4 | 4 | 5 | 0 | 0 | 0 | 0 |
| | 10 | 3 | 4 | 4 | 0 | 0 | 0 | 0 |
| Ref. B | 40 | 5 | 5 | 5 | 2 | 0 | 0 | 0 |
| | 20 | 4 | 4 | 5 | 0 | 0 | 0 | 0 |
| | 10 | 2 | 4 | 4 | 0 | 0 | 0 | 0 |
| Ref. E | 40 | 5 | 5 | 5 | 4 | 3 | 1 | 2 |
| | 20 | 5 | 5 | 5 | 2 | 1 | 0 | 2 |
| | 10 | 3 | 3 | 4 | 0 | 0 | 0 | 0 |
| Ref. F | 40 | 5 | 5 | 5 | 3 | 2 | 1 | 2 |
| | 20 | 4 | 4 | 4 | 1 | 0 | 0 | 0 |
| | 10 | 2 | 2 | 3 | 0 | 0 | 0 | 0 |
| Non-treatment | | 0 | 0 | 0 | 0 | 0 | 0 | 0 |

TABLE 9

| Comp. No. | Dose of Comp. (g/a) | Herbicidal effect | | | Phytotoxicity to crop plants | | | |
|---|---|---|---|---|---|---|---|---|
| | | C.G. | L.T. | L.A. | Wheat | Corn | Soybean | Cotton |
| 228 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 229 | 40 | 5 | 5 | 5 | 2 | 0 | 0 | 0 |
| | 20 | 5 | 5 | 5 | 0 | 0 | 0 | 0 |
| | 10 | 5 | 5 | 5 | 0 | 0 | 0 | 0 |
| 230 | 40 | 5 | 5 | 5 | 1 | 0 | 0 | 0 |
| | 20 | 5 | 5 | 5 | 0 | 0 | 0 | 0 |
| | 10 | 5 | 5 | 5 | 0 | 0 | 0 | 0 |
| 231 | 40 | 5 | 5 | 5 | 1 | 0 | 0 | 0 |
| | 20 | 5 | 5 | 5 | 0 | 0 | 0 | 0 |
| | 10 | 5 | 5 | 5 | 0 | 0 | 0 | 0 |
| 232 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 233 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 234 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 235 | 40 | 5 | 5 | 5 | 1 | 0 | 0 | 0 |
| | 20 | 5 | 5 | 5 | 0 | 0 | 0 | 0 |
| | 10 | 4 | 5 | 5 | 0 | 0 | 0 | 0 |
| 236 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| Ref. A | 40 | 5 | 5 | 5 | 2 | 0 | 0 | 0 |
| | 20 | 4 | 4 | 5 | 0 | 0 | 0 | 0 |
| | 10 | 3 | 3 | 4 | 0 | 0 | 0 | 0 |
| Ref. B | 40 | 5 | 5 | 5 | 1 | 0 | 0 | 1 |
| | 20 | 4 | 4 | 4 | 0 | 0 | 0 | 0 |
| | 10 | 3 | 4 | 4 | 0 | 0 | 0 | 0 |
| Ref. E | 40 | 5 | 5 | 5 | 4 | 2 | 1 | 2 |
| | 20 | 5 | 5 | 5 | 2 | 1 | 0 | 1 |
| | 10 | 3 | 4 | 4 | 0 | 0 | 0 | 0 |
| Ref. F | 40 | 5 | 5 | 5 | 3 | 1 | 2 | 1 |
| | 20 | 4 | 4 | 4 | 1 | 0 | 0 | 0 |
| | 10 | 2 | 3 | 3 | 0 | 0 | 0 | 0 |
| Non-treatment | — | 0 | 0 | 0 | 0 | 0 | 0 | 0 |

TABLE 10

| Comp. No. | Dose of Comp. (g/a) | Herbicidal effect C.G. | L.T. | L.A. | Phytotoxicity to crop plants Wheat | Corn | Soybean | Cotton |
|---|---|---|---|---|---|---|---|---|
| 258 | 40 | 5 | 5 | 5 | 0 | 0 | 0 | 0 |
|  | 20 | 5 | 5 | 5 | 0 | 0 | 0 | 0 |
|  | 10 | 4 | 4 | 5 | 0 | 0 | 0 | 0 |
| 259 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 260 | 40 | 5 | 5 | 5 | 0 | 0 | 0 | 0 |
|  | 20 | 4 | 4 | 5 | 0 | 0 | 0 | 0 |
|  | 10 | 3 | 4 | 5 | 0 | 0 | 0 | 0 |
| 261 | 40 | 5 | 5 | 5 | 0 | 0 | 0 | 0 |
|  | 20 | 4 | 4 | 5 | 0 | 0 | 0 | 0 |
|  | 10 | 3 | 3 | 5 | 0 | 0 | 0 | 0 |
| 262 | 40 | 5 | 5 | 5 | 0 | 0 | 0 | 0 |
|  | 20 | 4 | 5 | 5 | 0 | 0 | 0 | 0 |
|  | 10 | 4 | 4 | 5 | 0 | 0 | 0 | 0 |
| 263 | 40 | 5 | 5 | 5 | 0 | 0 | 0 | 0 |
|  | 20 | 5 | 5 | 5 | 0 | 0 | 0 | 0 |
|  | 10 | 5 | 4 | 5 | 0 | 0 | 0 | 0 |
| 264 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 265 | 40 | 5 | 5 | 5 | 1 | 0 | 0 | 0 |
|  | 20 | 5 | 5 | 5 | 0 | 0 | 0 | 0 |
|  | 10 | 5 | 5 | 5 | 0 | 0 | 0 | 0 |
| 266 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 267 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 268 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 269 | 40 | 5 | 5 | 5 | 0 | 0 | 0 | 1 |
|  | 20 | 5 | 5 | 5 | 0 | 0 | 0 | 0 |
|  | 10 | 5 | 5 | 5 | 0 | 0 | 0 | 0 |
| 270 | 40 | 5 | 5 | 5 | 1 | 0 | 0 | 0 |
|  | 20 | 5 | 5 | 5 | 0 | 0 | 0 | 0 |
|  | 10 | 5 | 5 | 5 | 0 | 0 | 0 | 0 |
| 271 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 272 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 273 | 40 | 5 | 5 | 5 | 1 | 0 | 0 | 1 |
|  | 20 | 5 | 5 | 5 | 0 | 0 | 0 | 0 |
|  | 10 | 5 | 5 | 5 | 0 | 0 | 0 | 0 |
| 274 | 40 | 5 | 5 | 5 | 1 | 0 | 0 | 0 |
|  | 20 | 5 | 5 | 5 | 0 | 0 | 0 | 0 |
|  | 10 | 5 | 5 | 5 | 0 | 0 | 0 | 0 |
| 275 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 276 | 40 | 5 | 5 | 5 | 0 | 0 | 0 | 0 |
|  | 20 | 4 | 5 | 5 | 0 | 0 | 0 | 0 |
|  | 10 | 4 | 4 | 5 | 0 | 0 | 0 | 0 |
| 277 | 40 | 4 | 5 | 5 | 0 | 0 | 0 | 0 |
|  | 20 | 4 | 5 | 5 | 0 | 0 | 0 | 0 |
|  | 10 | 3 | 5 | 5 | 0 | 0 | 0 | 0 |
| 278 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 279 | 40 | 5 | 5 | 5 | 1 | 0 | 0 | 0 |
|  | 20 | 5 | 5 | 5 | 0 | 0 | 0 | 0 |
|  | 10 | 5 | 5 | 5 | 0 | 0 | 0 | 0 |
| 280 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 281 | 40 | 5 | 5 | 5 | 2 | 0 | 0 | 0 |
|  | 20 | 5 | 5 | 5 | 0 | 0 | 0 | 0 |
|  | 10 | 5 | 5 | 5 | 0 | 0 | 0 | 0 |
| 282 | 40 | 5 | 5 | 5 | 0 | 0 | 0 | 1 |
|  | 20 | 5 | 5 | 5 | 0 | 0 | 0 | 0 |
|  | 10 | 5 | 5 | 5 | 0 | 0 | 0 | 0 |
| 283 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 284 | 40 | 5 | 5 | 5 | 0 | 0 | 0 | 0 |
|  | 20 | 4 | 5 | 5 | 0 | 0 | 0 | 0 |
|  | 10 | 4 | 5 | 5 | 0 | 0 | 0 | 0 |
| 285 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 286 | 40 | 5 | 5 | 5 | 1 | 0 | 0 | 0 |
|  | 20 | 5 | 5 | 5 | 0 | 0 | 0 | 0 |
|  | 10 | 5 | 5 | 5 | 0 | 0 | 0 | 0 |
| 287 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 288 | 40 | 5 | 5 | 5 | 1 | 0 | 0 | 1 |
|  | 20 | 5 | 5 | 5 | 0 | 0 | 0 | 0 |
|  | 10 | 5 | 5 | 5 | 0 | 0 | 0 | 0 |
| 289 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 290 | 40 | 5 | 5 | 5 | 0 | 0 | 0 | 0 |
|  | 20 | 4 | 5 | 5 | 0 | 0 | 0 | 0 |
|  | 10 | 3 | 4 | 5 | 0 | 0 | 0 | 0 |
| 291 | 40 | 4 | 5 | 5 | 0 | 0 | 0 | 0 |
|  | 20 | 4 | 5 | 5 | 0 | 0 | 0 | 0 |
|  | 10 | 4 | 4 | 5 | 0 | 0 | 0 | 0 |
| 292 | 40 | 5 | 5 | 5 | 0 | 0 | 0 | 0 |
|  | 20 | 4 | 5 | 5 | 0 | 0 | 0 | 0 |
|  | 10 | 3 | 5 | 5 | 0 | 0 | 0 | 0 |
| 293 | 40 | 5 | 5 | 5 | 0 | 0 | 0 | 0 |
|  | 20 | 4 | 5 | 5 | 0 | 0 | 0 | 0 |
|  | 10 | 4 | 5 | 5 | 0 | 0 | 0 | 0 |
| 294 | 40 | 5 | 5 | 5 | 0 | 0 | 0 | 0 |
|  | 20 | 4 | 5 | 5 | 0 | 0 | 0 | 0 |
|  | 10 | 3 | 4 | 5 | 0 | 0 | 0 | 0 |
| 295 | 40 | 5 | 5 | 5 | 0 | 0 | 0 | 0 |
|  | 20 | 4 | 5 | 5 | 0 | 0 | 0 | 0 |
|  | 10 | 3 | 4 | 5 | 0 | 0 | 0 | 0 |
| 296 | 40 | 4 | 5 | 5 | 0 | 0 | 0 | 0 |
|  | 20 | 4 | 5 | 5 | 0 | 0 | 0 | 0 |
|  | 10 | 3 | 5 | 5 | 0 | 0 | 0 | 0 |
| 297 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 298 | 40 | 5 | 5 | 5 | 0 | 0 | 0 | 0 |
|  | 20 | 5 | 5 | 5 | 0 | 0 | 0 | 0 |
|  | 10 | 4 | 5 | 5 | 0 | 0 | 0 | 0 |
| 299 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 300 | 40 | 5 | 5 | 5 | 1 | 0 | 0 | 1 |
|  | 20 | 5 | 5 | 5 | 0 | 0 | 0 | 0 |
|  | 10 | 5 | 5 | 5 | 0 | 0 | 0 | 0 |
| 301 | 40 | 5 | 5 | 5 | 0 | 0 | 0 | 0 |
|  | 20 | 5 | 5 | 5 | 0 | 0 | 0 | 0 |
|  | 10 | 5 | 5 | 5 | 0 | 0 | 0 | 0 |
| 302 | 40 | 5 | 5 | 5 | 1 | 0 | 0 | 0 |
|  | 20 | 5 | 5 | 5 | 0 | 0 | 0 | 0 |
|  | 10 | 5 | 5 | 5 | 0 | 0 | 0 | 0 |
| 303 | 40 | 5 | 5 | 5 | 0 | 0 | 0 | 0 |
|  | 20 | 4 | 5 | 5 | 0 | 0 | 0 | 0 |
|  | 10 | 4 | 4 | 5 | 0 | 0 | 0 | 0 |
| 304 | 40 | 4 | 5 | 5 | 0 | 0 | 0 | 0 |
|  | 20 | 4 | 5 | 5 | 0 | 0 | 0 | 0 |
|  | 10 | 4 | 5 | 5 | 0 | 0 | 0 | 0 |
| 305 | 40 | 5 | 5 | 5 | 0 | 0 | 0 | 0 |
|  | 20 | 4 | 5 | 5 | 0 | 0 | 0 | 0 |
|  | 10 | 3 | 4 | 5 | 0 | 0 | 0 | 0 |
| 306 | 40 | 5 | 5 | 5 | 1 | 0 | 0 | 0 |
|  | 20 | 5 | 5 | 5 | 0 | 0 | 0 | 0 |
|  | 10 | 4 | 5 | 5 | 0 | 0 | 0 | 0 |
| 307 | 40 | 5 | 5 | 5 | 0 | 0 | 0 | 0 |
|  | 20 | 4 | 5 | 5 | 0 | 0 | 0 | 0 |
|  | 10 | 4 | 4 | 5 | 0 | 0 | 0 | 0 |
| 308 | 40 | 5 | 5 | 5 | 1 | 0 | 0 | 1 |
|  | 20 | 5 | 5 | 5 | 0 | 0 | 0 | 0 |
|  | 10 | 5 | 5 | 5 | 0 | 0 | 0 | 0 |
| 309 | 40 | 5 | 5 | 5 | 0 | 0 | 0 | 0 |

TABLE 10-continued

| Comp. No. | Dose of Comp. (g/a) | Herbicidal effect | | | Phytotoxicity to crop plants | | | |
|---|---|---|---|---|---|---|---|---|
| | | C.G. | L.T. | L.A. | Wheat | Corn | Soybean | Cotton |
| | 20 | 4 | 5 | 5 | 0 | 0 | 0 | 0 |
| | 10 | 4 | 5 | 5 | 0 | 0 | 0 | 0 |
| 310 | 40 | 4 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 311 | 40 | 5 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 312 | 40 | 5 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 313 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 338 | 40 | 5 | 5 | 5 | 0 | 0 | 1 | 0 |
| | 20 | 5 | 5 | 5 | 0 | 0 | 0 | 0 |
| | 10 | 4 | 5 | 5 | 0 | 0 | 0 | 0 |
| 339 | 40 | 4 | 5 | 5 | 0 | 0 | 0 | 0 |
| | 20 | 4 | 5 | 5 | 0 | 0 | 0 | 0 |
| | 10 | 3 | 5 | 5 | 0 | 0 | 0 | 0 |
| 340 | 40 | 4 | 5 | 5 | 0 | 0 | 0 | 0 |
| | 20 | 4 | 5 | 5 | 0 | 0 | 0 | 0 |
| | 10 | 3 | 5 | 5 | 0 | 0 | 0 | 0 |
| 341 | 40 | 5 | 5 | 5 | 0 | 0 | 1 | 1 |
| | 20 | 5 | 5 | 5 | 0 | 0 | 0 | 0 |
| | 10 | 5 | 5 | 5 | 0 | 0 | 0 | 0 |
| 342 | 40 | 5 | 5 | 5 | 0 | 0 | 0 | 1 |
| | 20 | 5 | 5 | 5 | 0 | 0 | 0 | 0 |
| | 10 | 5 | 5 | 5 | 0 | 0 | 0 | 0 |
| 343 | 40 | 5 | 5 | 5 | 1 | 0 | 1 | 1 |
| | 20 | 5 | 5 | 5 | 0 | 0 | 0 | 0 |
| | 10 | 5 | 5 | 5 | 0 | 0 | 0 | 0 |
| 344 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 345 | 40 | 5 | 5 | 5 | 1 | 0 | 1 | 1 |
| | 20 | 5 | 5 | 5 | 0 | 0 | 0 | 0 |
| | 10 | 5 | 5 | 5 | 0 | 0 | 0 | 0 |
| 346 | 40 | 5 | 5 | 5 | 0 | 0 | 1 | 1 |
| | 20 | 5 | 5 | 5 | 0 | 0 | 0 | 0 |
| | 10 | 5 | 5 | 5 | 0 | 0 | 0 | 0 |
| 347 | 40 | 5 | 5 | 5 | 0 | 0 | 1 | 0 |
| | 20 | 5 | 5 | 5 | 0 | 0 | 0 | 0 |
| | 10 | 5 | 4 | 5 | 0 | 0 | 0 | 0 |
| 348 | 40 | 5 | 5 | 5 | 1 | 0 | 0 | 1 |
| | 20 | 5 | 5 | 5 | 0 | 0 | 0 | 0 |
| | 10 | 5 | 5 | 5 | 0 | 0 | 0 | 0 |
| 349 | 40 | 5 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 350 | 40 | 5 | 5 | 5 | 0 | 0 | 1 | 0 |
| | 20 | 5 | 5 | 5 | 0 | 0 | 0 | 0 |
| | 10 | 4 | 5 | 5 | 0 | 0 | 0 | 0 |
| 351 | 40 | 4 | 5 | 5 | 0 | 0 | 0 | 0 |
| | 20 | 4 | 5 | 5 | 0 | 0 | 0 | 0 |
| | 10 | 3 | 4 | 5 | 0 | 0 | 0 | 0 |
| 352 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 353 | 40 | 5 | 5 | 5 | 1 | 0 | 1 | 0 |
| | 20 | 5 | 5 | 5 | 0 | 0 | 0 | 0 |
| | 10 | 5 | 5 | 5 | 0 | 0 | 0 | 0 |
| 354 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 355 | 40 | 5 | 5 | 5 | 0 | 0 | 1 | 1 |
| | 20 | 5 | 5 | 5 | 0 | 0 | 0 | 0 |
| | 10 | 5 | 5 | 5 | 0 | 0 | 0 | 0 |
| 356 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 357 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 358 | 40 | 5 | 5 | 5 | 0 | 0 | 0 | 1 |
| | 20 | 5 | 5 | 5 | 0 | 0 | 0 | 0 |
| | 10 | 4 | 5 | 5 | 0 | 0 | 0 | 0 |
| 359 | 40 | 5 | 5 | 5 | 0 | 0 | 1 | 0 |
| | 20 | 4 | 5 | 5 | 0 | 0 | 0 | 0 |
| | 10 | 4 | 5 | 5 | 0 | 0 | 0 | 0 |
| 360 | 40 | 5 | 5 | 5 | 1 | 0 | 1 | 0 |
| | 20 | 5 | 5 | 5 | 0 | 0 | 0 | 0 |
| | 10 | 5 | 5 | 5 | 0 | 0 | 0 | 0 |
| 361 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 362 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 363 | 40 | 5 | 5 | 5 | 0 | 0 | 1 | 1 |
| | 20 | 5 | 5 | 5 | 0 | 0 | 0 | 0 |
| | 10 | 5 | 5 | 5 | 0 | 0 | 0 | 0 |
| 364 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 365 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 366 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 367 | 40 | 4 | 5 | 5 | 0 | 0 | 0 | 0 |
| | 20 | 4 | 4 | 5 | 0 | 0 | 0 | 0 |
| | 10 | 4 | 4 | 5 | 0 | 0 | 0 | 0 |
| 368 | 40 | 5 | 5 | 5 | 0 | 0 | 0 | 0 |
| | 20 | 5 | 5 | 5 | 0 | 0 | 0 | 0 |
| | 10 | 3 | 4 | 5 | 0 | 0 | 0 | 0 |
| 369 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 370 | 40 | 5 | 5 | 5 | 1 | 0 | 1 | 0 |
| | 20 | 5 | 5 | 5 | 0 | 0 | 0 | 0 |
| | 10 | 5 | 5 | 5 | 0 | 0 | 0 | 0 |
| 371 | 40 | 5 | 5 | 5 | 0 | 0 | 0 | 0 |
| | 20 | 4 | 5 | 5 | 0 | 0 | 0 | 0 |
| | 10 | 4 | 3 | 5 | 0 | 0 | 0 | 0 |
| 372 | 40 | 5 | 5 | 5 | 0 | 0 | 0 | 0 |
| | 20 | 4 | 4 | 5 | 0 | 0 | 0 | 0 |
| | 10 | 4 | 4 | 5 | 0 | 0 | 0 | 0 |
| 373 | 40 | 5 | 5 | 5 | 0 | 0 | 0 | 0 |
| | 20 | 5 | 4 | 5 | 0 | 0 | 0 | 0 |
| | 10 | 3 | 4 | 5 | 0 | 0 | 0 | 0 |
| 374 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 375 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 376 | 40 | 5 | 5 | 5 | 0 | 0 | 0 | 0 |
| | 20 | 4 | 5 | 5 | 0 | 0 | 0 | 0 |
| | 10 | 4 | 4 | 5 | 0 | 0 | 0 | 0 |
| 377 | 40 | 5 | 5 | 5 | 1 | 0 | 1 | 1 |
| | 20 | 5 | 5 | 5 | 0 | 0 | 0 | 0 |
| | 10 | 5 | 5 | 5 | 0 | 0 | 0 | 0 |
| 378 | 40 | 5 | 5 | 5 | 0 | 0 | 1 | 1 |
| | 20 | 5 | 5 | 5 | 0 | 0 | 0 | 0 |
| | 10 | 5 | 5 | 5 | 0 | 0 | 0 | 0 |
| 388 | 40 | 4 | 5 | 5 | 0 | 0 | 0 | 0 |
| | 20 | 4 | 5 | 5 | 0 | 0 | 0 | 0 |
| | 10 | 3 | 5 | 4 | 0 | 0 | 0 | 0 |
| 389 | 40 | 5 | 5 | 5 | 1 | 0 | 1 | 1 |
| | 20 | 5 | 5 | 5 | 0 | 0 | 0 | 0 |
| | 10 | 5 | 5 | 5 | 0 | 0 | 0 | 0 |
| 390 | 40 | 5 | 5 | 5 | 1 | 0 | 1 | 0 |
| | 20 | 5 | 5 | 5 | 0* | 0 | 0 | 0 |
| | 10 | 5 | 5 | 5 | 0 | 0 | 0 | 0 |
| 391 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 392 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 393 | 40 | 5 | 5 | 5 | 1 | 0 | 1 | 1 |
| | 20 | 5 | 5 | 5 | 0 | 0 | 0 | 0 |

TABLE 10-continued

| Comp. No. | Dose of Comp. (g/a) | Herbicidal effect C.G. | L.T. | L.A. | Phytotoxicity to crop plants Wheat | Corn | Soybean | Cotton |
|---|---|---|---|---|---|---|---|---|
| | 10 | 5 | 5 | 5 | 0 | 0 | 0 | 0 |
| 394 | 40 | 5 | 5 | 5 | 0 | 0 | 1 | 0 |
| | 20 | 5 | 5 | 5 | 0 | 0 | 0 | 0 |
| | 10 | 4 | 5 | 5 | 0 | 0 | 0 | 0 |
| 395 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 396 | 40 | 5 | 5 | 5 | 0 | 0 | 1 | 0 |
| | 20 | 5 | 5 | 5 | 0 | 0 | 0 | 0 |
| | 10 | 5 | 5 | 5 | 0 | 0 | 0 | 0 |
| 397 | 40 | 5 | 5 | 5 | 0 | 0 | 1 | 1 |
| | 20 | 5 | 5 | 5 | 0 | 0 | 0 | 0 |
| | 10 | 5 | 5 | 5 | 0 | 0 | 0 | 0 |
| 398 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 399 | 40 | 5 | 5 | 5 | 0 | 0 | 0 | 0 |
| | 20 | 5 | 5 | 5 | 0 | 0 | 0 | 0 |
| | 10 | 5 | 5 | 5 | 0 | 0 | 0 | 0 |
| 400 | 40 | 5 | 5 | 5 | 0 | 0 | 0 | 1 |
| | 20 | 5 | 5 | 5 | 0 | 0 | 0 | 0 |
| | 10 | 5 | 5 | 5 | 0 | 0 | 0 | 0 |
| 401 | 40 | 5 | 5 | 5 | 1 | 0 | 1 | 0 |
| | 20 | 5 | 5 | 5 | 0 | 0 | 0 | 0 |
| | 10 | 5 | 5 | 5 | 0 | 0 | 0 | 0 |
| 402 | 40 | 5 | 5 | 5 | 0 | 0 | 0 | 1 |
| | 20 | 5 | 5 | 5 | 0 | 0 | 0 | 0 |
| | 10 | 5 | 4 | 5 | 0 | 0 | 0 | 0 |
| 403 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 404 | 40 | 5 | 5 | 5 | 0 | 0 | 0 | 0 |
| | 20 | 5 | 5 | 5 | 0 | 0 | 0 | 0 |
| | 10 | 4 | 4 | 5 | 0 | 0 | 0 | 0 |
| 405 | 40 | 4 | 5 | 5 | 0 | 0 | 0 | 0 |
| | 20 | 4 | 4 | 5 | 0 | 0 | 0 | 0 |
| | 10 | 3 | 4 | 5 | 0 | 0 | 0 | 0 |
| 406 | 40 | 5 | 5 | 5 | 0 | 0 | 0 | 0 |
| | 20 | 4 | 5 | 5 | 0 | 0 | 0 | 0 |
| | 10 | 4 | 5 | 5 | 0 | 0 | 0 | 0 |
| 407 | 40 | 5 | 5 | 5 | 0 | 0 | 0 | 0 |
| | 20 | 5 | 5 | 5 | 0 | 0 | 0 | 0 |
| | 10 | 4 | 5 | 5 | 0 | 0 | 0 | 0 |
| 409 | 40 | 5 | 5 | 5 | 0 | 0 | 0 | 1 |
| | 20 | 5 | 5 | 5 | 0 | 0 | 0 | 0 |
| | 10 | 5 | 5 | 5 | 0 | 0 | 0 | 0 |
| Ref. A | 40 | 5 | 5 | 5 | 2 | 0 | 0 | 1 |
| | 20 | 4 | 4 | 4 | 1 | 0 | 0 | 0 |
| | 10 | 2 | 3 | 4 | 0 | 0 | 0 | 0 |
| Ref. B | 40 | 5 | 5 | 5 | 2 | 0 | 0 | 0 |
| | 20 | 4 | 4 | 5 | 0 | 0 | 0 | 0 |
| | 10 | 3 | 2 | 4 | 0 | 0 | 0 | 0 |
| Ref. E | 40 | 5 | 5 | 5 | 4 | 3 | 1 | 2 |
| | 20 | 5 | 5 | 5 | 3 | 1 | 0 | 1 |
| | 10 | 3 | 4 | 3 | 0 | 0 | 0 | 0 |
| Ref. F | 40 | 5 | 5 | 5 | 3 | 1 | 1 | 1 |
| | 20 | 4 | 4 | 4 | 1 | 0 | 1 | 0 |
| | 10 | 2 | 2 | 4 | 0 | 0 | 0 | 0 |
| Non-treatment | — | 0 | 0 | 0 | 0 | 0 | 0 | 0 |

Test J

Foliage treatment test

Each polyethylene pot was filled with black volcano ash soil and manured and seeds of Sawa millet, Large Crabgrass and Radish were respectively sown in each pot. The pot was kept in a greenhouse. When Sawa millet and Large crabgrass were grown to 2 leaf stage and Radish to 1 leaf stage, each solution prepared by diluting each emulsifiable concentrate containing each of Compounds of the present invention and Reference Compounds, at a concentration of 0.5, 0.25 or 0.125%, was sprayed at a rate of 10 liter per are by a small power pressurized sprayer and the pot in the greenhouse was observed.

Fifteen days after the treatment, herbicidal effects were observed. The results are shown in Table 11.

The herbicidal effects are rated as those of Test A.

Test K

In accordance with the experiment of Test J, each herbicidal effect of each of Compounds of the present invention and Reference Compounds was tested. The results are shown in Table 12.

Test L

In accordance with the experiment of Test J, each test was carried out by using the compounds shown in Table 1. The results are shown in Table 13.

TABLE 11

| Compound No. | Concentration % | Herbicidal effect S.M. | C.G. | Radish |
|---|---|---|---|---|
| 1 | 0.5 | 4 | 5 | 5 |
| | 0.25 | 4 | 5 | 5 |
| | 0.125 | 3 | 3 | 5 |
| 2 | 0.5 | 4 | 5 | 5 |
| | 0.25 | 4 | 4 | 5 |
| | 0.125 | 3 | 3 | 5 |
| 3 | 0.5 | 5 | 5 | 5 |
| | 0.25 | 4 | 5 | 5 |
| | 0.125 | 4 | 4 | 5 |
| 4 | 0.5 | 4 | 5 | 5 |
| | 0.25 | 4 | 4 | 5 |
| | 0.125 | 3 | 3 | 5 |
| 5 | 0.5 | 5 | 5 | 5 |
| | 0.25 | 5 | 5 | 5 |
| | 0.125 | 4 | 4 | 5 |
| 6 | 0.5 | 4 | 5 | 5 |
| | 0.25 | 4 | 4 | 5 |
| | 0.125 | 4 | 3 | 3 |
| 7 | 0.5 | 4 | 5 | 5 |
| | 0.25 | 4 | 4 | 5 |
| | 0.125 | 3 | 3 | 4 |
| 8 | 0.5 | 4 | 5 | 5 |
| | 0.25 | 4 | 4 | 5 |
| | 0.125 | 4 | 4 | 5 |
| 9 | 0.5 | 5 | 5 | 5 |
| | 0.25 | 5 | 5 | 5 |
| | 0.125 | 5 | 5 | 5 |
| 10 | 0.5 | 5 | 5 | 5 |
| | 0.25 | 4 | 5 | 5 |
| | 0.125 | 4 | 4 | 5 |
| 11 | 0.5 | 5 | 5 | 5 |
| | 0.25 | 5 | 5 | 5 |
| | 0.125 | 4 | 5 | 5 |
| 12 | 0.5 | 5 | 5 | 5 |
| | 0.25 | 5 | 5 | 5 |
| | 0.125 | 5 | 5 | 5 |
| 13 | 0.5 | 5 | 5 | 5 |
| | 0.25 | 5 | 5 | 5 |
| | 0.125 | 5 | 5 | 5 |
| 14 | 0.5 | 5 | 5 | 5 |
| | 0.25 | 5 | 5 | 5 |
| | 0.125 | 5 | 5 | 5 |
| 15 | 0.5 | 5 | 5 | 5 |
| | 0.25 | 5 | 5 | 5 |
| | 0.125 | 5 | 5 | 5 |
| 16 | 0.5 | 5 | 5 | 5 |
| | 0.25 | 4 | 5 | 5 |
| | 0.125 | 4 | 5 | 5 |
| 17 | 0.5 | 5 | 5 | 5 |
| | 0.25 | 5 | 5 | 5 |
| | 0.125 | 5 | 5 | 5 |
| 18 | 0.5 | 5 | 5 | 5 |
| | 0.25 | 5 | 5 | 5 |
| | 0.125 | 4 | 5 | 5 |
| 19 | 0.5 | 4 | 5 | 5 |
| | 0.25 | 4 | 4 | 5 |
| | 0.125 | 3 | 3 | 5 |
| 20 | 0.5 | 5 | 5 | 5 |

TABLE 11-continued

| Compound No. | Concentration % | Herbicidal effect | | |
|---|---|---|---|---|
| | | S.M. | C.G. | Radish |
| | 0.25 | 4 | 5 | 5 |
| | 0.125 | 4 | 4 | 5 |
| 21 | 0.5 | 4 | 5 | 5 |
| | 0.25 | 4 | 4 | 5 |
| | 0.125 | 4 | 4 | 5 |
| 22 | 0.5 | 5 | 5 | 5 |
| | 0.25 | 5 | 5 | 5 |
| | 0.125 | 5 | 5 | 5 |
| 23 | 0.5 | 5 | 5 | 5 |
| | 0.25 | 4 | 5 | 5 |
| | 0.125 | 4 | 4 | 5 |
| 24 | 0.5 | 5 | 5 | 5 |
| | 0.25 | 4 | 4 | 5 |
| | 0.125 | 3 | 4 | 4 |
| 25 | 0.5 | 5 | 5 | 5 |
| | 0.25 | 4 | 5 | 5 |
| | 0.125 | 4 | 4 | 5 |
| 26 | 0.5 | 5 | 5 | 5 |
| | 0.25 | 5 | 5 | 5 |
| | 0.125 | 5 | 5 | 5 |
| 27 | 0.5 | 5 | 5 | 5 |
| | 0.25 | 5 | 5 | 4 |
| | 0.125 | 4 | 5 | 4 |
| 28 | 0.5 | 5 | 5 | 5 |
| | 0.25 | 4 | 5 | 5 |
| | 0.125 | 3 | 4 | 5 |
| 29 | 0.5 | 5 | 5 | 5 |
| | 0.25 | 5 | 5 | 5 |
| | 0.125 | 5 | 5 | 5 |
| 30 | 0.5 | 4 | 5 | 5 |
| | 0.25 | 4 | 5 | 5 |
| | 0.125 | 3 | 4 | 5 |
| 31 | 0.5 | 4 | 5 | 5 |
| | 0.25 | 4 | 5 | 5 |
| | 0.125 | 4 | 4 | 5 |
| 32 | 0.5 | 5 | 5 | 5 |
| | 0.25 | 5 | 5 | 5 |
| | 0.125 | 4 | 5 | 5 |
| 33 | 0.5 | 5 | 5 | 5 |
| | 0.25 | 5 | 5 | 4 |
| | 0.125 | 4 | 5 | 4 |
| 34 | 0.5 | 4 | 5 | 5 |
| | 0.25 | 4 | 4 | 4 |
| | 0.125 | 4 | 4 | 4 |
| 35 | 0.5 | 5 | 5 | 5 |
| | 0.25 | 5 | 5 | 5 |
| | 0.125 | 5 | 5 | 5 |
| 36 | 0.5 | 5 | 5 | 5 |
| | 0.25 | 4 | 4 | 5 |
| | 0.125 | 3 | 4 | 4 |
| 37 | 0.5 | 5 | 5 | 5 |
| | 0.25 | 4 | 5 | 5 |
| | 0.125 | 4 | 4 | 4 |
| 38 | 0.5 | 5 | 5 | 5 |
| | 0.25 | 5 | 5 | 5 |
| | 0.125 | 5 | 5 | 5 |
| 39 | 0.5 | 5 | 5 | 5 |
| | 0.25 | 5 | 5 | 5 |
| | 0.125 | 4 | 5 | 4 |
| 40 | 0.5 | 5 | 5 | 5 |
| | 0.25 | 5 | 5 | 5 |
| | 0.125 | 5 | 5 | 5 |
| 41 | 0.5 | 5 | 5 | 5 |
| | 0.25 | 5 | 5 | 5 |
| | 0.125 | 5 | 5 | 5 |
| 42 | 0.5 | 5 | 5 | 5 |
| | 0.25 | 5 | 5 | 5 |
| | 0.125 | 5 | 5 | 5 |
| 43 | 0.5 | 5 | 5 | 5 |
| | 0.25 | 5 | 5 | 5 |
| | 0.125 | 5 | 5 | 5 |
| 44 | 0.5 | 5 | 5 | 5 |
| | 0.25 | 5 | 5 | 5 |
| | 0.125 | 5 | 5 | 5 |
| 45 | 0.5 | 5 | 5 | 5 |
| | 0.25 | 4 | 5 | 5 |
| | 0.125 | 4 | 4 | 4 |
| 46 | 0.5 | 5 | 5 | 5 |
| | 0.25 | 4 | 5 | 5 |
| | 0.125 | 4 | 4 | 4 |
| 47 | 0.5 | 4 | 5 | 5 |
| | 0.25 | 4 | 5 | 5 |
| | 0.125 | 3 | 4 | 5 |
| 48 | 0.5 | 5 | 5 | 5 |
| | 0.25 | 5 | 5 | 5 |
| | 0.125 | 4 | 5 | 5 |
| 49 | 0.5 | 5 | 5 | 5 |
| | 0.25 | 4 | 5 | 4 |
| | 0.125 | 4 | 4 | 4 |
| 50 | 0.5 | 5 | 5 | 5 |
| | 0.25 | 4 | 5 | 4 |
| | 0.125 | 3 | 4 | 4 |
| 90 | 0.5 | 5 | 5 | 5 |
| | 0.25 | 4 | 5 | 5 |
| | 0.125 | 4 | 4 | 4 |
| 91 | 0.5 | 4 | 5 | 5 |
| | 0.25 | 4 | 5 | 5 |
| | 0.125 | 3 | 4 | 5 |
| 92 | 0.5 | 5 | 5 | 5 |
| | 0.25 | 4 | 5 | 5 |
| | 0.125 | 3 | 4 | 4 |
| 93 | 0.5 | 4 | 5 | 5 |
| | 0.25 | 4 | 5 | 5 |
| | 0.125 | 3 | 4 | 4 |
| 94 | 0.5 | 4 | 5 | 5 |
| | 0.25 | 4 | 4 | 4 |
| | 0.125 | 4 | 4 | 4 |
| 95 | 0.5 | 4 | 5 | 5 |
| | 0.25 | 4 | 4 | 5 |
| | 0.125 | 3 | 3 | 4 |
| 96 | 0.5 | 4 | 5 | 5 |
| | 0.25 | 4 | 4 | 5 |
| | 0.125 | 4 | 4 | 4 |
| 97 | 0.5 | 5 | 5 | 5 |
| | 0.25 | 4 | 4 | 5 |
| | 0.125 | 3 | 4 | 4 |
| 98 | 0.5 | 4 | 5 | 5 |
| | 0.25 | 4 | 4 | 5 |
| | 0.125 | 4 | 4 | 4 |
| 99 | 0.5 | 5 | 5 | 5 |
| | 0.25 | 5 | 5 | 5 |
| | 0.125 | 4 | 5 | 5 |
| 100 | 0.5 | 5 | 5 | 5 |
| | 0.25 | 5 | 5 | 5 |
| | 0.125 | 4 | 5 | 5 |
| 101 | 0.5 | 5 | 5 | 5 |
| | 0.25 | 4 | 5 | 5 |
| | 0.125 | 4 | 5 | 5 |
| 102 | 0.5 | 5 | 5 | 5 |
| | 0.25 | 4 | 5 | 5 |
| | 0.125 | 4 | 4 | 4 |
| 103 | 0.5 | 5 | 5 | 5 |
| | 0.25 | 4 | 5 | 5 |
| | 0.125 | 3 | 4 | 5 |
| 104 | 0.5 | 5 | 5 | 5 |
| | 0.25 | 4 | 4 | 5 |
| | 0.125 | 3 | 4 | 5 |
| 105 | 0.5 | 4 | 5 | 5 |
| | 0.25 | 4 | 4 | 5 |
| | 0.125 | 3 | 3 | 5 |
| 106 | 0.5 | 5 | 5 | 5 |
| | 0.25 | 4 | 4 | 5 |
| | 0.125 | 3 | 4 | 5 |
| 107 | 0.5 | 5 | 5 | 5 |
| | 0.25 | 4 | 5 | 5 |
| | 0.125 | 4 | 4 | 5 |
| 108 | 0.5 | 5 | 5 | 5 |
| | 0.25 | 4 | 4 | 5 |
| | 0.125 | 3 | 4 | 5 |
| 109 | 0.5 | 5 | 5 | 5 |
| | 0.25 | 4 | 5 | 5 |
| | 0.125 | 3 | 4 | 5 |
| 110 | 0.5 | 5 | 5 | 5 |
| | 0.25 | 4 | 5 | 5 |
| | 0.125 | 4 | 4 | 5 |
| 111 | 0.5 | 4 | 5 | 5 |
| | 0.25 | 4 | 4 | 5 |
| | 0.125 | 4 | 4 | 5 |

TABLE 11-continued

| Compound No. | Concentration % | Herbicidal effect S.M. | C.G. | Radish |
|---|---|---|---|---|
| 112 | 0.5 | 5 | 5 | 5 |
|  | 0.25 | 4 | 5 | 5 |
|  | 0.125 | 3 | 4 | 5 |
| 113 | 0.5 | 5 | 5 | 5 |
|  | 0.25 | 4 | 5 | 5 |
|  | 0.125 | 4 | 4 | 5 |
| 114 | 0.5 | 5 | 5 | 5 |
|  | 0.25 | 4 | 5 | 5 |
|  | 0.125 | 4 | 4 | 5 |
| 115 | 0.5 | 4 | 5 | 5 |
|  | 0.25 | 4 | 5 | 5 |
|  | 0.125 | 3 | 4 | 5 |
| 116 | 0.5 | 4 | 5 | 5 |
|  | 0.25 | 4 | 5 | 5 |
|  | 0.125 | 4 | 4 | 5 |
| 117 | 0.5 | 5 | 5 | 5 |
|  | 0.25 | 4 | 5 | 5 |
|  | 0.125 | 3 | 3 | 5 |
| 118 | 0.5 | 4 | 5 | 5 |
|  | 0.25 | 4 | 4 | 5 |
|  | 0.125 | 4 | 4 | 5 |
| 119 | 0.5 | 5 | 5 | 5 |
|  | 0.25 | 4 | 4 | 5 |
|  | 0.125 | 3 | 4 | 5 |
| 120 | 0.5 | 4 | 5 | 5 |
|  | 0.25 | 4 | 4 | 5 |
|  | 0.125 | 4 | 4 | 5 |
| 190 | 0.5 | 5 | 5 | 5 |
|  | 0.25 | 5 | 5 | 5 |
|  | 0.125 | 4 | 5 | 5 |
| 191 | 0.5 | 5 | 5 | 5 |
|  | 0.25 | 4 | 5 | 5 |
|  | 0.125 | 4 | 4 | 5 |
| 192 | 0.5 | 5 | 5 | 5 |
|  | 0.25 | 5 | 5 | 4 |
|  | 0.125 | 5 | 5 | 4 |
| 193 | 0.5 | 5 | 5 | 5 |
|  | 0.25 | 4 | 5 | 5 |
|  | 0.125 | 4 | 4 | 4 |
| 194 | 0.5 | 5 | 5 | 5 |
|  | 0.25 | 5 | 5 | 4 |
|  | 0.125 | 4 | 4 | 4 |
| 195 | 0.5 | 4 | 5 | 5 |
|  | 0.25 | 4 | 4 | 4 |
|  | 0.125 | 4 | 4 | 4 |
| 196 | 0.5 | 4 | 5 | 5 |
|  | 0.25 | 4 | 4 | 4 |
|  | 0.125 | 4 | 4 | 4 |
| 197 | 0.5 | 5 | 5 | 5 |
|  | 0.25 | 4 | 4 | 5 |
|  | 0.125 | 3 | 4 | 4 |
| 198 | 0.5 | 5 | 5 | 5 |
|  | 0.25 | 4 | 5 | 5 |
|  | 0.125 | 3 | 3 | 4 |
| 199 | 0.5 | 4 | 5 | 5 |
|  | 0.25 | 4 | 4 | 4 |
|  | 0.125 | 3 | 4 | 4 |
| 200 | 0.5 | 5 | 5 | 5 |
|  | 0.25 | 4 | 4 | 5 |
|  | 0.125 | 3 | 4 | 4 |
| 201 | 0.5 | 5 | 5 | 5 |
|  | 0.25 | 4 | 5 | 4 |
|  | 0.125 | 3 | 4 | 4 |
| 202 | 0.5 | 5 | 5 | 5 |
|  | 0.25 | 4 | 4 | 5 |
|  | 0.125 | 3 | 4 | 4 |
| 203 | 0.5 | 4 | 5 | 5 |
|  | 0.25 | 4 | 4 | 5 |
|  | 0.125 | 4 | 4 | 4 |
| 204 | 0.5 | 5 | 5 | 5 |
|  | 0.25 | 5 | 5 | 5 |
|  | 0.125 | 4 | 5 | 4 |
| 205 | 0.5 | 5 | 5 | 5 |
|  | 0.25 | 4 | 4 | 5 |
|  | 0.125 | 3 | 4 | 4 |
| Reference A | 0.5 | 4 | 5 | 5 |
|  | 0.25 | 3 | 4 | 5 |
|  | 0.125 | 1 | 2 | 3 |
| Reference B | 0.5 | 5 | 5 | 5 |
|  | 0.25 | 3 | 4 | 4 |
|  | 0.125 | 2 | 2 | 3 |
| Reference G | 0.5 | 5 | 5 | 4 |
|  | 0.25 | 4 | 5 | 3 |
|  | 0.125 | 3 | 2 | 3 |
| Non-treatment | — | 0 | 0 | 0 |

TABLE 12

| Compound No. | Concentration % | Herbicidal effect S.M. | C.G. | Radish |
|---|---|---|---|---|
| 228 | 0.5 | 5 | 5 | 5 |
|  | 0.25 | 4 | 5 | 5 |
|  | 0.125 | 4 | 5 | 5 |
| 229 | 0.5 | 5 | 5 | 5 |
|  | 0.25 | 5 | 5 | 5 |
|  | 0.125 | 4 | 5 | 5 |
| 230 | 0.5 | 5 | 5 | 5 |
|  | 0.25 | 5 | 5 | 5 |
|  | 0.125 | 5 | 5 | 5 |
| 231 | 0.5 | 5 | 5 | 5 |
|  | 0.25 | 5 | 5 | 5 |
|  | 0.125 | 5 | 5 | 5 |
| 232 | 0.5 | 5 | 5 | 5 |
|  | 0.25 | 4 | 5 | 5 |
|  | 0.125 | 4 | 4 | 5 |
| 233 | 0.5 | 5 | 5 | 5 |
|  | 0.25 | 5 | 5 | 5 |
|  | 0.125 | 4 | 4 | 4 |
| 234 | 0.5 | 5 | 5 | 5 |
|  | 0.25 | 5 | 5 | 5 |
|  | 0.125 | 3 | 4 | 4 |
| 235 | 0.5 | 5 | 5 | 5 |
|  | 0.25 | 4 | 5 | 5 |
|  | 0.125 | 4 | 4 | 5 |
| 236 | 0.5 | 5 | 5 | 5 |
|  | 0.25 | 4 | 5 | 5 |
|  | 0.125 | 4 | 3 | 5 |
| Reference A | 0.5 | 5 | 5 | 5 |
|  | 0.25 | 4 | 4 | 5 |
|  | 0.125 | 2 | 3 | 3 |
| Reference B | 0.5 | 5 | 5 | 5 |
|  | 0.25 | 3 | 4 | 4 |
|  | 0.125 | 3 | 3 | 4 |
| Reference G | 0.5 | 5 | 5 | 4 |
|  | 0.25 | 5 | 5 | 4 |
|  | 0.125 | 2 | 3 | 2 |
| Non-treatment | — | 0 | 0 | 0 |

TABLE 13

| Compound No. | Concentration % | Herbicidal effect S.M. | C.G. | Radish |
|---|---|---|---|---|
| 239 | 0.5 | 5 | 5 | 5 |
|  | 0.25 | 4 | 5 | 5 |
|  | 0.125 | 4 | 4 | 5 |
| 240 | 0.5 | 5 | 5 | 5 |
|  | 0.25 | 5 | 5 | 5 |
|  | 0.125 | 3 | 5 | 5 |
| 241 | 0.5 | 5 | 5 | 5 |
|  | 0.25 | 5 | 5 | 5 |
|  | 0.125 | 5 | 5 | 5 |
| 242 | 0.5 | 5 | 5 | 5 |
|  | 0.25 | 5 | 5 | 5 |
|  | 0.125 | 4 | 5 | 5 |
| 243 | 0.5 | 5 | 5 | 5 |
|  | 0.25 | 5 | 5 | 5 |
|  | 0.125 | 5 | 4 | 5 |
| 244 | 0.5 | 5 | 5 | 5 |
|  | 0.25 | 5 | 5 | 5 |
|  | 0.125 | 5 | 5 | 5 |
| 245 | 0.5 | 5 | 5 | 5 |
|  | 0.25 | 5 | 5 | 5 |
|  | 0.125 | 5 | 5 | 5 |
| 246 | 0.5 | 5 | 5 | 5 |
|  | 0.25 | 4 | 5 | 5 |

TABLE 13-continued

| Compound No. | Concentration % | Herbicidal effect | | |
|---|---|---|---|---|
| | | S.M. | C.G. | Radish |
| 247 | 0.125 | 4 | 4 | 5 |
| | 0.5 | 5 | 5 | 5 |
| | 0.25 | 4 | 5 | 5 |
| 248 | 0.125 | 4 | 5 | 5 |
| | 0.5 | 5 | 5 | 5 |
| | 0.25 | 5 | 5 | 5 |
| 249 | 0.125 | 4 | 5 | 5 |
| | 0.5 | 5 | 5 | 5 |
| | 0.25 | 5 | 5 | 5 |
| 250 | 0.125 | 4 | 5 | 5 |
| | 0.5 | 4 | 5 | 5 |
| | 0.25 | 4 | 5 | 5 |
| 251 | 0.125 | 4 | 4 | 5 |
| | 0.5 | 5 | 5 | 5 |
| | 0.25 | 4 | 5 | 5 |
| 252 | 0.125 | 4 | 4 | 5 |
| | 0.5 | 4 | 5 | 5 |
| | 0.25 | 4 | 5 | 5 |
| 253 | 0.125 | 3 | 4 | 5 |
| | 0.5 | 5 | 5 | 5 |
| | 0.25 | 5 | 5 | 5 |
| 254 | 0.125 | 5 | 5 | 5 |
| | 0.5 | 5 | 5 | 5 |
| | 0.25 | 5 | 5 | 5 |
| 255 | 0.125 | 5 | 5 | 5 |
| | 0.5 | 5 | 5 | 5 |
| | 0.25 | 5 | 5 | 5 |
| 256 | 0.125 | 4 | 4 | 5 |
| | 0.5 | 5 | 5 | 5 |
| | 0.25 | 4 | 5 | 5 |
| 257 | 0.125 | 4 | 4 | 5 |
| | 0.5 | 5 | 5 | 5 |
| | 0.25 | 5 | 5 | 5 |
| 258 | 0.125 | 5 | 5 | 5 |
| | 0.5 | 5 | 5 | 5 |
| | 0.25 | 4 | 5 | 5 |
| 259 | 0.125 | 4 | 4 | 5 |
| | 0.5 | 5 | 5 | 5 |
| | 0.25 | 5 | 5 | 5 |
| 260 | 0.125 | 5 | 5 | 5 |
| | 0.5 | 4 | 5 | 5 |
| | 0.25 | 4 | 4 | 5 |
| 261 | 0.125 | 4 | 4 | 5 |
| | 0.5 | 5 | 5 | 5 |
| | 0.25 | 4 | 4 | 5 |
| 262 | 0.125 | 3 | 4 | 5 |
| | 0.5 | 5 | 5 | 5 |
| | 0.25 | 4 | 4 | 5 |
| 263 | 0.125 | 4 | 4 | 5 |
| | 0.5 | 5 | 5 | 5 |
| | 0.25 | 5 | 5 | 5 |
| 308 | 0.125 | 5 | 5 | 5 |
| | 0.5 | 5 | 5 | 5 |
| | 0.25 | 4 | 5 | 5 |
| 309 | 0.125 | 4 | 4 | 5 |
| | 0.5 | 5 | 5 | 5 |
| | 0.25 | 4 | 4 | 5 |
| 310 | 0.125 | 4 | 4 | 5 |
| | 0.5 | 4 | 5 | 5 |
| | 0.25 | 4 | 5 | 5 |
| 311 | 0.125 | 3 | 3 | 5 |
| | 0.5 | 4 | 5 | 5 |
| | 0.25 | 4 | 4 | 5 |
| 312 | 0.125 | 3 | 3 | 5 |
| | 0.5 | 5 | 5 | 5 |
| | 0.25 | 4 | 5 | 5 |
| 313 | 0.125 | 4 | 4 | 5 |
| | 0.5 | 5 | 5 | 5 |
| | 0.25 | 5 | 5 | 5 |
| | 0.125 | 5 | 5 | 5 |
| 314 | 0.5 | 5 | 5 | 5 |
| | 0.25 | 5 | 5 | 5 |
| | 0.125 | 5 | 5 | 5 |
| 315 | 0.5 | 4 | 5 | 5 |
| | 0.25 | 4 | 5 | 5 |
| | 0.125 | 4 | 4 | 5 |
| 316 | 0.5 | 5 | 5 | 5 |
| | 0.25 | 4 | 4 | 5 |
| | 0.125 | 3 | 3 | 5 |
| 317 | 0.5 | 4 | 5 | 5 |
| | 0.25 | 4 | 5 | 5 |
| | 0.125 | 4 | 4 | 5 |
| 318 | 0.5 | 4 | 5 | 5 |
| | 0.25 | 4 | 4 | 5 |
| | 0.125 | 3 | 3 | 5 |
| 319 | 0.5 | 4 | 5 | 5 |
| | 0.25 | 4 | 4 | 5 |
| | 0.125 | 3 | 4 | 5 |
| 320 | 0.5 | 4 | 5 | 5 |
| | 0.25 | 4 | 5 | 5 |
| | 0.125 | 4 | 3 | 5 |
| 321 | 0.5 | 5 | 5 | 5 |
| | 0.25 | 4 | 5 | 5 |
| | 0.125 | 4 | 4 | 5 |
| 322 | 0.5 | 5 | 5 | 5 |
| | 0.25 | 4 | 4 | 5 |
| | 0.125 | 3 | 4 | 5 |
| 323 | 0.5 | 5 | 5 | 5 |
| | 0.25 | 5 | 4 | 5 |
| | 0.125 | 3 | 4 | 5 |
| 324 | 0.5 | 4 | 5 | 5 |
| | 0.25 | 4 | 4 | 5 |
| | 0.125 | 4 | 4 | 4 |
| 325 | 0.5 | 4 | 5 | 5 |
| | 0.25 | 4 | 4 | 5 |
| | 0.125 | 3 | 3 | 5 |
| 326 | 0.5 | 5 | 5 | 5 |
| | 0.25 | 4 | 5 | 5 |
| | 0.125 | 4 | 4 | 5 |
| 327 | 0.5 | 5 | 5 | 5 |
| | 0.25 | 5 | 5 | 5 |
| | 0.125 | 3 | 4 | 5 |
| 328 | 0.5 | 5 | 5 | 5 |
| | 0.25 | 4 | 5 | 5 |
| | 0.125 | 3 | 4 | 5 |
| 388 | 0.5 | 5 | 5 | 5 |
| | 0.25 | 4 | 5 | 5 |
| | 0.125 | 4 | 4 | 5 |
| 389 | 0.5 | 5 | 5 | 5 |
| | 0.25 | 5 | 5 | 5 |
| | 0.125 | 4 | 5 | 5 |
| 390 | 0.5 | 5 | 5 | 5 |
| | 0.25 | 5 | 5 | 5 |
| | 0.125 | 4 | 5 | 5 |
| 391 | 0.5 | 5 | 5 | 5 |
| | 0.25 | 5 | 5 | 5 |
| | 0.125 | 4 | 5 | 5 |
| 392 | 0.5 | 5 | 5 | 5 |
| | 0.25 | 5 | 5 | 5 |
| | 0.125 | 3 | 4 | 5 |
| 393 | 0.5 | 5 | 5 | 5 |
| | 0.25 | 5 | 5 | 5 |
| | 0.125 | 3 | 4 | 5 |
| 394 | 0.5 | 5 | 5 | 5 |
| | 0.25 | 4 | 5 | 5 |
| | 0.125 | 3 | 4 | 5 |
| 395 | 0.5 | 4 | 5 | 5 |
| | 0.25 | 4 | 5 | 5 |
| | 0.125 | 4 | 4 | 5 |
| 396 | 0.5 | 5 | 5 | 5 |
| | 0.25 | 5 | 5 | 5 |
| | 0.125 | 3 | 4 | 5 |
| 397 | 0.5 | 5 | 5 | 5 |
| | 0.25 | 5 | 5 | 5 |
| | 0.125 | 5 | 5 | 5 |
| 398 | 0.5 | 5 | 5 | 5 |
| | 0.25 | 4 | 5 | 5 |
| | 0.125 | 3 | 4 | 5 |
| 399 | 0.5 | 4 | 5 | 5 |
| | 0.25 | 4 | 5 | 5 |
| | 0.125 | 4 | 4 | 5 |
| 400 | 0.5 | 4 | 5 | 5 |
| | 0.25 | 4 | 4 | 5 |
| | 0.125 | 3 | 4 | 5 |
| 401 | 0.5 | 5 | 5 | 5 |
| | 0.25 | 5 | 5 | 5 |
| | 0.125 | 5 | 5 | 5 |
| 402 | 0.5 | 5 | 5 | 5 |

TABLE 13-continued

| Compound No. | Concentration % | Herbicidal effect S.M. | C.G. | Radish |
|---|---|---|---|---|
| | 0.25 | 5 | 5 | 5 |
| | 0.125 | 3 | 4 | 5 |
| 403 | 0.5 | 4 | 5 | 5 |
| | 0.25 | 4 | 5 | 5 |
| | 0.125 | 4 | 4 | 5 |
| 404 | 0.5 | 5 | 5 | 5 |
| | 0.25 | 4 | 5 | 5 |
| | 0.125 | 4 | 5 | 5 |
| 405 | 0.5 | 4 | 5 | 5 |
| | 0.25 | 4 | 5 | 5 |
| | 0.125 | 3 | 4 | 5 |
| 406 | 0.5 | 4 | 5 | 5 |
| | 0.25 | 3 | 4 | 5 |
| | 0.125 | 3 | 4 | 5 |
| 407 | 0.5 | 5 | 5 | 5 |
| | 0.25 | 5 | 5 | 5 |
| | 0.125 | 3 | 4 | 5 |
| 408 | 0.5 | 5 | 5 | 5 |
| | 0.25 | 5 | 5 | 5 |
| | 0.125 | 5 | 5 | 5 |
| 409 | 0.5 | 5 | 5 | 5 |
| | 0.25 | 5 | 5 | 5 |
| | 0.125 | 5 | 5 | 5 |
| 410 | 0.5 | 5 | 5 | 5 |
| | 0.25 | 4 | 5 | 5 |
| | 0.125 | 4 | 4 | 5 |
| 411 | 0.5 | 5 | 5 | 5 |
| | 0.25 | 5 | 5 | 5 |
| | 0.125 | 3 | 5 | 5 |
| 412 | 0.5 | 5 | 5 | 5 |
| | 0.25 | 5 | 5 | 5 |
| | 0.125 | 5 | 5 | 5 |
| 413 | 0.5 | 5 | 5 | 5 |
| | 0.25 | 5 | 5 | 5 |
| | 0.125 | 4 | 5 | 5 |
| 414 | 0.5 | 5 | 5 | 5 |
| | 0.25 | 4 | 5 | 5 |
| | 0.125 | 4 | 4 | 5 |
| 415 | 0.5 | 5 | 5 | 5 |
| | 0.25 | 5 | 5 | 5 |
| | 0.125 | 5 | 5 | 5 |
| 416 | 0.5 | 5 | 5 | 5 |
| | 0.25 | 5 | 5 | 5 |
| | 0.125 | 5 | 5 | 5 |
| 417 | 0.5 | 5 | 5 | 5 |
| | 0.25 | 5 | 5 | 5 |
| | 0.125 | 4 | 5 | 5 |
| 418 | 0.5 | 5 | 5 | 5 |
| | 0.25 | 3 | 5 | 5 |
| | 0.125 | 3 | 4 | 5 |
| 419 | 0.5 | 5 | 5 | 5 |
| | 0.25 | 4 | 5 | 5 |
| | 0.125 | 3 | 4 | 5 |
| 420 | 0.5 | 5 | 5 | 5 |
| | 0.25 | 4 | 5 | 5 |
| | 0.125 | 3 | 4 | 5 |
| 421 | 0.5 | 4 | 5 | 5 |
| | 0.25 | 4 | 5 | 5 |
| | 0.125 | 3 | 4 | 5 |
| 422 | 0.5 | 4 | 5 | 5 |
| | 0.25 | 4 | 5 | 5 |
| | 0.125 | 3 | 4 | 5 |
| 423 | 0.5 | 5 | 5 | 5 |
| | 0.25 | 5 | 5 | 5 |
| | 0.125 | 5 | 5 | 5 |
| 424 | 0.5 | 5 | 5 | 5 |
| | 0.25 | 4 | 5 | 5 |
| | 0.125 | 4 | 4 | 5 |
| 425 | 0.5 | 5 | 5 | 5 |
| | 0.25 | 4 | 5 | 5 |
| | 0.125 | 3 | 4 | 5 |
| 426 | 0.5 | 5 | 5 | 5 |
| | 0.25 | 4 | 5 | 5 |
| | 0.125 | 3 | 5 | 5 |
| 427 | 0.5 | 4 | 5 | 5 |
| | 0.25 | 4 | 5 | 5 |
| | 0.125 | 4 | 4 | 5 |
| 428 | 0.5 | 5 | 5 | 5 |
| | 0.25 | 4 | 5 | 5 |
| | 0.125 | 3 | 4 | 4 |
| 429 | 0.5 | 4 | 5 | 5 |
| | 0.25 | 4 | 5 | 5 |
| | 0.125 | 3 | 4 | 4 |
| 430 | 0.5 | 5 | 5 | 5 |
| | 0.25 | 4 | 5 | 5 |
| | 0.125 | 4 | 4 | 5 |
| 431 | 0.5 | 5 | 5 | 5 |
| | 0.25 | 4 | 4 | 5 |
| | 0.125 | 3 | 4 | 5 |
| 432 | 0.5 | 5 | 5 | 5 |
| | 0.25 | 4 | 4 | 5 |
| | 0.125 | 3 | 4 | 4 |
| 433 | 0.5 | 5 | 5 | 5 |
| | 0.25 | 4 | 5 | 5 |
| | 0.125 | 4 | 4 | 5 |
| 434 | 0.5 | 5 | 5 | 5 |
| | 0.25 | 4 | 5 | 5 |
| | 0.125 | 3 | 4 | 5 |
| Reference A | 0.5 | 5 | 5 | 5 |
| | 0.25 | 4 | 4 | 5 |
| | 0.125 | 1 | 2 | 3 |
| Reference B | 0.5 | 5 | 5 | 5 |
| | 0.25 | 3 | 4 | 4 |
| | 0.125 | 1 | 3 | 3 |
| Reference G | 0.5 | 5 | 5 | 4 |
| | 0.25 | 4 | 5 | 4 |
| | 0.125 | 3 | 3 | 2 |
| Non-treatment | — | 0 | 0 | 0 |

We claim:
1. A method of controlling weeds in the cultivation of a crop plant by applying a herbicidally effective amount of an N-(3-substituted oxyphenyl)-3,4,5,6-tetrahydrophthalimide of the formula:

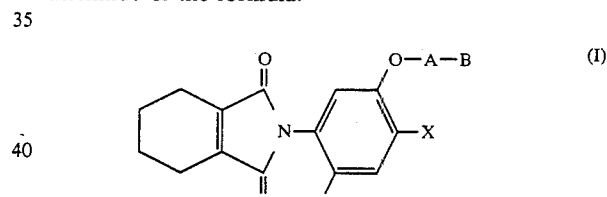

wherein X and Y each represent hydrogen or halogen;

A represents 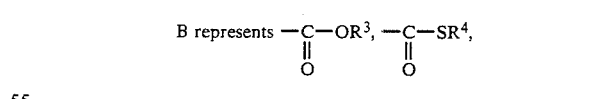, $-\underset{\underset{CHCH_3}{\|}}{C}-$, or $-CH_2CH=CH-$;

B represents 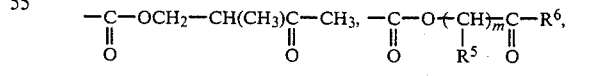

$$-\underset{\underset{O}{\|}}{C}-N\underset{R^8}{\overset{R^7}{\diagdown}},$$

or $-CN$; $R^1$ is hydrogen or $C_{1-10}$ alkyl, phenyl chlorophenyl, bromophenyl, dichlorophenyl, methylchlorophenyl, methylphenyl or nitrophenyl; $R^2$ is hydrogen or $C_{1-4}$ alkyl; $R^3$ is hydrogen or a $C_{1-12}$ straight or branched alkyl, $C_{2-5}$ alkenyl, $C_{2-5}$ alkynyl, $C_{1-5}$ haloalkyl, $C_{3-4}$ haloalkenyl, $C_{2-4}$ cyanoalkyl, $C_{2-4}$ hydroxyalkyl, $C_{3-6}$ alkoxyalkyl, $C_{5-8}$ alkoxyalkoxyalkyl, $C_{7-10}$ alkoxyalkoxyalkoxyalkyl, $C_{3-8}$ alkylthioalkyl, $C_{4-8}$ cycloalkyl, $C_{7-9}$ aralkyl, chlorobenzyl, bromobenzyl, phenyl, γ-butyrolactone optionally substituted by methyl, an alkali metal cation, an alkaline earth metal cation, ammonium cation, or an ammonium cation having 1 to 4 alkyl substituents, wherein the total carbon atom content of the ammonium cation is 1 to 9 carbon atoms; $R^4$ is $C_{1-12}$ alkyl, $C_{3-6}$ alkoxycarbonylalkyl or benzyl; $R^5$ is hydrogen or methyl; $R^6$ is methyl or phenyl; $R^7$ and $R^8$ can be the same or different and each is hydrogen, $C_{1-10}$ branched or straight chain alkyl, $C_{2-5}$ alkenyl, $C_{2-5}$ alkynyl, $C_{2-6}$ haloalkyl, $C_{2-6}$ hydroxyalkyl, alkoxyalkyl, aralkyl, phenyl, chlorophenyl, bromophenyl, methylphenyl, methoxyphenyl, pyrimidine, thiazole, pyridine, $C_{1-6}$ alkoxy, $C_{2-4}$ alkenyloxy, amino, methylamino, phenylamino, dimethylamino, $C_{1-4}$ alkanesulfonyl, benzenesulfonyl, toluenesulfonyl, chlorobenzenesulfonyl, methoxybenzenesulfonyl or cyclohexyl; and

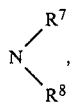

wherein $R^7$ and $R^8$ together form a piperidine, or optionally together with an oxygen form a morpholine, isoxazolidine, or tetrahydroisoxazine ring; and m and n each represent an integer of 1 to 3.

2. The method of claim 1, wherein said weeds are controlled in the cultivation of a crop plant selected from the group consisting of soybean, cotton, sugar beat, sunflower, peas, potatoes, cucumbers, rice, wheat, barley, oats, rye, corn and sugar cane.

3. The method of claim 1, wherein in said tetrahydrophthalimide compound, group X is chlorine and group Y is hydrogen.

4. The method of claim 1, wherein in said tetrahydrophthalimide compound, group X is bromine and group Y is hydrogen.

5. The method of claim 1, wherein in said tetrahydrophthalimide compound, A represents —CHR¹—; $R^1$ represents H, $C_{1-10}$ alkyl or phenyl; B represents —CONR⁷R⁸; $R^7$ and $R^8$ each represent H, $C_{1-10}$ branched or straight chain alkyl, $C_{2-5}$ alkenyl, $C_{2-5}$ alkynyl, $C_{2-6}$ haloalkyl, $C_{2-6}$ hydroxyalkyl, methoxyethyl, benzyl, phenyl, chlorophenyl, bromophenyl, methylphenyl, methoxyphenyl, pyrimidine, thiazole, pyridine, $C_{1-6}$ alkoxy, $C_{2-4}$ alkenyloxy, amino, methylamino, phenylamino, dimethylamino, $C_{1-4}$ alkanesulfonyl, benzenesulfonyl, toluenesulfonyl, chlorobenzenesulfonyl, methoxybenzenesulfonyl, or cyclohexyl; and

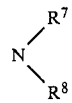

wherein $R^7$ and $R^8$ together form a piperidine, or optionally together with an oxygen form a morpholine, isoxazolidine, or tetrahydroisoxazine ring.

6. The method of claim 5, wherein in said tetrahydrophthalimide compound, $R^1$ represents a $C_{1-4}$ alkyl group; $R^7$ represents H, a $C_{1-7}$ alkyl or a $C_{1-4}$ alkoxy group; $R^8$ represents a $C_{1-7}$ alkyl, a $C_{1-4}$ alkoxy, a $C_{2-4}$ haloalkyl, a $C_{2-4}$ hydroxyalkyl, phenyl, aralkyl, a $C_{3-4}$ alkenyl or a $C_{3-5}$ alkynyl group.

7. The method of claim 6, wherein in said tetrahydrophthalimide compound, $R^1$ represents a $C_{1-4}$ alkyl group; $R^7$ represents H, a $C_{1-7}$ alkyl or a $C_{1-4}$ alkoxy group; $R^8$ represents a $C_{1-7}$ alkyl, a $C_{1-4}$ alkoxy, a $C_{3-4}$ alkenyl, a $C_{3-5}$ alkynyl or benzyl group.

8. The method of claim 7, wherein in said tetrahydrophthalimide compound, X represents Cl or Br; Y represents H; $R^1$ represents a $C_{1-3}$ alkyl group; $R^7$ represents H, methyl or methoxy group; $R^8$ represents a $C_{1-4}$ alkyl, a $C_{1-4}$ alkoxy, allyl, propargyl or benzyl group.

9. The method of claims 1, 3 or 4, wherein in said tetrahydrophthalimide compound,

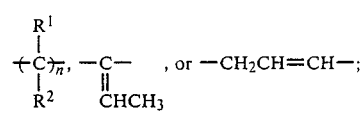

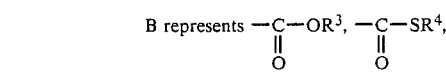

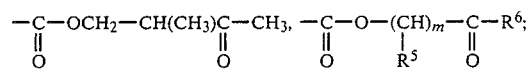

$R^1$ represents hydrogen or $C_{1-10}$ alkyl, phenyl, chlorophenyl, bromophenyl, dichlorophenyl, methylchlorophenyl, methylphenyl or nitrophenyl; $R^2$ represents hydrogen or $C_{1-14}$ alkyl; $R^3$ represents hydrogen, $C_{1-12}$ straight or branched alkyl, $C_{2-5}$ alkenyl, $C_{2-5}$ alkynyl, $C_{1-5}$ haloalkyl, $C_{3-4}$ haloalkenyl, $C_{2-4}$ cyanoalkyl, $C_{2-4}$ hydroxyalkyl, $C_{3-6}$ alkoxyalkyl, $C_{5-8}$ alkoxyalkoxyalkyl, $C_{7-10}$ alkoxyalkoxyalkoxyalkyl, $C_{3-8}$ alkylthioalkyl, $C_{4-8}$ cycloalkyl, $C_{7-9}$ aralkyl, chlorobenzyl, bromobenzyl, phenyl, γ-butyrolactone optionally substituted by methyl, an alkali metal cation, an alkaline earth metal cation, ammonium cation or an ammonium cation containing from 1 to 4 alkyl groups, wherein the total carbon atom content of the ammonium cation is 1 to 9 carbon atoms; $R^4$ represents $C_{1-12}$ alkyl, $C_{3-6}$ alkoxycarbonylalkyl or benzyl; $R^5$ represents hydrogen of methyl; $R^6$ represents methyl or phenyl; and n and m are each an integer of 1 to 3.

10. The method of claim 9, wherein in said tetrahydrophthalimide compound, group A represents —CHR¹—, wherein $R^1$ represents a $C_{1-4}$ alkyl or phenyl group; B represents —COOR³ or —COSR⁴; $R^3$ represents a $C_{1-6}$ alkyl group; and $R^4$ represents a $C_{1-10}$ alkyl group.

11. The method of claim 10, wherein in said tetrahydrophthalimide compound, group $R^3$ represents a $C_{1-4}$ alkyl group; and $R^4$ represents a $C_{2-3}$ alkyl group.

12. The method of claims 1, 3 or 4, wherein in said tetrahydrophthalimide compound, group A represents —(CHR¹)$_n$—; $R^1$ represents H or an alkyl group; n is an integer of 1 to 3 and B represents CN.

* * * * *